(12) United States Patent
Wang et al.

(10) Patent No.: US 7,498,046 B2
(45) Date of Patent: Mar. 3, 2009

(54) COMPOSITION FOR INDUCING IMMUNE RESPONSE COMPRISING INVERTED MICROSOMES

(75) Inventors: Ping Wang, West Smithfield (GB); Suling Li, West Smithfield (GB)

(73) Assignee: Queen Mary & Westfield College, London (GB)

( * ) Notice: Subject to any disclaimer, the term of this patent is extended or adjusted under 35 U.S.C. 154(b) by 0 days.

(21) Appl. No.: 10/566,823

(22) PCT Filed: Jul. 30, 2004

(86) PCT No.: PCT/GB2004/003285

§ 371 (c)(1),
(2), (4) Date: Jun. 20, 2006

(87) PCT Pub. No.: WO2005/011730

PCT Pub. Date: Feb. 10, 2005

(65) Prior Publication Data

US 2007/0184022 A1 Aug. 9, 2007

(30) Foreign Application Priority Data

Aug. 1, 2003 (GB) ................................. 0318096.5

(51) Int. Cl.
*A61K 35/12* (2006.01)
*A61K 38/19* (2006.01)
*A61K 39/002* (2006.01)
*A61K 39/02* (2006.01)
*A61K 39/12* (2006.01)

(52) U.S. Cl. .................. 424/520; 424/184.1; 424/204.1; 424/234.1; 424/265.1; 424/274.1; 435/810

(58) Field of Classification Search ....................... None
See application file for complete search history.

(56) References Cited

U.S. PATENT DOCUMENTS

2002/0122818 A1 9/2002 Albani
2002/0122820 A1 9/2002 Hildebrand et al.

FOREIGN PATENT DOCUMENTS

EP 0 356 340 2/1990

OTHER PUBLICATIONS

Singh et al., Nature Biotechnology, 1999, 17: 1075-1081.*
Greenwald et al., Annu. Rev. Immunol., 2005, 23: 515-548.*
De Lemos-Chiarandini et al., J. Cell Biol., 1987, 104: 209-219.*
Dorland's Medical Dictionary, 2008, 2 pages.*

Anthony et al., "Comprehensive Determinant Mapping of the Hepatitis C-Specific CD8 Cell Repertoire Reveals Unpredicted Immune Hierarchy," *Clinical Immunology*, (2002) 103(3):264-276.
Celis, "Getting peptide vaccines to work; just a matter of quality control?" *J. Clin. Invest.* (2002) 110:1765-1768.
He et al., "Quantitative analysis of hepatitis C Virus-specific CD8+ T cells in peripheral blood and liver using peptide-MHC tetramers," *Proc. Nat'l. Acad. Sci.*, (1999) 96:5692-5697.
Kaul et al., "CD8+ lymphocytes respond to different HIV epitopes in seronegative and infected subjects," *Journal of Clinical Investigation* (2001) 107(10):1303-1310.
Koziel et al., "Hepatitis C Virus (HCV)-Specific Cytotoxic T Lymphocytes Recognize Epitopes in the Core and Envelope Proteins of HCV," *Journal of Virology*, (1993) 67(12):7522-7532.
Li et al., "Peptide-bound Major Histocompatibility Complex Class I Molecules Associate with Tapasin before Dissociation from transporter Associated with Antigen Processing," *Journal of Biological Chemistry*, (1999) 274(13):8649-8654.
Li et al., "Cytokine-induced Src Homology 2 Protein (CIS) Promotes T cell Receptor-mediated Proliferation and Prolongs Survival of Activated T Cells," *J. Exp. Med.*, (2000) 191(6):985-994.
Li et al., "Cloning and functional characterization of a subunit of the transporter associated with antigen processing," *Proc. Nat'l. Acad. Sci.*, (1997) 94:8708-8713.
Li et al., "Tapasin is Required for Efficient Peptide Binding to Transporter Associated with Antigen Processing," *Journal of Biological Chemistry*, (2000) 275(3):1581-1586.
Mallet-Designe, "Detection of Low-Avidity CD4+ T Cells Using Recombinant Artificial APC: Following the Antivalbumin Immune Response," *Journal of Immunology*, (2003) 170:123-131.
Paulsson et al., "Distinct differences in association of MGC class I with endoplasmic reticulum proteins in wild-type, and β2-microglobulin- and TAP-deficient cell lines," *International Immunology*, (2001) 13(8):1063-1073.
Paulsson et al., "Association of Tapasin and COPI Provides a Mechanism for the Retrograde Transport of Major Histocompatibility Complex (MHC) Class I Molecules from the Golgi Complex to the Endoplasmic Reticulum," *Journal of Biological Chemistry* (2002) 277(21):18266-18271.
Paulsson et al., "Assembly of tapasin-associated MHC class I in the absence of the transporter associated with antigen processing (TAP)," *International Immunology*, (2001) 13(1):23-29.
Saraste et al., "Temperature-sensitive steps in the transport of secretory proteins through the Golgi complex in exocrine pancreatic cells," *Proc Natl Acad Sci USA* (1986) 83(17):6425-6429.
Tartour et al., "Development of non-live vectors and procedures (liposomes, pseudo-viral particles, toxin, beads, adjuvants . . . ) as tools for cancer vaccines.," *Immunology Letters* (2000) 74(1):45-50.
Wang et al., "Binding of H-2Kb-specific Peptides to TAP and major Histocompatibility Complex Class I in Microsomes from Wild-type, TAP1, and β2-Mocroglobulin Mutant Mice," *Journal of Biological Chemistry*, (1996) 271(40):24830-24835.

* cited by examiner

*Primary Examiner*—Ilia Ouspenski
(74) *Attorney, Agent, or Firm*—Pepper Hamilton LLP

(57) ABSTRACT

A vaccine composition is provided which comprises inverted microsomes or fragments thereof from an animal cell in association with an externally disposed peptide antigen and a protein of the MHC.

20 Claims, 9 Drawing Sheets

HLA class I histocompatibility antigen A-2

```
mavmaprtlv lllsgalalt qtwagshsmr yfftsvsrpg rgeprfiavg yvddtqfvrf
dsdaasqrme prapwieqeg peywdgetrk vkahsqthrv dlgtlrgyyn qseagshtvq
rmygcdvgsd wrflrgyhqy aydgkdyial kedlrswtaa dmaaqttkhk weaahvaeql
raylegtcve wlrrylengk etlqrtdapk thmthhavsd heatlrcwal sfypaeitlt
wqrdgedqtq dtelvetrpa gdgtfqkwaa vvvpsgqeqr ytchvqhegl pkpltlrwep
ssqptipivg iiaglvlfga vitgavvaav mwrrkssdrk ggsysqaass dsaqgsdvsl
tackv
```

HLA class I histocompatibility antigen B-7

```
mlvmaprtvl lllsaalalt etwagshsmr yfytsvsrpg rgeprfisvg yvddtqfvrf
dsdaaspree prapwieqeg peywdrntqi ykaqaqtdre slrnlrgyyn qseagshtlq
smygcdvgpd grllrghdqy aydgkdyial nedlrswtaa dtaaqitqrk weaareaeqr
raylegecve wlrrylengk dkleradppk thvthhpisd heatlrcwal gfypaeitlt
wqrdgedqtq dtelvetrpa gdrtfqkwaa vvvpsgeeqr ytchvqhegl pkpltlrwep
ssqstvpivg ivaglavlav vvigavvaav mcrrkssggk ggsysqaacs dsaqgsdvsl
ta
```

FIG. 13

HLA class II histocompatibility antigen DRB3-1

```
mvclklpggs slaaltvtlm vlssrlafag dtrprflelr ksechffngt ervryldryf
hnqeeflrfd sdvgeyravt elgrpvaesw nsqkdlleqk rgrvdnycrh nygvgesftv
qrrvhpqvtv ypaktqplqh hnllvcsvsg fypgsievrw frngqeekag vvstgliqng
dwtfqtlvml etvprsgevy tcqvehpsvt saltvewrar sesaqskmls gvggfvlgll
flgaglfiyf rnqkghsglq ptgfls
```

MHC class II histocompatibility antigen HLA-DQ alpha 1

```
milnkalllg alalttvmsp cggedivadh vasygvnlyq sygpsgqyth efdgdeqfyv
dlgrketvwc lpvlrqfrfd pqfaltniav tkhnlnilik rsnstaatne vpevtvfsks
pvtlgqpntl iclvdnifpp vvnitwlsng hsvtegvset sflsksdhsf fkisyltflp
sadeiydckv ehwgldepll khwepeipap mseltetvvc alglsvglvg ivvgtvfiir
glrsvgasrh qgpl
```

FIG. 14

SEQUENCE LISTING

<160> NUMBER OF SEQ ID NOS: 317

<210> SEQ ID NO 1
<211> LENGTH: 8
<212> TYPE: PRT
<213> ORGANISM: Influenza virus

<400> SEQUENCE: 1

Ser Ile Ile Asn Phe Glu Lys Leu
1               5

<210> SEQ ID NO 2
<211> LENGTH: 9
<212> TYPE: PRT
<213> ORGANISM: Influenza virus

<400> SEQUENCE: 2

Ala Ser Asn Glu Asn Met Glu Thr Met
1               5

<210> SEQ ID NO 3
<211> LENGTH: 10
<212> TYPE: PRT
<213> ORGANISM: Homo sapiens

<400> SEQUENCE: 3

Tyr Leu Gln Leu Val Phe Gly Ile Glu Val
1               5                   10

<210> SEQ ID NO 4
<211> LENGTH: 7
<212> TYPE: PRT
<213> ORGANISM: Unknown
<220> FEATURE:
<223> OTHER INFORMATION: H2-Kb-binding ovalbumin (OVA) peptide

<400> SEQUENCE: 4

Ser Ile Ile Phe Glu Lys Leu
1               5

<210> SEQ ID NO 5
<211> LENGTH: 9
<212> TYPE: PRT
<213> ORGANISM: Homo sapiens

<400> SEQUENCE: 5

Glu Ala Asp Pro Thr Gly His Ser Tyr
1               5

<210> SEQ ID NO 6
<211> LENGTH: 9
<212> TYPE: PRT
<213> ORGANISM: Homo sapiens

<400> SEQUENCE: 6

Ser Leu Phe Arg Ala Val Ile Thr Lys
1               5

<210> SEQ ID NO 7
<211> LENGTH: 9
<212> TYPE: PRT
<213> ORGANISM: Homo sapiens

<400> SEQUENCE: 7

```
Asn Tyr Lys His Cys Phe Pro Glu Ile
1               5
```

<210> SEQ ID NO 8
<211> LENGTH: 10
<212> TYPE: PRT
<213> ORGANISM: Homo sapiens

<400> SEQUENCE: 8

```
Glu Val Tyr Asp Gly Arg Glu His Ser Ala
1               5                   10
```

<210> SEQ ID NO 9
<211> LENGTH: 10
<212> TYPE: PRT
<213> ORGANISM: Homo sapiens

<400> SEQUENCE: 9

```
Arg Glu Pro Val Thr Lys Ala Glu Met Leu
1               5                   10
```

<210> SEQ ID NO 10
<211> LENGTH: 9
<212> TYPE: PRT
<213> ORGANISM: Homo sapiens

<400> SEQUENCE: 10

```
Asp Pro Ala Arg Tyr Glu Phe Leu Trp
1               5
```

<210> SEQ ID NO 11
<211> LENGTH: 9
<212> TYPE: PRT
<213> ORGANISM: Homo sapiens

<400> SEQUENCE: 11

```
Ser Ala Phe Pro Thr Thr Ile Asn Phe
1               5
```

<210> SEQ ID NO 12
<211> LENGTH: 9
<212> TYPE: PRT
<213> ORGANISM: Homo sapiens

<400> SEQUENCE: 12

```
Ser Ala Tyr Gly Glu Pro Arg Lys Leu
1               5
```

<210> SEQ ID NO 13
<211> LENGTH: 9
<212> TYPE: PRT
<213> ORGANISM: Homo sapiens

<400> SEQUENCE: 13

```
Lys Met Val Glu Leu Val His Phe Leu
1               5
```

<210> SEQ ID NO 14
<211> LENGTH: 9
<212> TYPE: PRT
<213> ORGANISM: Homo sapiens

<400> SEQUENCE: 14

```
Glu Tyr Leu Gln Leu Val Phe Gly Ile
```

```
1               5

<210> SEQ ID NO 15
<211> LENGTH: 9
<212> TYPE: PRT
<213> ORGANISM: Homo sapiens

<400> SEQUENCE: 15

Glu Val Asp Pro Ile Gly His Leu Tyr
1               5

<210> SEQ ID NO 16
<211> LENGTH: 9
<212> TYPE: PRT
<213> ORGANISM: Homo sapiens

<400> SEQUENCE: 16

Phe Leu Trp Gly Pro Arg Ala Leu Val
1               5

<210> SEQ ID NO 17
<211> LENGTH: 9
<212> TYPE: PRT
<213> ORGANISM: Homo sapiens

<400> SEQUENCE: 17

Thr Phe Pro Asp Leu Glu Ser Glu Phe
1               5

<210> SEQ ID NO 18
<211> LENGTH: 9
<212> TYPE: PRT
<213> ORGANISM: Homo sapiens

<400> SEQUENCE: 18

Ile Met Pro Lys Ala Gly Leu Leu Ile
1               5

<210> SEQ ID NO 19
<211> LENGTH: 10
<212> TYPE: PRT
<213> ORGANISM: Homo sapiens

<400> SEQUENCE: 19

Met Glu Val Asp Pro Ile Gly His Leu Tyr
1               5                   10

<210> SEQ ID NO 20
<211> LENGTH: 9
<212> TYPE: PRT
<213> ORGANISM: Homo sapiens

<400> SEQUENCE: 20

Trp Gln Tyr Phe Phe Pro Val Ile Phe
1               5

<210> SEQ ID NO 21
<211> LENGTH: 10
<212> TYPE: PRT
<213> ORGANISM: Homo sapiens

<400> SEQUENCE: 21

Gly Val Tyr Asp Gly Arg Glu His Thr Val
1               5                   10
```

```
<210> SEQ ID NO 22
<211> LENGTH: 9
<212> TYPE: PRT
<213> ORGANISM: Homo sapiens

<400> SEQUENCE: 22

Met Val Lys Ile Ser Gly Gly Pro Arg
1               5

<210> SEQ ID NO 23
<211> LENGTH: 9
<212> TYPE: PRT
<213> ORGANISM: Homo sapiens

<400> SEQUENCE: 23

Gly Leu Tyr Asp Gly Met Glu His Leu
1               5

<210> SEQ ID NO 24
<211> LENGTH: 9
<212> TYPE: PRT
<213> ORGANISM: Homo sapiens

<400> SEQUENCE: 24

Val Arg Ile Gly His Leu Tyr Ile Leu
1               5

<210> SEQ ID NO 25
<211> LENGTH: 9
<212> TYPE: PRT
<213> ORGANISM: Homo sapiens

<400> SEQUENCE: 25

Ala Ala Arg Ala Val Phe Leu Ala Leu
1               5

<210> SEQ ID NO 26
<211> LENGTH: 9
<212> TYPE: PRT
<213> ORGANISM: Homo sapiens

<400> SEQUENCE: 26

Phe Leu Trp Gly Pro Arg Ala Tyr Ala
1               5

<210> SEQ ID NO 27
<211> LENGTH: 8
<212> TYPE: PRT
<213> ORGANISM: Homo sapiens

<400> SEQUENCE: 27

Tyr Arg Pro Arg Pro Arg Arg Tyr
1               5

<210> SEQ ID NO 28
<211> LENGTH: 9
<212> TYPE: PRT
<213> ORGANISM: Homo sapiens

<400> SEQUENCE: 28

Tyr Tyr Trp Pro Arg Pro Arg Arg Tyr
1               5

<210> SEQ ID NO 29
```

```
<211> LENGTH: 11
<212> TYPE: PRT
<213> ORGANISM: Homo sapiens

<400> SEQUENCE: 29

Met Thr Gln Gly Gln His Phe Leu Gln Lys Val
1               5                   10

<210> SEQ ID NO 30
<211> LENGTH: 11
<212> TYPE: PRT
<213> ORGANISM: Homo sapiens

<400> SEQUENCE: 30

Ser Leu Leu Met Trp Ile Thr Gln Cys Phe Leu
1               5                   10

<210> SEQ ID NO 31
<211> LENGTH: 9
<212> TYPE: PRT
<213> ORGANISM: Homo sapiens

<400> SEQUENCE: 31

Ser Leu Leu Met Trp Ile Thr Gln Cys
1               5

<210> SEQ ID NO 32
<211> LENGTH: 9
<212> TYPE: PRT
<213> ORGANISM: Homo sapiens

<400> SEQUENCE: 32

Gln Leu Ser Leu Leu Met Trp Ile Thr
1               5

<210> SEQ ID NO 33
<211> LENGTH: 10
<212> TYPE: PRT
<213> ORGANISM: Homo sapiens

<400> SEQUENCE: 33

Ala Ser Gly Pro Gly Gly Gly Ala Pro Arg
1               5                   10

<210> SEQ ID NO 34
<211> LENGTH: 9
<212> TYPE: PRT
<213> ORGANISM: Homo sapiens

<400> SEQUENCE: 34

Ala Ala Gly Ile Gly Ile Leu Thr Val
1               5

<210> SEQ ID NO 35
<211> LENGTH: 10
<212> TYPE: PRT
<213> ORGANISM: Homo sapiens

<400> SEQUENCE: 35

Glu Ala Ala Gly Ile Gly Ile Leu Thr Val
1               5                   10

<210> SEQ ID NO 36
<211> LENGTH: 9
<212> TYPE: PRT
```

```
<213> ORGANISM: Homo sapiens

<400> SEQUENCE: 36

Ile Leu Thr Val Ile Leu Gly Val Leu
1               5

<210> SEQ ID NO 37
<211> LENGTH: 10
<212> TYPE: PRT
<213> ORGANISM: Homo sapiens

<400> SEQUENCE: 37

Ala Glu Glu Ala Ala Gly Ile Gly Ile Leu
1               5                   10

<210> SEQ ID NO 38
<211> LENGTH: 11
<212> TYPE: PRT
<213> ORGANISM: Homo sapiens

<400> SEQUENCE: 38

Ala Glu Glu Ala Ala Gly Ile Gly Ile Leu Thr
1               5                   10

<210> SEQ ID NO 39
<211> LENGTH: 9
<212> TYPE: PRT
<213> ORGANISM: Homo sapiens

<400> SEQUENCE: 39

Thr Ile Leu Leu Gly Ile Phe Phe Leu
1               5

<210> SEQ ID NO 40
<211> LENGTH: 9
<212> TYPE: PRT
<213> ORGANISM: Homo sapiens

<400> SEQUENCE: 40

Phe Leu Ala Leu Ile Ile Cys Asn Ala
1               5

<210> SEQ ID NO 41
<211> LENGTH: 9
<212> TYPE: PRT
<213> ORGANISM: Homo sapiens

<400> SEQUENCE: 41

Lys Thr Trp Gly Gln Tyr Trp Gln Val
1               5

<210> SEQ ID NO 42
<211> LENGTH: 10
<212> TYPE: PRT
<213> ORGANISM: Homo sapiens

<400> SEQUENCE: 42

Ala Met Leu Gly Thr His Thr Met Glu Val
1               5                   10

<210> SEQ ID NO 43
<211> LENGTH: 9
<212> TYPE: PRT
<213> ORGANISM: Homo sapiens
```

```
<400> SEQUENCE: 43

Met Leu Gly Thr His Thr Met Glu Val
1               5

<210> SEQ ID NO 44
<211> LENGTH: 10
<212> TYPE: PRT
<213> ORGANISM: Homo sapiens

<400> SEQUENCE: 44

Ser Leu Ala Asp Thr Asn Ser Leu Ala Val
1               5                   10

<210> SEQ ID NO 45
<211> LENGTH: 9
<212> TYPE: PRT
<213> ORGANISM: Homo sapiens

<400> SEQUENCE: 45

Ile Thr Asp Gln Val Pro Phe Ser Val
1               5

<210> SEQ ID NO 46
<211> LENGTH: 10
<212> TYPE: PRT
<213> ORGANISM: Homo sapiens

<400> SEQUENCE: 46

Leu Leu Asp Gly Thr Ala Thr Leu Arg Leu
1               5                   10

<210> SEQ ID NO 47
<211> LENGTH: 9
<212> TYPE: PRT
<213> ORGANISM: Homo sapiens

<400> SEQUENCE: 47

Tyr Leu Glu Pro Gly Pro Val Thr Ala
1               5

<210> SEQ ID NO 48
<211> LENGTH: 10
<212> TYPE: PRT
<213> ORGANISM: Homo sapiens

<400> SEQUENCE: 48

Val Leu Tyr Arg Tyr Gly Ser Phe Ser Val
1               5                   10

<210> SEQ ID NO 49
<211> LENGTH: 9
<212> TYPE: PRT
<213> ORGANISM: Homo sapiens

<400> SEQUENCE: 49

Arg Leu Met Lys Gln Asp Phe Ser Val
1               5

<210> SEQ ID NO 50
<211> LENGTH: 9
<212> TYPE: PRT
<213> ORGANISM: Homo sapiens

<400> SEQUENCE: 50
```

```
Arg Leu Pro Arg Ile Phe Cys Ser Cys
1               5

<210> SEQ ID NO 51
<211> LENGTH: 9
<212> TYPE: PRT
<213> ORGANISM: Homo sapiens

<400> SEQUENCE: 51

Leu Ile Tyr Arg Arg Arg Leu Met Lys
1               5

<210> SEQ ID NO 52
<211> LENGTH: 9
<212> TYPE: PRT
<213> ORGANISM: Homo sapiens

<400> SEQUENCE: 52

Ala Leu Asn Phe Pro Gly Ser Gln Lys
1               5

<210> SEQ ID NO 53
<211> LENGTH: 10
<212> TYPE: PRT
<213> ORGANISM: Homo sapiens

<400> SEQUENCE: 53

Ser Leu Ile Tyr Arg Arg Arg Leu Met Lys
1               5                   10

<210> SEQ ID NO 54
<211> LENGTH: 9
<212> TYPE: PRT
<213> ORGANISM: Homo sapiens

<400> SEQUENCE: 54

Ala Leu Leu Ala Val Gly Ala Thr Lys
1               5

<210> SEQ ID NO 55
<211> LENGTH: 9
<212> TYPE: PRT
<213> ORGANISM: Homo sapiens

<400> SEQUENCE: 55

Val Tyr Phe Phe Leu Pro Asp His Leu
1               5

<210> SEQ ID NO 56
<211> LENGTH: 8
<212> TYPE: PRT
<213> ORGANISM: Homo sapiens

<400> SEQUENCE: 56

Ser Asn Asp Gly Pro Thr Leu Ile
1               5

<210> SEQ ID NO 57
<211> LENGTH: 10
<212> TYPE: PRT
<213> ORGANISM: Homo sapiens

<400> SEQUENCE: 57

Val Ser His Ser Phe Pro His Pro Leu Tyr
1               5                   10
```

<210> SEQ ID NO 58
<211> LENGTH: 10
<212> TYPE: PRT
<213> ORGANISM: Homo sapiens

<400> SEQUENCE: 58

Phe Leu Thr Pro Lys Lys Leu Gln Cys Val
1               5                   10

<210> SEQ ID NO 59
<211> LENGTH: 10
<212> TYPE: PRT
<213> ORGANISM: Homo sapiens

<400> SEQUENCE: 59

Val Ile Ser Asn Asp Val Cys Ala Gln Val
1               5                   10

<210> SEQ ID NO 60
<211> LENGTH: 10
<212> TYPE: PRT
<213> ORGANISM: Homo sapiens

<400> SEQUENCE: 60

His Ser Thr Asn Gly Val Thr Arg Ile Tyr
1               5                   10

<210> SEQ ID NO 61
<211> LENGTH: 9
<212> TYPE: PRT
<213> ORGANISM: Homo sapiens

<400> SEQUENCE: 61

Lys Cys Asp Ile Cys Thr Asp Glu Tyr
1               5

<210> SEQ ID NO 62
<211> LENGTH: 11
<212> TYPE: PRT
<213> ORGANISM: Homo sapiens

<400> SEQUENCE: 62

Ser Ser Asp Tyr Val Ile Pro Ile Gly Thr Tyr
1               5                   10

<210> SEQ ID NO 63
<211> LENGTH: 9
<212> TYPE: PRT
<213> ORGANISM: Homo sapiens

<400> SEQUENCE: 63

Tyr Met Asp Gly Thr Met Ser Gln Val
1               5

<210> SEQ ID NO 64
<211> LENGTH: 9
<212> TYPE: PRT
<213> ORGANISM: Homo sapiens

<400> SEQUENCE: 64

Met Leu Leu Ala Val Leu Tyr Cys Leu
1               5

```
<210> SEQ ID NO 65
<211> LENGTH: 9
<212> TYPE: PRT
<213> ORGANISM: Homo sapiens

<400> SEQUENCE: 65

Ala Phe Leu Pro Trp His Arg Leu Phe
1               5

<210> SEQ ID NO 66
<211> LENGTH: 9
<212> TYPE: PRT
<213> ORGANISM: Homo sapiens

<400> SEQUENCE: 66

Ser Glu Ile Trp Arg Asp Ile Asp Phe
1               5

<210> SEQ ID NO 67
<211> LENGTH: 9
<212> TYPE: PRT
<213> ORGANISM: Homo sapiens

<400> SEQUENCE: 67

Met Ser Leu Gln Arg Gln Phe Leu Arg
1               5

<210> SEQ ID NO 68
<211> LENGTH: 9
<212> TYPE: PRT
<213> ORGANISM: Homo sapiens

<400> SEQUENCE: 68

Ser Val Tyr Asp Phe Phe Val Trp Leu
1               5

<210> SEQ ID NO 69
<211> LENGTH: 9
<212> TYPE: PRT
<213> ORGANISM: Homo sapiens

<400> SEQUENCE: 69

Thr Leu Asp Ser Gln Val Met Ser Leu
1               5

<210> SEQ ID NO 70
<211> LENGTH: 9
<212> TYPE: PRT
<213> ORGANISM: Homo sapiens

<400> SEQUENCE: 70

Leu Leu Gly Pro Gly Arg Pro Tyr Arg
1               5

<210> SEQ ID NO 71
<211> LENGTH: 9
<212> TYPE: PRT
<213> ORGANISM: Homo sapiens

<400> SEQUENCE: 71

Ala Asn Asp Pro Ile Phe Val Val Leu
1               5

<210> SEQ ID NO 72
<211> LENGTH: 8
```

<212> TYPE: PRT
<213> ORGANISM: Homo sapiens

<400> SEQUENCE: 72

Ala Phe Leu Arg His Ala Ala Leu
1               5

<210> SEQ ID NO 73
<211> LENGTH: 10
<212> TYPE: PRT
<213> ORGANISM: Homo sapiens

<400> SEQUENCE: 73

Asp Tyr Pro Ser Leu Ser Ala Thr Asp Ile
1               5                   10

<210> SEQ ID NO 74
<211> LENGTH: 11
<212> TYPE: PRT
<213> ORGANISM: Homo sapiens

<400> SEQUENCE: 74

Met Leu Met Ala Gln Glu Ala Leu Ala Phe Leu
1               5                   10

<210> SEQ ID NO 75
<211> LENGTH: 9
<212> TYPE: PRT
<213> ORGANISM: Homo sapiens

<400> SEQUENCE: 75

Tyr Leu Ser Gly Ala Asn Leu Asn Leu
1               5

<210> SEQ ID NO 76
<211> LENGTH: 9
<212> TYPE: PRT
<213> ORGANISM: Homo sapiens

<400> SEQUENCE: 76

His Leu Phe Gly Tyr Ser Trp Tyr Lys
1               5

<210> SEQ ID NO 77
<211> LENGTH: 9
<212> TYPE: PRT
<213> ORGANISM: Homo sapiens

<400> SEQUENCE: 77

Lys Phe His Arg Val Ile Lys Asp Phe
1               5

<210> SEQ ID NO 78
<211> LENGTH: 9
<212> TYPE: PRT
<213> ORGANISM: Homo sapiens

<400> SEQUENCE: 78

Asp Phe Met Ile Gln Gly Gly Asp Phe
1               5

<210> SEQ ID NO 79
<211> LENGTH: 9
<212> TYPE: PRT
<213> ORGANISM: Homo sapiens

```
<400> SEQUENCE: 79

Lys Ile Phe Gly Ser Leu Ala Phe Leu
1               5

<210> SEQ ID NO 80
<211> LENGTH: 9
<212> TYPE: PRT
<213> ORGANISM: Homo sapiens

<400> SEQUENCE: 80

Ile Ile Ser Ala Val Val Gly Ile Leu
1               5

<210> SEQ ID NO 81
<211> LENGTH: 9
<212> TYPE: PRT
<213> ORGANISM: Homo sapiens

<400> SEQUENCE: 81

Arg Leu Leu Gln Glu Thr Glu Leu Val
1               5

<210> SEQ ID NO 82
<211> LENGTH: 9
<212> TYPE: PRT
<213> ORGANISM: Homo sapiens

<400> SEQUENCE: 82

Val Val Leu Gly Val Val Phe Gly Ile
1               5

<210> SEQ ID NO 83
<211> LENGTH: 9
<212> TYPE: PRT
<213> ORGANISM: Homo sapiens

<400> SEQUENCE: 83

Ile Leu His Asn Gly Ala Tyr Ser Leu
1               5

<210> SEQ ID NO 84
<211> LENGTH: 10
<212> TYPE: PRT
<213> ORGANISM: Homo sapiens

<400> SEQUENCE: 84

Tyr Met Ile Met Val Lys Cys Trp Met Ile
1               5                   10

<210> SEQ ID NO 85
<211> LENGTH: 9
<212> TYPE: PRT
<213> ORGANISM: Homo sapiens

<400> SEQUENCE: 85

Val Leu Arg Glu Asn Thr Ser Pro Lys
1               5

<210> SEQ ID NO 86
<211> LENGTH: 9
<212> TYPE: PRT
<213> ORGANISM: Homo sapiens

<400> SEQUENCE: 86
```

```
Ile Leu Ala Lys Phe Leu His Trp Leu
1               5

<210> SEQ ID NO 87
<211> LENGTH: 9
<212> TYPE: PRT
<213> ORGANISM: Homo sapiens

<400> SEQUENCE: 87

Arg Leu Val Asp Asp Phe Leu Leu Val
1               5

<210> SEQ ID NO 88
<211> LENGTH: 9
<212> TYPE: PRT
<213> ORGANISM: Homo sapiens

<400> SEQUENCE: 88

Ser Pro Arg Trp Trp Pro Thr Cys Leu
1               5

<210> SEQ ID NO 89
<211> LENGTH: 9
<212> TYPE: PRT
<213> ORGANISM: Homo sapiens

<400> SEQUENCE: 89

Ser Thr Ala Pro Pro Ala His Gly Val
1               5

<210> SEQ ID NO 90
<211> LENGTH: 9
<212> TYPE: PRT
<213> ORGANISM: Homo sapiens

<400> SEQUENCE: 90

Ser Thr Ala Pro Pro Val His Asn Val
1               5

<210> SEQ ID NO 91
<211> LENGTH: 9
<212> TYPE: PRT
<213> ORGANISM: Homo sapiens

<400> SEQUENCE: 91

Leu Leu Asn Gln Leu Gln Val Asn Leu
1               5

<210> SEQ ID NO 92
<211> LENGTH: 9
<212> TYPE: PRT
<213> ORGANISM: Homo sapiens

<400> SEQUENCE: 92

Met Leu Trp Gly Trp Arg Glu His Val
1               5

<210> SEQ ID NO 93
<211> LENGTH: 9
<212> TYPE: PRT
<213> ORGANISM: Homo sapiens

<400> SEQUENCE: 93

Leu Tyr Val Asp Ser Leu Phe Phe Leu
```

```
<210> SEQ ID NO 94
<211> LENGTH: 9
<212> TYPE: PRT
<213> ORGANISM: Homo sapiens

<400> SEQUENCE: 94

Ala Tyr Gly Leu Asp Phe Tyr Ile Leu
1               5

<210> SEQ ID NO 95
<211> LENGTH: 9
<212> TYPE: PRT
<213> ORGANISM: Homo sapiens

<400> SEQUENCE: 95

Val Pro Tyr Gly Ser Phe Lys His Val
1               5

<210> SEQ ID NO 96
<211> LENGTH: 9
<212> TYPE: PRT
<213> ORGANISM: Homo sapiens

<400> SEQUENCE: 96

Leu Pro Arg Trp Pro Pro Pro Gln Leu
1               5

<210> SEQ ID NO 97
<211> LENGTH: 9
<212> TYPE: PRT
<213> ORGANISM: Homo sapiens

<400> SEQUENCE: 97

Glu Tyr Arg Gly Phe Thr Gln Asp Phe
1               5

<210> SEQ ID NO 98
<211> LENGTH: 9
<212> TYPE: PRT
<213> ORGANISM: Homo sapiens

<400> SEQUENCE: 98

Lys Gly Ser Gly Lys Met Lys Thr Glu
1               5

<210> SEQ ID NO 99
<211> LENGTH: 10
<212> TYPE: PRT
<213> ORGANISM: Homo sapiens

<400> SEQUENCE: 99

Val Tyr Asp Tyr Asn Cys His Val Asp Leu
1               5                   10

<210> SEQ ID NO 100
<211> LENGTH: 9
<212> TYPE: PRT
<213> ORGANISM: Homo sapiens

<400> SEQUENCE: 100

Ala Tyr Ile Asp Phe Glu Met Lys Ile
1               5
```

```
<210> SEQ ID NO 101
<211> LENGTH: 9
<212> TYPE: PRT
<213> ORGANISM: Homo sapiens

<400> SEQUENCE: 101

Arg Met Phe Pro Asn Ala Pro Tyr Leu
1               5

<210> SEQ ID NO 102
<211> LENGTH: 9
<212> TYPE: PRT
<213> ORGANISM: Homo sapiens

<400> SEQUENCE: 102

Gly Val Ala Leu Gln Thr Met Lys Gln
1               5

<210> SEQ ID NO 103
<211> LENGTH: 9
<212> TYPE: PRT
<213> ORGANISM: Homo sapiens

<400> SEQUENCE: 103

Ser Tyr Leu Asp Ser Gly Ile His Phe
1               5

<210> SEQ ID NO 104
<211> LENGTH: 9
<212> TYPE: PRT
<213> ORGANISM: Homo sapiens

<400> SEQUENCE: 104

Phe Pro Ser Asp Ser Trp Cys Tyr Phe
1               5

<210> SEQ ID NO 105
<211> LENGTH: 10
<212> TYPE: PRT
<213> ORGANISM: Homo sapiens

<400> SEQUENCE: 105

Ala Cys Asp Pro His Ser Gly His Phe Val
1               5                   10

<210> SEQ ID NO 106
<211> LENGTH: 9
<212> TYPE: PRT
<213> ORGANISM: Homo sapiens

<400> SEQUENCE: 106

Glu Thr Val Ser Glu Gln Ser Asn Val
1               5

<210> SEQ ID NO 107
<211> LENGTH: 10
<212> TYPE: PRT
<213> ORGANISM: Homo sapiens

<400> SEQUENCE: 107

Val Leu Pro Asp Val Phe Ile Arg Cys Val
1               5                   10

<210> SEQ ID NO 108
```

```
<211> LENGTH: 9
<212> TYPE: PRT
<213> ORGANISM: Homo sapiens

<400> SEQUENCE: 108

Val Leu Pro Asp Val Phe Ile Arg Cys
1               5

<210> SEQ ID NO 109
<211> LENGTH: 9
<212> TYPE: PRT
<213> ORGANISM: Homo sapiens

<400> SEQUENCE: 109

His Leu Ser Thr Ala Phe Ala Arg Val
1               5

<210> SEQ ID NO 110
<211> LENGTH: 13
<212> TYPE: PRT
<213> ORGANISM: Homo sapiens

<400> SEQUENCE: 110

Cys Val Glu Trp Leu Arg Ile Tyr Leu Glu Asn Gly Lys
1               5                   10

<210> SEQ ID NO 111
<211> LENGTH: 9
<212> TYPE: PRT
<213> ORGANISM: Homo sapiens

<400> SEQUENCE: 111

Ser Leu Phe Glu Gly Ile Asp Ile Tyr
1               5

<210> SEQ ID NO 112
<211> LENGTH: 10
<212> TYPE: PRT
<213> ORGANISM: Homo sapiens

<400> SEQUENCE: 112

Tyr Ser Trp Met Asp Ile Ser Cys Trp Ile
1               5                   10

<210> SEQ ID NO 113
<211> LENGTH: 9
<212> TYPE: PRT
<213> ORGANISM: Homo sapiens

<400> SEQUENCE: 113

Ala Glu Pro Ile Asn Ile Gln Thr Val
1               5

<210> SEQ ID NO 114
<211> LENGTH: 9
<212> TYPE: PRT
<213> ORGANISM: Homo sapiens

<400> SEQUENCE: 114

Glu Glu Lys Leu Ile Val Val Leu Phe
1               5

<210> SEQ ID NO 115
<211> LENGTH: 10
<212> TYPE: PRT
```

<213> ORGANISM: Homo sapiens

<400> SEQUENCE: 115

Ser Glu Leu Phe Arg Ser Gly Leu Asp Tyr
1               5                   10

<210> SEQ ID NO 116
<211> LENGTH: 9
<212> TYPE: PRT
<213> ORGANISM: Homo sapiens

<400> SEQUENCE: 116

Phe Arg Ser Gly Leu Asp Ser Tyr Val
1               5

<210> SEQ ID NO 117
<211> LENGTH: 9
<212> TYPE: PRT
<213> ORGANISM: Homo sapiens

<400> SEQUENCE: 117

Glu Ala Phe Ile Gln Pro Ile Thr Arg
1               5

<210> SEQ ID NO 118
<211> LENGTH: 9
<212> TYPE: PRT
<213> ORGANISM: Homo sapiens

<400> SEQUENCE: 118

Lys Ile Asn Lys Asn Pro Lys Tyr Lys
1               5

<210> SEQ ID NO 119
<211> LENGTH: 10
<212> TYPE: PRT
<213> ORGANISM: Homo sapiens

<400> SEQUENCE: 119

Ser Pro Ser Ser Asn Arg Ile Arg Asn Thr
1               5                   10

<210> SEQ ID NO 120
<211> LENGTH: 9
<212> TYPE: PRT
<213> ORGANISM: Homo sapiens

<400> SEQUENCE: 120

Asp Tyr Ser Ala Arg Trp Asn Glu Ile
1               5

<210> SEQ ID NO 121
<211> LENGTH: 9
<212> TYPE: PRT
<213> ORGANISM: Homo sapiens

<400> SEQUENCE: 121

Ala Tyr Asp Phe Leu Tyr Asn Tyr Leu
1               5

<210> SEQ ID NO 122
<211> LENGTH: 9
<212> TYPE: PRT
<213> ORGANISM: Homo sapiens

```
<400> SEQUENCE: 122

Ser Tyr Thr Arg Leu Phe Leu Ile Leu
1               5

<210> SEQ ID NO 123
<211> LENGTH: 10
<212> TYPE: PRT
<213> ORGANISM: Homo sapiens

<400> SEQUENCE: 123

Glu Val Ile Ser Cys Lys Leu Ile Lys Arg
1               5                   10

<210> SEQ ID NO 124
<211> LENGTH: 9
<212> TYPE: PRT
<213> ORGANISM: Homo sapiens

<400> SEQUENCE: 124

Arg Val Ala Ala Leu Ala Arg Asp Ala
1               5

<210> SEQ ID NO 125
<211> LENGTH: 16
<212> TYPE: PRT
<213> ORGANISM: Homo sapiens

<400> SEQUENCE: 125

Asp Val Pro Lys Trp Ile Ser Ile Met Thr Glu Arg Ser Val Pro His
1               5                   10                  15

<210> SEQ ID NO 126
<211> LENGTH: 16
<212> TYPE: PRT
<213> ORGANISM: Homo sapiens

<400> SEQUENCE: 126

Trp Asn Arg Gln Leu Tyr Pro Glu Trp Thr Glu Ala Gln Arg Leu Asp
1               5                   10                  15

<210> SEQ ID NO 127
<211> LENGTH: 14
<212> TYPE: PRT
<213> ORGANISM: Homo sapiens

<400> SEQUENCE: 127

Leu Leu Lys Tyr Arg Ala Arg Glu Pro Val Thr Lys Ala Glu
1               5                   10

<210> SEQ ID NO 128
<211> LENGTH: 15
<212> TYPE: PRT
<213> ORGANISM: Homo sapiens

<400> SEQUENCE: 128

Thr Ser Tyr Val Lys Val Leu His His Met Val Lys Ile Ser Gly
1               5                   10                  15

<210> SEQ ID NO 129
<211> LENGTH: 14
<212> TYPE: PRT
<213> ORGANISM: Homo sapiens

<400> SEQUENCE: 129
```

```
Ala Glu Leu Val His Phe Leu Leu Lys Tyr Arg Ala Arg
1               5                   10
```

<210> SEQ ID NO 130
<211> LENGTH: 23
<212> TYPE: PRT
<213> ORGANISM: Homo sapiens

<400> SEQUENCE: 130

```
Arg Asn Gly Tyr Arg Ala Leu Met Asp Lys Ser Leu His Val Gly Thr
1               5                   10                  15

Gln Cys Ala Leu Thr Arg Arg
            20
```

<210> SEQ ID NO 131
<211> LENGTH: 12
<212> TYPE: PRT
<213> ORGANISM: Homo sapiens

<400> SEQUENCE: 131

```
Pro Gly Ser Thr Ala Pro Pro Ala His Gly Val Thr
1               5                   10
```

<210> SEQ ID NO 132
<211> LENGTH: 10
<212> TYPE: PRT
<213> ORGANISM: Homo sapiens

<400> SEQUENCE: 132

```
Val Leu Leu Lys Glu Phe Thr Val Ser Gly
1               5                   10
```

<210> SEQ ID NO 133
<211> LENGTH: 18
<212> TYPE: PRT
<213> ORGANISM: Homo sapiens

<400> SEQUENCE: 133

```
Pro Leu Pro Val Pro Gly Val Leu Leu Lys Glu Phe Thr Val Ser Gly
1               5                   10                  15

Asn Ile
```

<210> SEQ ID NO 134
<211> LENGTH: 18
<212> TYPE: PRT
<213> ORGANISM: Homo sapiens

<400> SEQUENCE: 134

```
Val Leu Leu Lys Glu Phe Thr Val Ser Gly Asn Ile Leu Thr Ile Arg
1               5                   10                  15

Leu Thr
```

<210> SEQ ID NO 135
<211> LENGTH: 18
<212> TYPE: PRT
<213> ORGANISM: Homo sapiens

<400> SEQUENCE: 135

```
Ala Ala Asp His Arg Gln Leu Gln Leu Ser Ile Ser Ser Cys Leu Gln
1               5                   10                  15

Gln Leu
```

```
<210> SEQ ID NO 136
<211> LENGTH: 15
<212> TYPE: PRT
<213> ORGANISM: Homo sapiens

<400> SEQUENCE: 136

Ile Leu Leu Gly Arg Met Ser Leu Phe Met Pro Glu Asp Thr Gly
1               5                   10                  15

<210> SEQ ID NO 137
<211> LENGTH: 13
<212> TYPE: PRT
<213> ORGANISM: Homo sapiens

<400> SEQUENCE: 137

Ser Leu Phe His Pro Glu Asp Thr Gly Gln Val Phe Gln
1               5                   10

<210> SEQ ID NO 138
<211> LENGTH: 15
<212> TYPE: PRT
<213> ORGANISM: Homo sapiens

<400> SEQUENCE: 138

Gln Val Phe Gln Val Ser His Ser Phe Pro His Pro Leu Tyr Asp
1               5                   10                  15

<210> SEQ ID NO 139
<211> LENGTH: 15
<212> TYPE: PRT
<213> ORGANISM: Homo sapiens

<400> SEQUENCE: 139

Asn Asp Leu Met Leu Leu Arg Leu Ser Glu Pro Ala Glu Leu Thr
1               5                   10                  15

<210> SEQ ID NO 140
<211> LENGTH: 13
<212> TYPE: PRT
<213> ORGANISM: Homo sapiens

<400> SEQUENCE: 140

Lys Lys Leu Gln Cys Val Gln Leu His Val Ile Ser Met
1               5                   10

<210> SEQ ID NO 141
<211> LENGTH: 15
<212> TYPE: PRT
<213> ORGANISM: Homo sapiens

<400> SEQUENCE: 141

Gly Val Leu Gln Gly Ile Thr Ser Met Gly Ser Glu Pro Cys Ala
1               5                   10                  15

<210> SEQ ID NO 142
<211> LENGTH: 15
<212> TYPE: PRT
<213> ORGANISM: Homo sapiens

<400> SEQUENCE: 142

Gln Asn Ile Leu Leu Ser Asn Ala Pro Leu Gly Pro Gln Phe Pro
1               5                   10                  15

<210> SEQ ID NO 143
<211> LENGTH: 15
```

```
<212> TYPE: PRT
<213> ORGANISM: Homo sapiens

<400> SEQUENCE: 143

Asp Tyr Ser Tyr Leu Gln Asp Ser Asp Pro Asp Ser Phe Gln Asp
1               5                   10                  15

<210> SEQ ID NO 144
<211> LENGTH: 13
<212> TYPE: PRT
<213> ORGANISM: Homo sapiens

<400> SEQUENCE: 144

Ser Tyr Leu Gln Asp Ser Asp Pro Asp Ser Phe Gln Asp
1               5                   10

<210> SEQ ID NO 145
<211> LENGTH: 21
<212> TYPE: PRT
<213> ORGANISM: Homo sapiens

<400> SEQUENCE: 145

Arg His Arg Pro Leu Gln Glu Val Tyr Pro Glu Ala Asn Ala Pro Ile
1               5                   10                  15

Gly His Asn Arg Glu
            20

<210> SEQ ID NO 146
<211> LENGTH: 11
<212> TYPE: PRT
<213> ORGANISM: Homo sapiens

<400> SEQUENCE: 146

Glu Ile Trp Arg Asp Ile Asp Phe Ala His Glu
1               5                   10

<210> SEQ ID NO 147
<211> LENGTH: 13
<212> TYPE: PRT
<213> ORGANISM: Homo sapiens

<400> SEQUENCE: 147

Leu Phe Met Asp Thr Leu Ser Phe Val Cys Pro Leu Cys
1               5                   10

<210> SEQ ID NO 148
<211> LENGTH: 13
<212> TYPE: PRT
<213> ORGANISM: Homo sapiens

<400> SEQUENCE: 148

Leu Phe Met Asp Ser Leu Asn Phe Val Cys Pro Trp Cys
1               5                   10

<210> SEQ ID NO 149
<211> LENGTH: 12
<212> TYPE: PRT
<213> ORGANISM: Homo sapiens

<400> SEQUENCE: 149

Phe Ser Trp Ala Met Asp Leu Asp Pro Lys Gly Ala
1               5                   10

<210> SEQ ID NO 150
```

```
-continued

<211> LENGTH: 15
<212> TYPE: PRT
<213> ORGANISM: Homo sapiens

<400> SEQUENCE: 150

Gly Glu Leu Ile Gly Ile Leu Asn Ala Ala Lys Val Pro Ala Asp
1               5                   10                  15

<210> SEQ ID NO 151
<211> LENGTH: 9
<212> TYPE: PRT
<213> ORGANISM: Homo sapiens

<400> SEQUENCE: 151

Phe Met Val Glu Leu Val Glu Gly Ala
1               5

<210> SEQ ID NO 152
<211> LENGTH: 9
<212> TYPE: PRT
<213> ORGANISM: Homo sapiens

<400> SEQUENCE: 152

Lys Leu Ser Glu Gln Glu Ser Leu Leu
1               5

<210> SEQ ID NO 153
<211> LENGTH: 9
<212> TYPE: PRT
<213> ORGANISM: Homo sapiens

<400> SEQUENCE: 153

Met Leu Thr Asn Ser Cys Val Lys Leu
1               5

<210> SEQ ID NO 154
<211> LENGTH: 9
<212> TYPE: PRT
<213> ORGANISM: Homo sapiens

<400> SEQUENCE: 154

Ser Ser Lys Ala Leu Gln Arg Pro Val
1               5

<210> SEQ ID NO 155
<211> LENGTH: 9
<212> TYPE: PRT
<213> ORGANISM: Homo sapiens

<400> SEQUENCE: 155

Ala Thr Gly Phe Lys Gln Ser Ser Lys
1               5

<210> SEQ ID NO 156
<211> LENGTH: 9
<212> TYPE: PRT
<213> ORGANISM: Homo sapiens

<400> SEQUENCE: 156

Lys Gln Ser Ser Lys Ala Leu Gln Arg
1               5

<210> SEQ ID NO 157
<211> LENGTH: 11
<212> TYPE: PRT
```

```
<213> ORGANISM: Homo sapiens

<400> SEQUENCE: 157

His Ser Ala Thr Gly Phe Lys Gln Ser Ser Lys
1               5                   10

<210> SEQ ID NO 158
<211> LENGTH: 9
<212> TYPE: PRT
<213> ORGANISM: Homo sapiens

<400> SEQUENCE: 158

Lys Gln Ser Ser Lys Ala Leu Gln Arg
1               5

<210> SEQ ID NO 159
<211> LENGTH: 9
<212> TYPE: PRT
<213> ORGANISM: Homo sapiens

<400> SEQUENCE: 159

Gly Phe Lys Gln Ser Ser Lys Ala Leu
1               5

<210> SEQ ID NO 160
<211> LENGTH: 9
<212> TYPE: PRT
<213> ORGANISM: Homo sapiens

<400> SEQUENCE: 160

Arg Ile Ala Glu Cys Ile Leu Gly Met
1               5

<210> SEQ ID NO 161
<211> LENGTH: 17
<212> TYPE: PRT
<213> ORGANISM: Homo sapiens

<400> SEQUENCE: 161

Glu Gly Ala Phe His Gly Asp Ala Glu Ala Leu Gln Arg Pro Val Ala
1               5                   10                  15

Ser

<210> SEQ ID NO 162
<211> LENGTH: 17
<212> TYPE: PRT
<213> ORGANISM: Homo sapiens

<400> SEQUENCE: 162

Ile Pro Leu Thr Ile Asn Lys Glu Glu Ala Leu Gln Arg Pro Val Ala
1               5                   10                  15

Ser

<210> SEQ ID NO 163
<211> LENGTH: 17
<212> TYPE: PRT
<213> ORGANISM: Homo sapiens

<400> SEQUENCE: 163

Ala Thr Gly Phe Lys Gln Ser Ser Lys Ala Leu Gln Arg Pro Val Ala
1               5                   10                  15

Ser
```

<210> SEQ ID NO 164
<211> LENGTH: 24
<212> TYPE: PRT
<213> ORGANISM: Homo sapiens

<400> SEQUENCE: 164

Leu Ile Val Val Ile Val His Ser Ala Thr Gly Phe Lys Gln Ser Ser
1               5                   10                  15

Lys Ala Leu Gln Arg Pro Val Ala
            20

<210> SEQ ID NO 165
<211> LENGTH: 25
<212> TYPE: PRT
<213> ORGANISM: Homo sapiens

<400> SEQUENCE: 165

Ile Val His Ser Ala Thr Gly Phe Lys Gln Ser Ser Lys Ala Leu Gln
1               5                   10                  15

Arg Pro Val Ala Ser Asp Phe Glu Pro
            20                  25

<210> SEQ ID NO 166
<211> LENGTH: 16
<212> TYPE: PRT
<213> ORGANISM: Homo sapiens

<400> SEQUENCE: 166

Thr Met Lys Gln Ile Cys Lys Lys Glu Ile Arg Arg Leu His Gln Tyr
1               5                   10                  15

<210> SEQ ID NO 167
<211> LENGTH: 15
<212> TYPE: PRT
<213> ORGANISM: Homo sapiens

<400> SEQUENCE: 167

Gly Gly Ala Pro Pro Val Thr Trp Arg Arg Ala Pro Ala Pro Gly
1               5                   10                  15

<210> SEQ ID NO 168
<211> LENGTH: 15
<212> TYPE: PRT
<213> ORGANISM: Homo sapiens

<400> SEQUENCE: 168

Trp Arg Arg Ala Pro Ala Pro Gly Ala Lys Ala Met Ala Pro Gly
1               5                   10                  15

<210> SEQ ID NO 169
<211> LENGTH: 25
<212> TYPE: PRT
<213> ORGANISM: Homo sapiens

<400> SEQUENCE: 169

Asn Ser Asn His Val Ala Ser Gly Ala Gly Glu Ala Ala Ile Glu Thr
1               5                   10                  15

Gln Ser Ser Ser Ser Glu Glu Ile Val
            20                  25

<210> SEQ ID NO 170
<211> LENGTH: 17
<212> TYPE: PRT

<213> ORGANISM: Homo sapiens

<400> SEQUENCE: 170

Glu Gly Ala Phe His Gly Asp Ala Glu Ala Leu Gln Arg Pro Val Ala
1               5                   10                  15

Ser

<210> SEQ ID NO 171
<211> LENGTH: 15
<212> TYPE: PRT
<213> ORGANISM: Homo sapiens

<400> SEQUENCE: 171

Ile Gly Arg Ile Ala Glu Cys Ile Leu Gly Met Asn Pro Ser Arg
1               5                   10                  15

<210> SEQ ID NO 172
<211> LENGTH: 9
<212> TYPE: PRT
<213> ORGANISM: Hepatitis C virus

<400> SEQUENCE: 172

Met Ser Thr Asn Pro Lys Pro Gln Lys
1               5

<210> SEQ ID NO 173
<211> LENGTH: 9
<212> TYPE: PRT
<213> ORGANISM: Hepatitis C virus

<400> SEQUENCE: 173

Met Ser Thr Asn Pro Lys Pro Gln Arg
1               5

<210> SEQ ID NO 174
<211> LENGTH: 10
<212> TYPE: PRT
<213> ORGANISM: Hepatitis C virus

<400> SEQUENCE: 174

Cys Gln Ile Val Gly Gly Val Tyr Leu Leu
1               5                   10

<210> SEQ ID NO 175
<211> LENGTH: 10
<212> TYPE: PRT
<213> ORGANISM: Hepatitis C virus

<400> SEQUENCE: 175

Tyr Leu Leu Pro Arg Arg Gly Pro Arg Leu
1               5                   10

<210> SEQ ID NO 176
<211> LENGTH: 9
<212> TYPE: PRT
<213> ORGANISM: Hepatitis C virus

<400> SEQUENCE: 176

Gly Pro Arg Leu Gly Val Arg Ala Thr
1               5

<210> SEQ ID NO 177
<211> LENGTH: 9
<212> TYPE: PRT

<213> ORGANISM: Hepatitis C virus

<400> SEQUENCE: 177

Arg Leu Gly Val Arg Ala Thr Arg Lys
1               5

<210> SEQ ID NO 178
<211> LENGTH: 9
<212> TYPE: PRT
<213> ORGANISM: Hepatitis C virus

<400> SEQUENCE: 178

Lys Thr Ser Glu Arg Ser Gln Pro Arg
1               5

<210> SEQ ID NO 179
<211> LENGTH: 9
<212> TYPE: PRT
<213> ORGANISM: Hepatitis C virus

<400> SEQUENCE: 179

Asn Glu Gly Leu Gly Trp Gly Ala Trp
1               5

<210> SEQ ID NO 180
<211> LENGTH: 9
<212> TYPE: PRT
<213> ORGANISM: Hepatitis C virus

<400> SEQUENCE: 180

Asn Glu Gly Cys Gly Trp Gly Ala Trp
1               5

<210> SEQ ID NO 181
<211> LENGTH: 9
<212> TYPE: PRT
<213> ORGANISM: Hepatitis C virus

<400> SEQUENCE: 181

Asp Leu Met Gly Tyr Ile Pro Leu Val
1               5

<210> SEQ ID NO 182
<211> LENGTH: 9
<212> TYPE: PRT
<213> ORGANISM: Hepatitis C virus

<400> SEQUENCE: 182

Leu Pro Gly Cys Ser Phe Ser Ile Phe
1               5

<210> SEQ ID NO 183
<211> LENGTH: 10
<212> TYPE: PRT
<213> ORGANISM: Hepatitis C virus

<400> SEQUENCE: 183

Leu Leu Ala Leu Leu Ser Cys Leu Thr Val
1               5                   10

<210> SEQ ID NO 184
<211> LENGTH: 9
<212> TYPE: PRT
<213> ORGANISM: Hepatitis C virus

```
<400> SEQUENCE: 184

Asn Ala Ser Arg Cys Trp Val Ala Met
1               5

<210> SEQ ID NO 185
<211> LENGTH: 10
<212> TYPE: PRT
<213> ORGANISM: Hepatitis C virus

<400> SEQUENCE: 185

Gln Leu Arg Arg His Ile Asp Leu Leu Val
1               5                   10

<210> SEQ ID NO 186
<211> LENGTH: 9
<212> TYPE: PRT
<213> ORGANISM: Hepatitis C virus

<400> SEQUENCE: 186

Gln Leu Phe Thr Phe Ser Pro Arg Arg
1               5

<210> SEQ ID NO 187
<211> LENGTH: 11
<212> TYPE: PRT
<213> ORGANISM: Hepatitis C virus

<400> SEQUENCE: 187

Ser Leu Leu Ala Pro Gly Ala Lys Gln Asn Val
1               5                   10

<210> SEQ ID NO 188
<211> LENGTH: 13
<212> TYPE: PRT
<213> ORGANISM: Hepatitis C virus

<400> SEQUENCE: 188

Pro Glu Arg Leu Ser Cys Arg Pro Leu Thr Asp Phe Asp
1               5                   10

<210> SEQ ID NO 189
<211> LENGTH: 13
<212> TYPE: PRT
<213> ORGANISM: Hepatitis C virus

<400> SEQUENCE: 189

Pro Glu Arg Leu Ala Ser Cys Arg Pro Leu Thr Asp Phe
1               5                   10

<210> SEQ ID NO 190
<211> LENGTH: 10
<212> TYPE: PRT
<213> ORGANISM: Hepatitis C virus

<400> SEQUENCE: 190

Arg Pro Leu Thr Asp Phe Asp Gln Gly Trp
1               5                   10

<210> SEQ ID NO 191
<211> LENGTH: 8
<212> TYPE: PRT
<213> ORGANISM: Hepatitis C virus

<400> SEQUENCE: 191
```

-continued

Tyr Pro Pro Lys Pro Cys Gly Ile
1               5

<210> SEQ ID NO 192
<211> LENGTH: 10
<212> TYPE: PRT
<213> ORGANISM: Hepatitis C virus

<400> SEQUENCE: 192

Cys Val Ile Gly Gly Ala Gly Asn Asn Thr
1               5                   10

<210> SEQ ID NO 193
<211> LENGTH: 8
<212> TYPE: PRT
<213> ORGANISM: Hepatitis C virus

<400> SEQUENCE: 193

Thr Ile Asn Tyr Thr Ile Phe Lys
1               5

<210> SEQ ID NO 194
<211> LENGTH: 10
<212> TYPE: PRT
<213> ORGANISM: Hepatitis C virus

<400> SEQUENCE: 194

Arg Met Tyr Val Gly Gly Val Glu His Arg
1               5                   10

<210> SEQ ID NO 195
<211> LENGTH: 9
<212> TYPE: PRT
<213> ORGANISM: Hepatitis C virus

<400> SEQUENCE: 195

Leu Leu Phe Leu Leu Leu Ala Asp Ala
1               5

<210> SEQ ID NO 196
<211> LENGTH: 9
<212> TYPE: PRT
<213> ORGANISM: Hepatitis C virus

<400> SEQUENCE: 196

Phe Leu Leu Leu Ala Asp Ala Arg Val
1               5

<210> SEQ ID NO 197
<211> LENGTH: 13
<212> TYPE: PRT
<213> ORGANISM: Hepatitis C virus

<400> SEQUENCE: 197

Leu Met Ala Leu Thr Leu Ser Pro Tyr Tyr Lys Arg Tyr
1               5                   10

<210> SEQ ID NO 198
<211> LENGTH: 8
<212> TYPE: PRT
<213> ORGANISM: Hepatitis C virus

<400> SEQUENCE: 198

Met Ala Leu Thr Leu Ser Pro Tyr
1               5

<210> SEQ ID NO 199
<211> LENGTH: 9
<212> TYPE: PRT
<213> ORGANISM: Hepatitis C virus

<400> SEQUENCE: 199

Tyr Ile Ser Trp Cys Leu Trp Trp Leu
1               5

<210> SEQ ID NO 200
<211> LENGTH: 9
<212> TYPE: PRT
<213> ORGANISM: Hepatitis C virus

<400> SEQUENCE: 200

Cys Ile Asn Gly Val Cys Trp Thr Val
1               5

<210> SEQ ID NO 201
<211> LENGTH: 9
<212> TYPE: PRT
<213> ORGANISM: Hepatitis C virus

<400> SEQUENCE: 201

Tyr Leu Val Thr Arg His Ala Asp Val
1               5

<210> SEQ ID NO 202
<211> LENGTH: 9
<212> TYPE: PRT
<213> ORGANISM: Hepatitis C virus

<400> SEQUENCE: 202

Leu Leu Cys Pro Ala Gly His Ala Val
1               5

<210> SEQ ID NO 203
<211> LENGTH: 10
<212> TYPE: PRT
<213> ORGANISM: Hepatitis C virus

<400> SEQUENCE: 203

Thr Leu Gly Phe Gly Ala Tyr Met Ser Lys
1               5                   10

<210> SEQ ID NO 204
<211> LENGTH: 9
<212> TYPE: PRT
<213> ORGANISM: Hepatitis C virus

<400> SEQUENCE: 204

Leu Gly Phe Gly Ala Tyr Met Ser Lys
1               5

<210> SEQ ID NO 205
<211> LENGTH: 10
<212> TYPE: PRT
<213> ORGANISM: Hepatitis C virus

<400> SEQUENCE: 205

Gly Ala Tyr Met Ser Lys Ala His Gly Val
1               5                   10

<210> SEQ ID NO 206
<211> LENGTH: 10
<212> TYPE: PRT
<213> ORGANISM: Hepatitis C virus

<400> SEQUENCE: 206

Thr Gly Ala Pro Val Thr Tyr Ser Thr Tyr
1               5                   10

<210> SEQ ID NO 207
<211> LENGTH: 10
<212> TYPE: PRT
<213> ORGANISM: Hepatitis C virus

<400> SEQUENCE: 207

Thr Gly Ser Pro Ile Thr Tyr Ser Thr Tyr
1               5                   10

<210> SEQ ID NO 208
<211> LENGTH: 9
<212> TYPE: PRT
<213> ORGANISM: Hepatitis C virus

<400> SEQUENCE: 208

Leu Ile Phe Cys His Ser Lys Lys Lys
1               5

<210> SEQ ID NO 209
<211> LENGTH: 9
<212> TYPE: PRT
<213> ORGANISM: Hepatitis C virus

<400> SEQUENCE: 209

His Ser Lys Lys Lys Cys Asp Glu Leu
1               5

<210> SEQ ID NO 210
<211> LENGTH: 10
<212> TYPE: PRT
<213> ORGANISM: Hepatitis C virus

<400> SEQUENCE: 210

Lys Leu Val Ala Leu Gly Ile Asn Ala Val
1               5                   10

<210> SEQ ID NO 211
<211> LENGTH: 9
<212> TYPE: PRT
<213> ORGANISM: Hepatitis C virus

<400> SEQUENCE: 211

Tyr Leu Val Ala Tyr Gln Ala Thr Val
1               5

<210> SEQ ID NO 212
<211> LENGTH: 8
<212> TYPE: PRT
<213> ORGANISM: Hepatitis C virus

<400> SEQUENCE: 212

Leu Ile Arg Leu Lys Pro Thr Leu
1               5

<210> SEQ ID NO 213
<211> LENGTH: 8

```
<212> TYPE: PRT
<213> ORGANISM: Hepatitis C virus

<400> SEQUENCE: 213

Thr Leu Thr His Pro Val Thr Lys
1               5

<210> SEQ ID NO 214
<211> LENGTH: 9
<212> TYPE: PRT
<213> ORGANISM: Hepatitis C virus

<400> SEQUENCE: 214

Val Leu Val Gly Gly Val Leu Ala Ala
1               5

<210> SEQ ID NO 215
<211> LENGTH: 9
<212> TYPE: PRT
<213> ORGANISM: Hepatitis C virus

<400> SEQUENCE: 215

His Met Trp Asn Phe Ile Ser Gly Ile
1               5

<210> SEQ ID NO 216
<211> LENGTH: 9
<212> TYPE: PRT
<213> ORGANISM: Hepatitis C virus

<400> SEQUENCE: 216

Ser Leu Met Ala Phe Thr Ala Ala Val
1               5

<210> SEQ ID NO 217
<211> LENGTH: 10
<212> TYPE: PRT
<213> ORGANISM: Hepatitis C virus

<400> SEQUENCE: 217

Leu Leu Phe Asn Ile Leu Gly Gly Trp Val
1               5                   10

<210> SEQ ID NO 218
<211> LENGTH: 9
<212> TYPE: PRT
<213> ORGANISM: Hepatitis C virus

<400> SEQUENCE: 218

Ile Leu Ala Gly Tyr Gly Ala Gly Val
1               5

<210> SEQ ID NO 219
<211> LENGTH: 10
<212> TYPE: PRT
<213> ORGANISM: Hepatitis C virus

<400> SEQUENCE: 219

Gly Val Ala Gly Ala Leu Val Ala Phe Lys
1               5                   10

<210> SEQ ID NO 220
<211> LENGTH: 9
<212> TYPE: PRT
<213> ORGANISM: Hepatitis C virus
```

```
<400> SEQUENCE: 220

Val Ala Gly Ala Leu Val Ala Phe Lys
1               5

<210> SEQ ID NO 221
<211> LENGTH: 9
<212> TYPE: PRT
<213> ORGANISM: Hepatitis C virus

<400> SEQUENCE: 221

Trp Met Asn Arg Leu Ile Ala Phe Ala
1               5

<210> SEQ ID NO 222
<211> LENGTH: 9
<212> TYPE: PRT
<213> ORGANISM: Hepatitis C virus

<400> SEQUENCE: 222

Asn His Asp Ser Pro Asp Ala Glu Leu
1               5

<210> SEQ ID NO 223
<211> LENGTH: 9
<212> TYPE: PRT
<213> ORGANISM: Hepatitis C virus

<400> SEQUENCE: 223

Ile Leu Asp Ser Phe Asp Pro Leu Val
1               5

<210> SEQ ID NO 224
<211> LENGTH: 10
<212> TYPE: PRT
<213> ORGANISM: Hepatitis C virus

<400> SEQUENCE: 224

Arg Glu Ile Ser Val Pro Ala Glu Ile Leu
1               5                   10

<210> SEQ ID NO 225
<211> LENGTH: 9
<212> TYPE: PRT
<213> ORGANISM: Hepatitis C virus

<400> SEQUENCE: 225

Ser Leu Thr Pro Pro His Ser Ala Lys
1               5

<210> SEQ ID NO 226
<211> LENGTH: 10
<212> TYPE: PRT
<213> ORGANISM: Hepatitis C virus

<400> SEQUENCE: 226

Arg Leu Ile Val Phe Pro Asp Leu Gly Val
1               5                   10

<210> SEQ ID NO 227
<211> LENGTH: 9
<212> TYPE: PRT
<213> ORGANISM: Hepatitis C virus

<400> SEQUENCE: 227
```

```
Arg Val Cys Glu Lys Met Ala Leu Tyr
1               5

<210> SEQ ID NO 228
<211> LENGTH: 9
<212> TYPE: PRT
<213> ORGANISM: Hepatitis C virus

<400> SEQUENCE: 228

Lys Ser Lys Lys Thr Pro Met Gly Phe
1               5

<210> SEQ ID NO 229
<211> LENGTH: 9
<212> TYPE: PRT
<213> ORGANISM: Hepatitis C virus

<400> SEQUENCE: 229

Gly Leu Gln Asp Cys Thr Met Leu Val
1               5

<210> SEQ ID NO 230
<211> LENGTH: 9
<212> TYPE: PRT
<213> ORGANISM: Hepatitis C virus

<400> SEQUENCE: 230

His Asp Gly Ala Gly Lys Arg Val Tyr
1               5

<210> SEQ ID NO 231
<211> LENGTH: 11
<212> TYPE: PRT
<213> ORGANISM: Hepatitis C virus

<400> SEQUENCE: 231

His Asp Gly Ala Gly Lys Arg Val Tyr Tyr Leu
1               5                   10

<210> SEQ ID NO 232
<211> LENGTH: 9
<212> TYPE: PRT
<213> ORGANISM: Hepatitis C virus

<400> SEQUENCE: 232

Val Gly Ile Tyr Leu Leu Pro Asn Arg
1               5

<210> SEQ ID NO 233
<211> LENGTH: 9
<212> TYPE: PRT
<213> ORGANISM: Human immunodeficiency virus type 1

<400> SEQUENCE: 233

Gly Ser Glu Glu Leu Arg Ser Leu Tyr
1               5

<210> SEQ ID NO 234
<211> LENGTH: 9
<212> TYPE: PRT
<213> ORGANISM: Human immunodeficiency virus type 1

<400> SEQUENCE: 234

Ile Ser Glu Arg Ile Leu Ser Thr Tyr
```

```
1               5

<210> SEQ ID NO 235
<211> LENGTH: 9
<212> TYPE: PRT
<213> ORGANISM: Human immunodeficiency virus type 1

<400> SEQUENCE: 235

Ile Leu Lys Asp Pro Val His Gly Val
1               5

<210> SEQ ID NO 236
<211> LENGTH: 9
<212> TYPE: PRT
<213> ORGANISM: Human immunodeficiency virus type 1

<400> SEQUENCE: 236

Ile Leu Lys Glu Pro Val His Gly Val
1               5

<210> SEQ ID NO 237
<211> LENGTH: 9
<212> TYPE: PRT
<213> ORGANISM: Human immunodeficiency virus type 1

<400> SEQUENCE: 237

Ser Leu Phe Asn Thr Val Ala Thr Leu
1               5

<210> SEQ ID NO 238
<211> LENGTH: 9
<212> TYPE: PRT
<213> ORGANISM: Human immunodeficiency virus type 1

<400> SEQUENCE: 238

Ser Leu Tyr Asn Thr Val Ala Thr Leu
1               5

<210> SEQ ID NO 239
<211> LENGTH: 9
<212> TYPE: PRT
<213> ORGANISM: Human immunodeficiency virus type 1

<400> SEQUENCE: 239

Thr Leu Asn Ala Trp Val Lys Val Val
1               5

<210> SEQ ID NO 240
<211> LENGTH: 9
<212> TYPE: PRT
<213> ORGANISM: Human immunodeficiency virus type 1

<400> SEQUENCE: 240

Thr Leu Asn Ala Trp Val Lys Val Ile
1               5

<210> SEQ ID NO 241
<211> LENGTH: 9
<212> TYPE: PRT
<213> ORGANISM: Human immunodeficiency virus type 1

<400> SEQUENCE: 241

Ala Leu Lys His Arg Ala Tyr Glu Leu
1               5
```

```
<210> SEQ ID NO 242
<211> LENGTH: 9
<212> TYPE: PRT
<213> ORGANISM: Human immunodeficiency virus type 1

<400> SEQUENCE: 242

Ala Phe His His Val Ala Arg Glu Leu
1               5

<210> SEQ ID NO 243
<211> LENGTH: 9
<212> TYPE: PRT
<213> ORGANISM: Human immunodeficiency virus type 1

<400> SEQUENCE: 243

Lys Ile Arg Leu Arg Pro Gly Gly Lys
1               5

<210> SEQ ID NO 244
<211> LENGTH: 11
<212> TYPE: PRT
<213> ORGANISM: Human immunodeficiency virus type 1

<400> SEQUENCE: 244

Arg Leu Arg Asp Leu Leu Leu Ile Val Thr Arg
1               5                   10

<210> SEQ ID NO 245
<211> LENGTH: 9
<212> TYPE: PRT
<213> ORGANISM: Human immunodeficiency virus type 1

<400> SEQUENCE: 245

Ser Ile Phe Gln Ser Ser Met Thr Lys
1               5

<210> SEQ ID NO 246
<211> LENGTH: 9
<212> TYPE: PRT
<213> ORGANISM: Human immunodeficiency virus type 1

<400> SEQUENCE: 246

Ala Ile Phe Gln Ser Ser Met Thr Lys
1               5

<210> SEQ ID NO 247
<211> LENGTH: 9
<212> TYPE: PRT
<213> ORGANISM: Human immunodeficiency virus type 1

<400> SEQUENCE: 247

Asp Leu Ser His Phe Leu Lys Glu Lys
1               5

<210> SEQ ID NO 248
<211> LENGTH: 10
<212> TYPE: PRT
<213> ORGANISM: Human immunodeficiency virus type 1

<400> SEQUENCE: 248

Gln Val Pro Leu Arg Pro Met Thr Tyr Lys
1               5                   10

<210> SEQ ID NO 249
```

```
<211> LENGTH: 9
<212> TYPE: PRT
<213> ORGANISM: Human immunodeficiency virus type 1

<400> SEQUENCE: 249

Ala Val Asp Leu Ser His Phe Leu Lys
1               5

<210> SEQ ID NO 250
<211> LENGTH: 10
<212> TYPE: PRT
<213> ORGANISM: Human immunodeficiency virus type 1

<400> SEQUENCE: 250

Ile Tyr Gln Glu Pro Phe Lys Asn Leu Lys
1               5                   10

<210> SEQ ID NO 251
<211> LENGTH: 9
<212> TYPE: PRT
<213> ORGANISM: Human immunodeficiency virus type 1

<400> SEQUENCE: 251

Thr Leu Tyr Cys Val His Gln Arg Ile
1               5

<210> SEQ ID NO 252
<211> LENGTH: 8
<212> TYPE: PRT
<213> ORGANISM: Human immunodeficiency virus type 1

<400> SEQUENCE: 252

Tyr Leu Arg Asp Gln Gln Leu Leu
1               5

<210> SEQ ID NO 253
<211> LENGTH: 8
<212> TYPE: PRT
<213> ORGANISM: Human immunodeficiency virus type 1

<400> SEQUENCE: 253

Tyr Leu Lys Asp Gln Gln Leu Leu
1               5

<210> SEQ ID NO 254
<211> LENGTH: 9
<212> TYPE: PRT
<213> ORGANISM: Human immunodeficiency virus type 1

<400> SEQUENCE: 254

Arg Tyr Leu Arg Asp Gln Gln Leu Leu
1               5

<210> SEQ ID NO 255
<211> LENGTH: 9
<212> TYPE: PRT
<213> ORGANISM: Human immunodeficiency virus type 1

<400> SEQUENCE: 255

Arg Tyr Leu Lys Asp Gln Gln Leu Leu
1               5

<210> SEQ ID NO 256
<211> LENGTH: 10
<212> TYPE: PRT
```

<213> ORGANISM: Human immunodeficiency virus type 1

<400> SEQUENCE: 256

Leu Phe Cys Ala Ser Asp Ala Lys Ala Tyr
1               5                   10

<210> SEQ ID NO 257
<211> LENGTH: 9
<212> TYPE: PRT
<213> ORGANISM: Human immunodeficiency virus type 1

<400> SEQUENCE: 257

Asp Ser Arg Leu Ala Phe His His Met
1               5

<210> SEQ ID NO 258
<211> LENGTH: 11
<212> TYPE: PRT
<213> ORGANISM: Human immunodeficiency virus type 1

<400> SEQUENCE: 258

Arg Asp Tyr Val Asp Arg Phe Phe Lys Thr Leu
1               5                   10

<210> SEQ ID NO 259
<211> LENGTH: 10
<212> TYPE: PRT
<213> ORGANISM: Human immunodeficiency virus type 1

<400> SEQUENCE: 259

Val Ser Phe Glu Pro Ile Pro Ile His Tyr
1               5                   10

<210> SEQ ID NO 260
<211> LENGTH: 9
<212> TYPE: PRT
<213> ORGANISM: Human immunodeficiency virus type 1

<400> SEQUENCE: 260

Asp Thr Val Leu Glu Asp Ile Asn Leu
1               5

<210> SEQ ID NO 261
<211> LENGTH: 10
<212> TYPE: PRT
<213> ORGANISM: Human immunodeficiency virus type 1

<400> SEQUENCE: 261

Glu Thr Ala Tyr Phe Tyr Ile Leu Lys Leu
1               5                   10

<210> SEQ ID NO 262
<211> LENGTH: 9
<212> TYPE: PRT
<213> ORGANISM: Human immunodeficiency virus type 1

<400> SEQUENCE: 262

Ile Thr Leu Trp Gln Arg Pro Leu Val
1               5

<210> SEQ ID NO 263
<211> LENGTH: 9
<212> TYPE: PRT
<213> ORGANISM: Human immunodeficiency virus type 1

-continued

```
<400> SEQUENCE: 263

Ile Pro Arg Arg Ile Arg Gln Gly Leu
1               5

<210> SEQ ID NO 264
<211> LENGTH: 10
<212> TYPE: PRT
<213> ORGANISM: Human immunodeficiency virus type 1

<400> SEQUENCE: 264

Thr Pro Gly Pro Gly Val Arg Tyr Pro Leu
1               5                   10

<210> SEQ ID NO 265
<211> LENGTH: 10
<212> TYPE: PRT
<213> ORGANISM: Human immunodeficiency virus type 1

<400> SEQUENCE: 265

Thr Pro Gly Pro Gly Ile Arg Tyr Pro Leu
1               5                   10

<210> SEQ ID NO 266
<211> LENGTH: 10
<212> TYPE: PRT
<213> ORGANISM: Human immunodeficiency virus type 1

<400> SEQUENCE: 266

Phe Pro Val Thr Pro Gln Val Pro Leu Arg
1               5                   10

<210> SEQ ID NO 267
<211> LENGTH: 9
<212> TYPE: PRT
<213> ORGANISM: Human immunodeficiency virus type 1

<400> SEQUENCE: 267

Ser Pro Arg Thr Leu Asn Ala Trp Val
1               5

<210> SEQ ID NO 268
<211> LENGTH: 9
<212> TYPE: PRT
<213> ORGANISM: Human immunodeficiency virus type 1

<400> SEQUENCE: 268

Gly Pro Lys Val Lys Gln Trp Pro Leu
1               5

<210> SEQ ID NO 269
<211> LENGTH: 8
<212> TYPE: PRT
<213> ORGANISM: Human immunodeficiency virus type 1

<400> SEQUENCE: 269

Tyr Leu Lys Asp Gln Gln Leu Leu
1               5

<210> SEQ ID NO 270
<211> LENGTH: 8
<212> TYPE: PRT
<213> ORGANISM: Human immunodeficiency virus type 1

<400> SEQUENCE: 270
```

```
Gly Gly Lys Lys Lys Tyr Arg Leu
1               5

<210> SEQ ID NO 271
<211> LENGTH: 9
<212> TYPE: PRT
<213> ORGANISM: Human immunodeficiency virus type 1

<400> SEQUENCE: 271

Asp Arg Phe Phe Lys Thr Leu Arg Ala
1               5

<210> SEQ ID NO 272
<211> LENGTH: 9
<212> TYPE: PRT
<213> ORGANISM: Human immunodeficiency virus type 1

<400> SEQUENCE: 272

Asp Arg Phe Trp Lys Thr Leu Arg Ala
1               5

<210> SEQ ID NO 273
<211> LENGTH: 9
<212> TYPE: PRT
<213> ORGANISM: Human immunodeficiency virus type 1

<400> SEQUENCE: 273

Asp Leu Asn Met Met Leu Asn Ile Val
1               5

<210> SEQ ID NO 274
<211> LENGTH: 9
<212> TYPE: PRT
<213> ORGANISM: Human immunodeficiency virus type 1

<400> SEQUENCE: 274

Asp Leu Asn Thr Met Leu Asn Val Val
1               5

<210> SEQ ID NO 275
<211> LENGTH: 9
<212> TYPE: PRT
<213> ORGANISM: Human immunodeficiency virus type 1

<400> SEQUENCE: 275

Glu Arg Tyr Leu Arg Asp Gln Gln Leu
1               5

<210> SEQ ID NO 276
<211> LENGTH: 9
<212> TYPE: PRT
<213> ORGANISM: Human immunodeficiency virus type 1

<400> SEQUENCE: 276

Arg Ala Glu Gln Ala Ser Gln Glu Val
1               5

<210> SEQ ID NO 277
<211> LENGTH: 9
<212> TYPE: PRT
<213> ORGANISM: Human immunodeficiency virus type 1

<400> SEQUENCE: 277

Tyr Pro Leu Thr Phe Gly Trp Cys Tyr
1               5
```

<210> SEQ ID NO 278
<211> LENGTH: 9
<212> TYPE: PRT
<213> ORGANISM: Human immunodeficiency virus type 1

<400> SEQUENCE: 278

Tyr Pro Leu Thr Phe Gly Trp Cys Phe
1               5

<210> SEQ ID NO 279
<211> LENGTH: 10
<212> TYPE: PRT
<213> ORGANISM: Human immunodeficiency virus type 1

<400> SEQUENCE: 279

Phe Arg Asp Tyr Val Asp Arg Phe Tyr Lys
1               5                   10

<210> SEQ ID NO 280
<211> LENGTH: 10
<212> TYPE: PRT
<213> ORGANISM: Human immunodeficiency virus type 1

<400> SEQUENCE: 280

Phe Arg Asp Tyr Val Asp Arg Phe Phe Lys
1               5                   10

<210> SEQ ID NO 281
<211> LENGTH: 10
<212> TYPE: PRT
<213> ORGANISM: Human immunodeficiency virus type 1

<400> SEQUENCE: 281

Lys Arg Trp Ile Ile Leu Gly Leu Asn Lys
1               5                   10

<210> SEQ ID NO 282
<211> LENGTH: 10
<212> TYPE: PRT
<213> ORGANISM: Human immunodeficiency virus type 1

<400> SEQUENCE: 282

Lys Arg Trp Ile Ile Met Gly Leu Asn Lys
1               5                   10

<210> SEQ ID NO 283
<211> LENGTH: 9
<212> TYPE: PRT
<213> ORGANISM: Human immunodeficiency virus type 1

<400> SEQUENCE: 283

Thr Ala Val Pro Trp Asn Ala Ser Trp
1               5

<210> SEQ ID NO 284
<211> LENGTH: 8
<212> TYPE: PRT
<213> ORGANISM: Human immunodeficiency virus type 1

<400> SEQUENCE: 284

Val Pro Leu Arg Pro Met Thr Tyr
1               5

```
<210> SEQ ID NO 285
<211> LENGTH: 9
<212> TYPE: PRT
<213> ORGANISM: Human immunodeficiency virus type 1

<400> SEQUENCE: 285

His Pro Asp Ile Val Ile Tyr Gln Tyr
1               5

<210> SEQ ID NO 286
<211> LENGTH: 9
<212> TYPE: PRT
<213> ORGANISM: Human immunodeficiency virus type 1

<400> SEQUENCE: 286

Asn Pro Asp Ile Val Ile Tyr Gln Tyr
1               5

<210> SEQ ID NO 287
<211> LENGTH: 9
<212> TYPE: PRT
<213> ORGANISM: Human immunodeficiency virus type 1

<400> SEQUENCE: 287

Pro Pro Ile Pro Val Gly Asp Ile Tyr
1               5

<210> SEQ ID NO 288
<211> LENGTH: 9
<212> TYPE: PRT
<213> ORGANISM: Human immunodeficiency virus type 1

<400> SEQUENCE: 288

Ile Pro Leu Thr Glu Glu Ala Glu Leu
1               5

<210> SEQ ID NO 289
<211> LENGTH: 9
<212> TYPE: PRT
<213> ORGANISM: Human immunodeficiency virus type 1

<400> SEQUENCE: 289

Asp Pro Asn Pro Gln Glu Val Val Leu
1               5

<210> SEQ ID NO 290
<211> LENGTH: 9
<212> TYPE: PRT
<213> ORGANISM: Human immunodeficiency virus type 1

<400> SEQUENCE: 290

Leu Pro Cys Arg Ile Lys Gln Ile Ile
1               5

<210> SEQ ID NO 291
<211> LENGTH: 9
<212> TYPE: PRT
<213> ORGANISM: Human immunodeficiency virus type 1

<400> SEQUENCE: 291

Ala Thr Gln Glu Val Lys Asn Trp Met
1               5

<210> SEQ ID NO 292
<211> LENGTH: 9
```

-continued

<212> TYPE: PRT
<213> ORGANISM: Human immunodeficiency virus type 1

<400> SEQUENCE: 292

Ala Ser Gln Glu Val Lys Asn Trp Met
1               5

<210> SEQ ID NO 293
<211> LENGTH: 10
<212> TYPE: PRT
<213> ORGANISM: Human immunodeficiency virus type 1

<400> SEQUENCE: 293

Asp Thr Ile Asn Glu Glu Ala Ala Glu Trp
1               5                   10

<210> SEQ ID NO 294
<211> LENGTH: 9
<212> TYPE: PRT
<213> ORGANISM: Human immunodeficiency virus type 1

<400> SEQUENCE: 294

Gln Ala Thr Gln Glu Val Lys Asn Trp
1               5

<210> SEQ ID NO 295
<211> LENGTH: 10
<212> TYPE: PRT
<213> ORGANISM: Human immunodeficiency virus type 1

<400> SEQUENCE: 295

Glu Val Lys Asn Trp Met Thr Glu Thr Leu
1               5                   10

<210> SEQ ID NO 296
<211> LENGTH: 10
<212> TYPE: PRT
<213> ORGANISM: Human immunodeficiency virus type 1

<400> SEQUENCE: 296

Thr Ser Thr Leu Gln Glu Gln Ile Gly Trp
1               5                   10

<210> SEQ ID NO 297
<211> LENGTH: 9
<212> TYPE: PRT
<213> ORGANISM: Human immunodeficiency virus type 1

<400> SEQUENCE: 297

Leu Ser Pro Arg Thr Leu Asn Ala Trp
1               5

<210> SEQ ID NO 298
<211> LENGTH: 9
<212> TYPE: PRT
<213> ORGANISM: Human immunodeficiency virus type 1

<400> SEQUENCE: 298

Ile Ser Pro Arg Thr Leu Asn Ala Trp
1               5

<210> SEQ ID NO 299
<211> LENGTH: 11
<212> TYPE: PRT
<213> ORGANISM: Human immunodeficiency virus type 1

<400> SEQUENCE: 299

Lys Ala Phe Ser Pro Glu Val Ile Pro Met Phe
1               5                   10

<210> SEQ ID NO 300
<211> LENGTH: 8
<212> TYPE: PRT
<213> ORGANISM: Human immunodeficiency virus type 1

<400> SEQUENCE: 300

Gln Ala Ile Ser Pro Arg Thr Leu
1               5

<210> SEQ ID NO 301
<211> LENGTH: 9
<212> TYPE: PRT
<213> ORGANISM: Human immunodeficiency virus type 1

<400> SEQUENCE: 301

Ser Phe Asn Cys Gly Gly Glu Phe Phe
1               5

<210> SEQ ID NO 302
<211> LENGTH: 9
<212> TYPE: PRT
<213> ORGANISM: Human immunodeficiency virus type 1

<400> SEQUENCE: 302

Lys Tyr Arg Leu Lys His Leu Val Trp
1               5

<210> SEQ ID NO 303
<211> LENGTH: 9
<212> TYPE: PRT
<213> ORGANISM: Human immunodeficiency virus type 1

<400> SEQUENCE: 303

Gln Ala Ser Gly Glu Val Lys Asn Trp
1               5

<210> SEQ ID NO 304
<211> LENGTH: 10
<212> TYPE: PRT
<213> ORGANISM: Hepatitis C virus

<400> SEQUENCE: 304

Cys Val Ile Gly Gly Ala Gly Asn Asn Thr
1               5                   10

<210> SEQ ID NO 305
<211> LENGTH: 9
<212> TYPE: PRT
<213> ORGANISM: Hepatitis C virus

<400> SEQUENCE: 305

Gly Pro Arg Leu Gly Val Arg Ala Thr
1               5

<210> SEQ ID NO 306
<211> LENGTH: 8
<212> TYPE: PRT
<213> ORGANISM: Hepatitis C virus

<400> SEQUENCE: 306

```
Gly Pro Arg Leu Gly Val Arg Ala
1               5

<210> SEQ ID NO 307
<211> LENGTH: 10
<212> TYPE: PR

```
<210> SEQ ID NO 314
<211> LENGTH: 365
<212> TYPE: PRT
<213> ORGANISM: Homo sapiens

<400> SEQUENCE: 314

Met Ala Val Met Ala Pro Arg Thr Leu Val Leu Leu Leu Ser Gly Ala
1               5                   10                  15
Leu Ala Leu Thr Gln Thr Trp Ala Gly Ser His Ser Met Arg Tyr Phe
            20                  25                  30
Phe Thr Ser Val Ser Arg Pro Gly Arg Gly Glu Pro Arg Phe Ile Ala
        35                  40                  45
Val Gly Tyr Val Asp Asp Thr Gln Phe Val Arg Phe Asp Ser Asp Ala
    50                  55                  60
Ala Ser Gln Arg Met Glu Pro Arg Ala Pro Trp Ile Glu Gln Glu Gly
65                  70                  75                  80
Pro Glu Tyr Trp Asp Gly Glu Thr Arg Lys Val Lys Ala His Ser Gln
                85                  90                  95
Thr His Arg Val Asp Leu Gly Thr Leu Arg Gly Tyr Tyr Asn Gln Ser
            100                 105                 110
Glu Ala Gly Ser His Thr Val Gln Arg Met Tyr Gly Cys Asp Val Gly
        115                 120                 125
Ser Asp Trp Arg Phe Leu Arg Gly Tyr His Gln Tyr Ala Tyr Asp Gly
    130                 135                 140
Lys Asp Tyr Ile Ala Leu Lys Glu Asp Leu Arg Ser Trp Thr Ala Ala
145                 150                 155                 160
Asp Met Ala Ala Gln Thr Thr Lys His Lys Trp Glu Ala Ala His Val
                165                 170                 175
Ala Glu Gln Leu Arg Ala Tyr Leu Glu Gly Thr Cys Val Glu Trp Leu
            180                 185                 190
Arg Arg Tyr Leu Glu Asn Gly Lys Glu Thr Leu Gln Arg Thr Asp Ala
        195                 200                 205
Pro Lys Thr His Met Thr His His Ala Val Ser Asp His Glu Ala Thr
    210                 215                 220
Leu Arg Cys Trp Ala Leu Ser Phe Tyr Pro Ala Glu Ile Thr Leu Thr
225                 230                 235                 240
Trp Gln Arg Asp Gly Glu Asp Gln Thr Gln Asp Thr Glu Leu Val Glu
                245                 250                 255
Thr Arg Pro Ala Gly Asp Gly Thr Phe Gln Lys Trp Ala Ala Val Val
            260                 265                 270
Val Pro Ser Gly Gln Glu Gln Arg Tyr Thr Cys His Val Gln His Glu
        275                 280                 285
Gly Leu Pro Lys Pro Leu Thr Leu Arg Trp Glu Pro Ser Ser Gln Pro
    290                 295                 300
Thr Ile Pro Ile Val Gly Ile Ile Ala Gly Leu Val Leu Phe Gly Ala
305                 310                 315                 320
Val Ile Thr Gly Ala Val Val Ala Ala Val Met Trp Arg Arg Lys Ser
                325                 330                 335
Ser Asp Arg Lys Gly Gly Ser Tyr Ser Gln Ala Ala Ser Ser Asp Ser
            340                 345                 350
Ala Gln Gly Ser Asp Val Ser Leu Thr Ala Cys Lys Val
        355                 360                 365
```

<210> SEQ ID NO 315
<211> LENGTH: 362
<212> TYPE: PRT
<213> ORGANISM: Homo sapiens

<400> SEQUENCE: 315

```
Met Leu Val Met Ala Pro Arg Thr Val Leu Leu Leu Ser Ala Ala
1               5                   10                  15

Leu Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Tyr Lys Ala Gln Ala Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly His Asp Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Arg Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360
```

<210> SEQ ID NO 316

<211> LENGTH: 266
<212> TYPE: PRT
<213> ORGANISM: Homo sapiens

<400> SEQUENCE: 316

Met Val Cys Leu Lys Leu Pro Gly Gly Ser Leu Ala Ala Leu Thr
1               5                   10                  15

Val Thr Leu Met Val Leu Ser Ser Arg Leu Ala Phe Ala Gly Asp Thr
            20                  25                  30

Arg Pro Arg Phe Leu Glu Leu Arg Lys Ser Glu Cys His Phe Phe Asn
        35                  40                  45

Gly Thr Glu Arg Val Arg Tyr Leu Asp Arg Tyr Phe His Asn Gln Glu
    50                  55                  60

Glu Phe Leu Arg Phe Asp Ser Asp Val Gly Glu Tyr Arg Ala Val Thr
65                  70                  75                  80

Glu Leu Gly Arg Pro Val Ala Glu Ser Trp Asn Ser Gln Lys Asp Leu
                85                  90                  95

Leu Glu Gln Lys Arg Gly Arg Val Asp Asn Tyr Cys Arg His Asn Tyr
            100                 105                 110

Gly Val Gly Glu Ser Phe Thr Val Gln Arg Arg Val His Pro Gln Val
        115                 120                 125

Thr Val Tyr Pro Ala Lys Thr Gln Pro Leu Gln His His Asn Leu Leu
130                 135                 140

Val Cys Ser Val Ser Gly Phe Tyr Pro Gly Ser Ile Glu Val Arg Trp
145                 150                 155                 160

Phe Arg Asn Gly Gln Glu Glu Lys Ala Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
        195                 200                 205

Val Thr Ser Ala Leu Thr Val Glu Trp Arg Ala Arg Ser Glu Ser Ala
    210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Gln Pro Thr Gly Phe Leu Ser
            260                 265

<210> SEQ ID NO 317
<211> LENGTH: 254
<212> TYPE: PRT
<213> ORGANISM: Homo sapiens

<400> SEQUENCE: 317

Met Ile Leu Asn Lys Ala Leu Leu Leu Gly Ala Leu Ala Leu Thr Thr
1               5                   10                  15

Val Met Ser Pro Cys Gly Gly Glu Asp Ile Val Ala Asp His Val Ala
            20                  25                  30

Ser Tyr Gly Val Asn Leu Tyr Gln Ser Tyr Gly Pro Ser Gly Gln Tyr
        35                  40                  45

Thr His Glu Phe Asp Gly Asp Glu Gln Phe Tyr Val Asp Leu Gly Arg
    50                  55                  60

Lys Glu Thr Val Trp Cys Leu Pro Val Leu Arg Gln Phe Arg Phe Asp
65                  70                  75                  80

-continued

```
Pro Gln Phe Ala Leu Thr Asn Ile Ala Val Thr Lys His Asn Leu Asn
            85                      90                  95

Ile Leu Ile Lys Arg Ser Asn Ser Thr Ala Ala Thr Asn Glu Val Pro
            100                 105                 110

Glu Val Thr Val Phe Ser Lys Ser Pro Val Thr Leu Gly Gln Pro Asn
            115                 120                 125

Thr Leu Ile Cys Leu Val Asp Asn Ile Phe Pro Pro Val Val Asn Ile
            130                 135                 140

Thr Trp Leu Ser Asn Gly His Ser Val Thr Glu Gly Val Ser Glu Thr
145             150                 155                 160

Ser Phe Leu Ser Lys Ser Asp His Ser Phe Phe Lys Ile Ser Tyr Leu
            165                 170                 175

Thr Phe Leu Pro Ser Ala Asp Glu Ile Tyr Asp Cys Lys Val Glu His
            180                 185                 190

Trp Gly Leu Asp Glu Pro Leu Leu Lys His Trp Glu Pro Glu Ile Pro
            195                 200                 205

Ala Pro Met Ser Glu Leu Thr Glu Thr Val Val Cys Ala Leu Gly Leu
            210                 215                 220

Ser Val Gly Leu Val Gly Ile Val Val Gly Thr Val Phe Ile Ile Arg
225             230                 235                 240

Gly Leu Arg Ser Val Gly Ala Ser Arg His Gln Gly Pro Leu
            245                 250
```

COMPOSITION FOR INDUCING IMMUNE RESPONSE COMPRISING INVERTED MICROSOMES

CROSS-REFERENCE TO RELATED APPLICATIONS

This application is the U.S. National Stage filing of International Application Serial No. PCT/GB2004/003285 filed Jul. 30, 2004, which claims priority to GB 0318096.5 filed Aug. 1, 2003, each of which is incorporated herein by reference in its entirety.

The present invention relates to a novel peptide-based vaccines, uses of such vaccines in prophylactic and therapeutic treatment of human and animal diseases, such as viral infection and cancer.

Most of the successful vaccines depend on neutralising antibodies raised by classic attenuated or killed pathogens. However, for pathogens causing chronic infection—such as HIV, hepatitis C virus, mycobacteria and parasites—or in the case of cancer, a T-cell mediated immune response is crucial. Molecular understanding of MHC antigen presentation and the T-cell immune responses led to the use of defined antigenic peptide plus cytokines and/or co-stimulatory molecules in attempts to develop vaccines. One of the basic problems in all these attempts was the difficulty to reconstitute an antigen delivery system that is qualitatively and quantitatively similar to antigen presenting cells (APC) in vivo.

CD8+ cytotoxic T lymphocytes (CTL) recognise antigens as small antigenic peptides that assemble with major histocompatibility complex (MHC) class I molecules. The antigenic peptides are generated in the cytosol of APC and subsequently translocated into the lumen of the endoplasmic reticulum (ER) (Rock, K. L. & Goldberg, A. L. *Annu Rev Immunol* 17, 739-779 (1999)). The MHC class I heavy chain is synthesised and inserted into the lumen of the ER and where it forms a dimer with b2-microglobulin (b2M) (Natarajan et al *Rev Immunogenet* 1, 32-46 (1999); Pamer E, & Cresswell P, *Annu Rev Immunol.* 16 323-358 (1998)). The dimers are retained in the ER until they assemble with proper antigenic peptides. The process of MHC class I dimer and assembly with peptides in the ER is catalysed by chaperones such as BIP, calnexin, calreticulin, and Erp57 (Paulsson K, & Wang P., *Biochim Biophys Acta.* 1641(1) 1-12 (2003)).

The assembled MHC class I are rapidly expressed on the cell surface of APC, such as infected or malignant cells. The recognition of peptide-MHC class I by T cell receptor leads the CTL to kill target cells expressing infectious or tumor antigens.

Following the identification of CTL recognized epitopes from viral or cancer proteins, synthetic peptide-based vaccines designed to elicit T-cell immunity became an attractive approach to the prevention or treatment of infectious and malignant diseases (Furman M H, & Ploegh H L., *J Clin Invest.* 110 (7) 875-9 (2002); Berinstein N. *Semin Oncol.* 30 (3) (Suppl 8), 1-8 (2003); Falk et al *Nature* 348, 248-251. (1990); (Van Bleek G M, & Nathenson S G., *Nature* 348: 213-216 (1990); Kast, W. M., & Melief, C. J. *Immunol. Lett.* 30:229-232 (1991)). There are a number of different forms of peptide vaccines based on these delivery systems. The simplest form is peptides dissolved in aqueous solutions. Direct injection of soluble antigenic peptides was shown to be unsuccessful at stimulating CTL responses, either because of their rapid biodegradation or induction of T cell energy resulting from the antigenic stimulation by immature APC (Kyburz, D. et al. *Eur. J. Immunol.* 23:1956-1962 (1993); Toes, R. E et al *Proc. Natl. Acad. Sci. USA.* 93:7855-7860 (1996); Amoscato et al *J. Immunol.* 161, 4023-4032 (1998)). An additional complication reported from the use of synthetic peptide-derived vaccines is the induction of CTLs that, while they are capable of killing target cells that are exogenously pulsed with peptide, they are not able to recognise target cells that naturally process and present the peptide epitope, such as infected or malignant cells (Dutoit, V. et al. *J. Clin. Invest.* 110:1813-1822 (2002)).

It has been reported that MHC class I antigen presentation is qualitatively controlled in the ER for selecting correct peptides. Only the correctly assembled MHC class I could express on the surface of APC. The use of adjuvants did little to increase the presentation quality of synthetic peptides (Schijns, V. E. 2001. *Crit. Rev. Immunol.* 21:75-85 (2001). An improved version of the peptide-vaccine has been constructed as an artificial lipo-membrane (BenMohamed et al *Lancet Infect Dis.* 2(7), 425-31 (2002)) with peptide-loaded recombinant MHC class I. Although liposome strategy is able to incorporate peptide bound MHC class I molecules in the lipid membrane before injection into patients, the sophisticated loading system in the ER of APC could not be easily imitated by a simple mixture of recombinant MHC class I, synthetic peptide and liposomes. Only a few peptides would assemble with recombinant MHC class I in vitro (Ostergaard Pedersen L, et al *Eur J Immunol.* 31(10), 2986-96 (2001).

In addition, the incorrect orientation of inserted MHC class I and lack of co-stimulatory molecules made it difficult to induce effective immune responses. Since the professional APCs have the unique ability of presenting optimal antigen and for initiating a cellular immune response by naïve T cells, strategies are being developed to generate autologous dendritic cells (DC), a key APC, as vaccine vehicles ex vivo (Banchereau, J. et al. *Annu. Rev. Immunol.* 18:767-811 (2000)). Initial studies showed that antigenic peptide-pulsed DC used as vaccines in vivo could induce a CTL response (Tsai, V. et al. *J. Immunol.* 158:1796-1802 (1997)). Despite the positive evidence reported from a number of human clinical trials, there is no biochemical evidence showing that the pulsed peptides are indeed loaded on the surface MHC class I, which questions the efficiency of peptide-pulsed APCs to induce effective immune responses.

There is therefore a need for a vaccine preparation that can overcome these problems and present a therapeutically effective alternative to conventional vaccines. Such vaccines should achieve the quality of the endogenous presented antigen by APC cells while preserving high efficacy and avoiding side effects.

According to a first aspect of the invention, there is provided a vaccine composition comprising isolated inverted microsomes from an animal cell, or membrane fragments thereof, in association with an externally disposed peptide antigen and a protein of the Major Histocompatibility Complex (MHC).

The microsomes of the present invention are derived from an animal cell and may therefore arise from the following compartments present in a eukaryotic cell: endoplasmic reticulum, lysosome; endosome, or components of the endocytic pathway.

The microsome may be isolated with a protein of the MHC already present in the membrane of the microsome or of the fragment. Alternatively, the MHC protein can be introduced into the microsome or fragment subsequently. The ER derived microsomes contain both MHC class I and class II molecules (Bryant et al *Adv Immunol.* 80, 71-114 (2002)).

The present invention is equally applicable with respect to the MHC class I restricted antigenic peptides as well as the MHC class II molecules. The protein of the MHC in the composition may be from a heterologous source with respect to the cell from which the microsomes are obtained.

The MHC family of proteins are encoded by the clustered genes of the major histocompatibility complex (MHC). MHC molecules are expressed on the cells of all higher vertebrates. They were first demonstrated in mice and called H-2 antigens (histocompatibility-2 antigens). In humans they are called HLA antigens (human-leucocyte-associated antigens) because they were first demonstrated on leucocytes (white blood cells). Class I and class II MHC molecules are the most polymorphic proteins known—that is, they show the greatest genetic variability from one individual to another—and they play a crucial role in presenting foreign protein antigens to cytotoxic and helper T cells, respectively. Whereas class I molecules are expressed on almost all vertebrate cells, class II molecules are restricted to a few cell types that interact with helper T cells, such as B lymphocytes and macrophages. Both classes of MHC molecules have immunoglobulin-like domains and a single peptide-binding groove, which binds small peptide fragments derived from foreign proteins. Each MHC molecule can bind a large and characteristic set of peptides, which are produced intracellularly by protein degradation. After they form inside the target cell, the peptide-MHC complexes are transported to the cell surface, where they are recognized by T cell receptors. In addition to their antigen-specific receptors that recognize peptide-MHC complexes on the surface of target cells, T cells express CD4 or CD8 co-receptors, which recognize non-polymorphic regions of MHC molecules on the target cell: helper cells express CD4, which recognizes class II MHC molecules, while cytotoxic T cells express CD8, which recognizes class I MHC molecules. (Alberts et al, "*Molecular Biology of the Cell*", 3rd edition, 1229-1235 (1994)).

The MHC class I consists of heavy chain and Beta-2-microglobulin. Human MHC class I heavy chains are encoded by three separate genetic loci called HLA A, B, C. They are noncovalently associated with a small protein called beta-2-microglobulin. An example of a human MHC class I protein is HLA class I histocompatibility antigen, A-2 alpha chain precursor (MHC class I antigen A*2) is shown in FIG. 13 (database accession no. P01892); or HLA class I histocompatibility antigen, B-7 alpha chain precursor (MHC class I antigen B*7) as shown in FIG. 13 (database accession no. P01889).

MHC class II are composed of two noncovalently bonded chains an α-chain and an β-chain. Both chains are coded by genes in I-region associated (Ia) antigens. Examples of such proteins are HLA class II histocompatibility antigen, DRB3-1 beta chain precursor (MHC class I antigen DRB3*1) shown in FIG. 14 (database accession no. P79483); and MHC class II histocompatibility antigen HLA-DQ alpha 1 (DQw4 specificity) precursor, also shown in FIG. 14 (database accession A37044).

The sequences of the MHC class I and II cDNAs and genomic DNAs are published and available.

All eucaryotic cells have an endoplasmic reticulum (ER). Its membrane typically constitutes more than half of the total membrane of an average animal cell. It is organized into a netlike labyrinth of branching tubules and flattened sacs extending throughout the cytosol. The tubules and sacs are all thought to interconnect, so that the ER membrane forms a continuous sheet enclosing a single internal space. This highly convoluted space is called the ER lumen or the ER cisternal space, and it often occupies more than 10% of the total cell volume. The ER membrane separates the ER lumen from the cytosol, and it mediates the selective transfer of molecules between these two compartments.

The ER plays a central part in lipid and protein biosynthesis. Its membrane is the site of production of all the transmembrane proteins and lipids for most of the cell's organelles, including the ER itself, the Golgi apparatus, lysosomes, endosomes, secretory vesicles, and the plasma membrane. The ER membrane also makes a major contribution to mitochondrial and peroxisomal membranes by producing most of their lipids. In addition, almost all of the proteins that will be secreted to the cell exterior—as well as those destined for the lumen of the ER, Golgi apparatus, or lysosomes—are initially delivered to the ER lumen (Alberts et al, "*Molecular Biology of the Cell*", 3rd edition, 577-595 (1994)).

The lysosome is a specialised organelle containing specialised enzymes for the degradation of internal cellular proteins that are required to be destroyed, or for the destruction of external foreign proteins or parasites that have been targeted for destruction by the immune system.

The endosome is a cell organelle that forms part of the endocytic pathway in the cell. There is a constant flow of endocytic vesicles that flow from the cell surface to the endosome or to the lysosome. The vesicles form by a process of "budding-off" from the external plasma membrane, known as invagination, or the vesicles can form from the internal cell organelles to which they ultimately return. Endocytosis is the process by which a cell internalises external receptors with or without bound ligand and also one way by which the cell can sample its external environment.

Compositions in accordance with the present invention may be optionally formulated with an appropriate adjuvant, and/or cytokines that promote T-cell responses, such as an interferon or an interleukin, e.g. IL-2, IL-15, IL-6, GM-CSF, IFNγ, other cytokines promoting T-cell responses, and/or conventional adjuvant. These can be suitably mixed with the microsomes loaded with antigen prior to administration, or may be suitably prepared as membrane-bound constituents of the microsomes.

Microsomes in the context of the present invention are the cell free membrane vesicles of the endoplasmic reticulum (ER), lysosomal, or endosomal compartments of any animal cell able to present antigenic peptide by means of the Major Histocompatibility Complex (MHC). The definition of ER-derived microsomes is based on the presence of so-called "ER-markers" which are proteins normally resident in the ER, such as BIP, p58, calnexin, calreticulin, tapasin. The definition of a lysosomal-derived microsome is based on the presence of the specific markers LAMP1 and/or LAMP2. Microsomes are recognised as such by their morphology as seen under the electron microscope following preparation from an animal cell.

The microsomes contained in a composition of the present invention can be isolated by any convenient means. Suitable methods include those of Saraste et al and/or Knipe et al (Saraste et al *Proc. Natl. Acad. Sci. U.S.A.* 83, 6425-6429 (1986) and Knipe et al *J. Virol.* 21, 1128-1139 (1977)). Such methods comprise homogenisation of cells or tissues, followed by separation of the cell nucleus by centrifugation at 7500 rpm for 10 minutes, then recovering the "rough" microsomes by centrifugation at 15500 rpm for 54 minutes. "Rough" microsomes are microsomes that have ribosomes attached. The resuspended "rough" microsomes are then further purified by centrifugation through a sucrose cushion for differential centrifugation at 110,000 g for 60 minutes. The rough microsomes were subfractionated by further centrifugation at 37,000 rpm for 10 hours on a sucrose gradient (to reach isopyknic conditions), and the ER containing fractions determined by Western blotting with appropriate antibody, for example anti-p58 antibody.

Inverted microsomes are the result of further processing, e.g. repeated freeze-thaw process steps, carried out on isolated microsomes which causes the disruption and reformation of the external membrane of the microsome such that the "inside" face of the membrane is presented on the "outside" of the inverted microsome. The microsomes that result from such processing are therefore described as "inside-out" or "inverted" microsomes. The process of preparing the "inside-out" or inverted microsomes results in the absence of the lumen structure seen in ordinary microsome preparations.

In compositions according to the present invention, the microsome may comprise a membrane fragment thereof. Suitably, such membrane fragments may be prepared by the method comprising the use of detergents or repeated freeze-thawing or sonication to break the microsome structure. Such fragments may also be similarly loaded with peptide antigen to form a composition of the present invention. Preferably, the membrane fragments are derived from intracellular membranes with markers specific to the ER or to the lysosomes.

In a vaccine composition of the present invention, there may also be a percentage of microsomes with a non-inverted structure, i.e. a membrane orientation that corresponds to the in situ arrangement after standard microsome preparation with an "inside" corresponding to the lumen of the ER, endosome or lysosome prior to microsome preparation. However, at least about 75% to about 95%, suitably at least about 90% of microsomes in the vaccine compositions of the invention have a reversed membrane orientation to in situ microsomes and are therefore described as being "inside-out" or inverted microsomes. The compositions may therefore additionally comprise a percentage of non-inverted microsomes.

In other embodiments of the invention, the composition may be more homogenous, and so may comprise at least about 95%, 96%, 97%, 98%, 99% or 100% of microsomes having an inverted or reversed (or "inside-out") membrane orientation compared to microsomes prepared from cells without further processing.

The microsomes may be loaded with antigen first and then subjected to further processing so as to provide inverted or "inside-out" microsomes thus exposing the inner surface of the ER membrane, or the microsomes can be prepared from a cell source where the preferred antigen peptide is already present in the microsomes, or the microsomes may be processed to provide inverted or "inside-out" microsomes first and then subsequently loaded with antigen.

Lysosomes and endosomes can be prepared by an equivalent procedure. Lysosomal microsomes which are purified from the endocytotic compartment of the animal cell include both lysosomes and endosomes. After fractionation of the total cellular membranes in the purification procedure for the preparation of ER-derived microsomes, the lysosomal membranes are defined by antibodies to its markers LAMP1 and LAMP2.

The purified lysosomal microsomes are then processed to yield inverted or "inside-out" microsomes or membrane fragments as described above which, if necessary, can then be loaded with MHC restricted peptides under acid conditions, such as for example at a pH of less then pH3, preferably from pH 3 to pH 3, suitably at around pH 2.5.

The animal cell from which the isolated microsome population is to be prepared can be any generally convenient cell type that has MHC molecules expressed by the cell. For example, cells of the blood or of the immune system such as, B-cells and macrophages, the so-called antigen presenting cells (APCs). However, cell types could also be used from tissues such as liver, kidney, lung, brain, heart, skin, bone marrow, pancreas etc.

The cells may be of a human or of a non-human animal. Suitably, the animal is a mammal. The animal may be a rodent species, e.g. a mouse, a rat or a guinea pig, or another species such as rabbit, or a canine or feline, or an ungulate species such as ovine, porcine, equine, caprine, bovine, or a non-mammalian animal species, e.g. an avian (such as poultry, e.g. chicken or turkey).

The cells from which the microsomes are prepared may be a cell line in culture. The cell line may be an immortalised cell line. The cell line may be ultimately derived from a non-embryonic tissue source.

In certain embodiments of the invention, the source of cells may be a genetically modified source of animal cells, such as a cell line, or a transgenic non-human animal. The cells or tissue from which the microsomes are prepared may be a humanised animal tissue or cell from a transgenic non-human animal whose genome has been modified by the insertion of one or more human genes.

In embodiments of the invention relating to microsomes prepared from a transgenic non-human animal or transgenic cell line, the transgenesis is the introduction of an additional gene or genes or protein-encoding nucleic acid sequence or sequences. The transgene may be a heterologous gene or an additional copy of a homologous gene, optionally under the control of a constitutive promoter or an inducible promoter. The transgenesis may be transient or stable transfection of a cell or a cell line, or an episomal expression system in a cell or a cell line.

However, it is in the field of human medicine, in which the compositions of this aspect of the invention are expected to find greatest application as vaccines. It is therefore preferred that the source of cells from which the microsomes are prepared has an MHC allotype that is compatible to the MHC of the recipient of the composition when used as a vaccine.

In one embodiment according to this aspect of the invention, the source of cells from which the microsomes are prepared may be the ultimate recipient of the composition when used as a vaccine.

Alternatively, a suitable source of human cells may be from a cell line, for example a non-embryo derived cell-line, suitably a B-cell line such as cell line 221. Such cell lines may also advantageously not express proteins of the Major Histocompatibility Complex (MHC) type class I and/or class II. This embodiment of the invention may be a more preferred embodiment for the manufacture of vaccines on a commercial scale, where non-individual vaccines are produced from such cell lines which have been engineered with different MHC allotypes.

Cell line 221 is an example of such a MHC negative cell line. The absence of a native MHC class I expression in such cells permits the modification of the cell line to express MHC class I of any desired genotype. This may be particularly important in achieving the full immunising effects of the vaccine composition, since different human populations express different MHC proteins. In such compositions of the invention, the MHC protein may therefore be of a heterologous source with respect to the cell from which the microsomes are obtained.

Some of the MHC class I, like HLA A2, are expressed in more than 20% of the population. In circumstances where a MHC negative cell line is used, one or more than one compatible MHC gene is transfected into the cell line by means of conventional gene transfer methods and the transgene is constructed into a expression vector. The expression cassette of expression construct normally includes standard promoter, such as CMV promoter, or elongation factor I promoter or actin promoter, enhancer, inserted transgene and the poly-A signal to achieve optimal expression. Before transfection, the expression cassette will be isolated from the plasmid backbone to avoid the expression of bacterial plasmid genes in transfected cells. The sequences of the MHC class I and II cDNAs and genomic DNAs are published and available. A MHC class I transfectants Bank can be constructed by using MHC class I negative or selected MHC class positive cell lines to transfect most of the MHC class I genes, respectively. The selection of the expression cassette will be dependent on the optimal expression of the transgene.

Transfection of the antigen presenting cells may be achieved using standard recombinant techniques, e.g. using a suitable vector comprising a nucleic acid sequence encoding a MHC protein of interest. The term "vector" generally refers to any nucleic acid vector which may be RNA, DNA or cDNA. The vector can be described alternatively as an "expression vector".

The terms "vector" or "expression vector" may include, among others, chromosomal, episomal, and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host may be used for expression in this regard. The vector may be constructed from a bacterial plasmid, for example the bacterial plasmid pUC18.

The vector may provide for specific expression. Such specific expression may be inducible expression or expression only in certain types of cells or both inducible and cell-specific. Preferred among inducible vectors are vectors that can be induced for expression by environmental factors that are easy to manipulate, such as temperature, nutrient additives, hypoxia and/or the presence of cytokines or other biologically active factors. Particularly preferred among inducible vectors are vectors that can be induced for expression by changes in the levels of chemicals, for example, chemical additives such as antibiotics. A variety of vectors suitable for use in the invention, including constitutive and inducible expression vectors for use in prokaryotic and eukaryotic hosts, are well known and employed routinely by those skilled in the art.

Recombinant expression vectors will include, for example, origins of replication, a promoter preferably derived from a highly expressed gene to direct transcription of a structural sequence, and a selectable marker to permit isolation of vector containing cells after exposure to the vector.

Mammalian expression vectors may comprise an origin of replication, a suitable promoter and enhancer, and also any necessary ribosome binding sites, polyadenylation regions, splice donor and acceptor sites, transcriptional termination sequences, and 5'-flanking non-transcribed sequences that are necessary for expression. Preferred mammalian expression vectors according to the present invention may be devoid of enhancer elements.

The promoter sequence may be any suitable known promoter, for example the human cytomegalovirus (CMV) promoter, the CMV immediate early promoter, the HSV thymidine kinase promoter, the early and late SV40 promoters or the promoters of retroviral LTR's, such as those of the Rous sarcoma virus ("RSV"), and metallothionein promoters, such as the mouse metallothionein-I promoter. The promoter may comprise the minimum sequence required for promoter activity (such as a TATA box without enhancer elements), for example, the minimal sequence of the CMV promoter (mCMV). Preferably the promoter is a mammalian promoter that can function at a low basal level devoid of an enhancer element.

Preferably, the promoter is contiguous to the nucleic acid sequence encoding the MHC protein to be transfected into the antigen presenting cell. It is contemplated that variants, for example, homologues or orthologues, of the promoters described herein are part of the present invention.

The backbone of the expression vector of the first aspect of the invention may be derived from a vector devoid of its own promoter and enhancer elements, for example the plasmid vector pGL2. Enhancers are able to bind to promoter regions situated several thousands of bases away through DNA folding (Rippe et al *TIBS* 1995; 20: 500-506 (1995)).

The expression vectors may also include selectable markers, such as antibiotic resistance, which enable the vectors to be propagated.

The nucleic acid sequences of the vector containing nucleic acid encoding the MHC protein to be transfected may encode a reporter protein as described above, such as a chloramphenicol acetyl transferase ("CAT") transcription unit, luciferase or green fluorescent protein (GFP). The application of reporter genes relates to the phenotype of these genes which can be assayed in a transformed cell and which is used, for example, to analyse the induction and/or repression of gene expression. Reporter genes for use in studies of gene regulation include other well known reporter genes including the lux gene encoding luciferase which can be assayed by a bioluminescence assay, the uida gene encoding β-glucuronidase which can be assayed by a histochemical test, the lacZ gene encoding β-galactosidase which can be assayed by a histochemical test, the enhanced green fluorescent protein which can be detected by UV light, UV microscopy or by FACS.

The DNA comprising the nucleic acid sequence of the MHC protein may be single or double stranded. Single stranded DNA may be the coding or sense strand, or it may be the non-coding or anti-sense strand. For therapeutic use, the nucleic acid sequences are in a form capable of being expressed in the subject to be treated.

The termination sequences in the vector may be a sequence of adenylate nucleotides which encode a polyadenylation signal. Typically, the polyadenylation signal is recognisable in the subject to be treated, such as, for example, the corresponding sequences from viruses such as, for human treatment, the SV40 virus. Other termination signals are well known in the art and may be used.

Preferably, the polyadenylation signal is a bidirectional terminator of RNA transcription. The termination signal may be the polyadenylation signal of the simian 40 virus (SV40), for example the SV40 late poly(A). Alternatively, the termination sequence may be the polyadenylation signal of bovine growth hormone which results in maximal expression when combined with a CMV promoter (Yew et al. *Human Gene Therapy*, 8: 575-584 (1997)).

In addition the expression vector may comprise a further polyadenylation sequence, for example an SV40 early poly (A). Such a further poly(A) may be located upstream of the nucleic acid sequence encoding the MHC protein to reduce cryptic transcription which may have initiated within the vector thereby ensuring that basal gene expression from the vector is minimal.

Gene expression from integrated viral genomes may be susceptible to chromosomal positional effects. Such effects include transcriptional silencing and promoter activation by nearby heterologous enhancers. In addition, integrated sequences can activate expression of nearby genes and oncogenes. These effects are reduced through the use of elements which form boundaries to the inserted viral genome.

Insulators are genetic elements such as the chicken β-globin 5' DNase I hypersensitive site (5'HS4) which mark a boundary between an open chromatin domain and a region of constitutively condensed chromatin.

Other elements termed scaffold or matrix attachment regions (S/MAR) anchor chromatin to nuclear structures and form chromosomal loops which may have a physiological role in bringing distal regulatory elements into close proximity to a corresponding promoter. An example is located in the human interferon-γ locus and is termed the IFN-SAR. Both insulators and S/MAR can reduce position effects with greatest activity demonstrated when they were combined in a lentiviral vector (Ramezani et al, *Blood* 101: 4717-24, (2003)). Clearly such elements can be of benefit in regulated vectors such as those described herein after they are integrated into the host cell genome.

The compositions of the present invention comprise a microsome, or a fragment thereof, in association with an externally disposed peptide antigen that has been loaded into the microsome. The association may be such that the peptide antigen is inserted in the membrane of the microsome such at least one epitope of the peptide antigen is exposed with respect to the outer membrane of the microsome. The membrane of microsomes further contains a protein of the MHC that presents the peptide antigen to T-cells in order for the antigen to be recognised by the immune system. The MHC protein is either naturally present in the cell organelles of the cell from which the microsomes were produced, or it is a MHC protein that has been transfected into the cell through recombinant DNA techniques and expressed, prior to preparation of the microsomes. The inserted antigenic peptide and the MHC protein form an association in the membrane of the microsome which permits external disposition of the proteins for interaction with the cells of the immune system.

The antigenic peptides may be introduced or loaded into the microsome by means of incubating the microsome with the peptide antigen in the presence of a nucleoside triphosphate (NTP), for example adenosine triphosphate (ATP) and NTP regeneration system. It appears that an NTP, such as ATP, facilitates the incorporation of the peptide antigen into the microsome through protein transporters located in the membrane of the microsome. Without wishing to be bound unnecessarily by theory, it appears that once the microsome is incubated with the peptide antigen in the presence of an NTP that the antigen is able to associate with MHC class I proteins already present in the membrane of the microsome. Alternatively, the antigenic peptides may also loaded into the microsomes after inside-out processing and in this case, the NTP is not required.

The antigenic peptide present in association with the microsome suitably has one or more epitopes. An epitope is the smallest part of an antigen recognisable by the combining site of an immunoglobulin and may be linear or discontinuous. Therefore, any type of MHC binding peptides, natural or synthesized or artificially modified, is included.

The antigenic peptides may be from a source that is foreign, i.e. non-self, or self, i.e. an autoantigen. Foreign antigenic peptides may originate from virus, bacteria, yeast, fungi, protozoa, or other micro-organism (i.e. an infectious agent), or of higher life forms such as plants or animals. In some embodiments of the invention, the antigen may be an auto-antigen, for example an antigen expressed by a neoplastic cell or cell of a cancer tumour, a normal self-protein (in the case of an tolerising vaccine of the invention for an auto-immune disorder).

Where the antigen is from a neoplastic cell or cell of a cancer tumour, the cell may be from a melanoma, lung adenocarcinoma, colon cancer, breast cancer or leukemia cell. Auto-immune disorders include, but are not limited to, Multiple Sclerosis (MS), Systemic Lupus Erythamatosus, Type-1 or Insulin-dependent Diabetes, Antiphospholipid Syndrome, Myasthenia Gravis, Myositis, Sjogren's Syndrome and Rheumatoid arthritis.

In some embodiments of the invention, it may be preferred to prepare the composition with an antigenic peptide of more than one type, or antigenic peptides having a sequence modified to increase immunogenicity. The cell may also be transfected prior to the preparation of the microsomes with more than one type of MHC molecules which may be useful in the case of recipients of the compositions when used as vaccines who have more than one type of MHC allotype.

In a preferred embodiment of this aspect of the invention, there is provided a composition as defined above in which the ratio of antigen to MHC molecule in the microsome is optimal for the induction of a specific immunoresponse, for example in the range of from 0.1 to 1.5, preferably of from 0.2 to 1.2 or 0.5 to 1.0, and most preferably from 0.2-0.5 to 1.0. The amount of loaded antigenic peptides may be different according to the level of immune response induced.

Defined antigenic peptides of major diseases can be readily selected from the scientific literature or identified by bioinformatic tools, (Renkvist et al *Cancer Immunol Immunother* 50, 3-15 (2001); Coulie et al Immunol Rev 188, 33-42 (2002); De Groot et al *Vaccine* 19 (31), 4385-95 (2001)).

For example, the influenza virus derived peptides SIIN-FEKL and ASNENMETM, or the peptide YLQLVFGIEV from melanoma cells.

Table 1 shows details of Class I HLA-restricted cancer/testis antigens; Table 2 shows Class I HLA-restricted melanocyte differentiation antigens; Table 3 shows Class I HLA-restricted widely expressed antigens; Table 4 shows Class I HLA-restricted tumor specific antigens; Table 5 shows Class II HLA-restricted antigens; Table 6 shows epitopes derived from fusion proteins; and Table 7 shows frequency of epitopes recognised by a given HLA allele.

Further examples are shown in Table 8 of Hepatitis C virus (HCV) peptides from Anthony et al *Clinical Immunol.*, vol. 103, pages 264-276 (2002); in Table 9 of Human Immunodeficiency Virus-1 (HIV-1) from Kaul et al *J. Clinical Invest.*, vol. 107, pages 1303-1310 (2001; in Table 10 of Hepatitis C Virus (HCV) peptides from Koziel et al *J. Virol.*, vol. 67, pages 7522-7532 (1993); and in Table 11 of Hepatitis C Virus (HCV) from He et al *PNAS USA*, vol. 96, pages 5692-5697 (1999).

The antigenic peptide epitopes may be present as a monomer or as repeated sequence of the epitope, such as dimer, trimer, tetramer, or higher multiple, such as a pentamer, hexamer, heptamer, octamer, nonamer or decamer. Fragments of the epitope sequences can be used, as well as overlapping sequences that include the epitope sequence.

The term "peptide" includes both polypeptide and protein, unless the context specifies otherwise.

Such peptides include analogues, homologues, orthologues, isoforms, derivatives, fusion proteins and proteins with a similar structure or are a related polypeptide as herein defined.

The term "analogue" as used herein refers to a peptide that possesses a similar or identical function as a protein sequence described herein but need not necessarily comprise an amino acid sequence that is similar or identical to such an amino acid sequence, or possess a structure that is similar or identical to that of a protein described herein. An amino acid sequence of a peptide is "similar" to that of a peptide described herein if it satisfies at least one of the following criteria: (a) the peptide has an amino acid sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of a peptide described herein; (b) the peptide is encoded by a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) of a peptide sequence described herein; or (c) the peptide is encoded by a nucleotide sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence encoding a peptide described herein.

Stringent conditions of hybridisation may be characterised by low salt concentrations or high temperature conditions. For example, highly stringent conditions can be defined as being hybridisation to DNA bound to a solid support in 0.5M $NaHPO_4$, 7% sodium dodecyl sulfate (SDS), 1 mM EDTA at 65° C., and washing in 0.1×SSC/0.1% SDS at 68° C. (Ausubel et al eds. "*Current Protocols in Molecular Biology*" 1, page 2.10.3, published by Green Publishing Associates, Inc. and John Wiley & Sons, Inc., New York, (1989)). In some circumstances less stringent conditions may be required. As used in the present application, moderately stringent conditions can be defined as comprising washing in 0.2×SSC/0.1% SDS at 42° C. (Ausubel et al (1989) supra). Hybridisation can also be made more stringent by the addition of increasing amounts of formamide to destabilise the hybrid nucleic acid duplex. Thus particular hybridisation conditions can readily be manipulated, and will generally be selected according to the desired results. In general, convenient hybridisation temperatures in the presence of 50% formamide are 42° C. for a probe which is 95 to 100% homologous to the target DNA, 37° C. for 90 to 95% homology, and 32° C. for 70 to 90% homology.

A peptide with "similar structure" to that of a peptide described herein refers to a peptide that has a similar secondary, tertiary or quaternary structure as that of a peptide described herein. The structure of a peptide can determined by methods known to those skilled in the art, including but not limited to, X-ray crystallography, nuclear magnetic resonance, and crystallographic electron microscopy.

The term "fusion protein" as used herein refers to a peptide that comprises (i) an amino acid sequence of a peptide described herein, a fragment thereof, a related peptide or a fragment thereof and (ii) an amino acid sequence of a heterologous peptide (i.e., not a peptide sequence described herein).

The term "homologue" as used herein refers to a peptide that comprises an amino acid sequence similar to that of a peptide described herein but does not necessarily possess a similar or identical function.

The term "orthologue" as used herein refers to a non-human peptide that (i) comprises an amino acid sequence similar to that of a peptide described herein and (ii) possesses a similar or identical function.

The term "related peptide" as used herein refers to a homologue, an analogue, an isoform of, an orthologue, or any combination thereof of a peptide described herein.

The term "derivative" as used herein refers to a peptide that comprises an amino acid sequence of a peptide described herein which has been altered by the introduction of amino acid residue substitutions, deletions or additions. The derivative peptide possess a similar or identical function as peptides described herein.

The term "fragment" as used herein refers to a peptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues) of the amino acid sequence of a peptide as described herein, mutatis mutandis. The fragment of may or may not possess a functional activity of such peptides.

The term "isoform" as used herein refers to variants of a peptide that are encoded by the same gene, but that differ in their isoelectric point (pI) or molecular weight (MW), or both. Such isoforms can differ in their amino acid composition (e.g. as a result of alternative splicing or limited proteolysis) and in addition, or in the alternative, may arise from differential post-translational modification (e.g., glycosylation, acylation, phosphorylation). As used herein, the term "isoform" also refers to a peptide that exists in only a single form, i.e., it is not expressed as several variants.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=# of identical positions/total # of positions×100).

The determination of percent identity between two sequences can be accomplished using a mathematical algorithm known to those of skill in the art. An example of a mathematical algorithm for comparing two sequences is the algorithm of Karlin and Altschul Proc. Natl. Acad. Sci. USA (1990) 87:2264-2268, modified as in Karlin and Altschul (1993) Proc. Natl. Acad. Sci. USA 90:5873-5877. The NBLAST and XBLAST programs of Altschul et al, J. Mol. Biol. (1990) 215:403-410 have incorporated such an algorithm. BLAST nucleotide searches can be performed with the NBLAST program, score=100, wordlength=12 to obtain nucleotide sequences homologous to a nucleic acid molecules encoding a peptide sequence as described herein. BLAST protein searches can be performed with the XBLAST program, score=50, wordlength=3 to obtain amino acid sequences homologous to a peptide as described herein. To obtain gapped alignments for comparison purposes, Gapped BLAST can be utilised as described in Altschul et al, Nucleic Acids Res. (1997) 25:3389-3402. Alternatively, PSI-Blast can be used to perform an iterated search which detects distant relationships between molecules (Id.). When utilizing BLAST, Gapped BLAST, and PST-Blast programs, the default parameters of the respective programs (e.g., XBLAST and NBLAST) can be used.

Another example of a mathematical algorithm utilised for the comparison of sequences is the algorithm of Myers and Miller, CABIOS (1989). The ALIGN program (version 2.0) which is part of the GCG sequence alignment software package has incorporated such an algorithm. Other algorithms for sequence analysis known in the art include ADVANCE and ADAM as described in Torellis and Robotti *Comput. Appl. Biosci.* (1994) 10:3-5; and FASTA described in Pearson and Lipman *Proc. Natl. Acad. Sci. USA* (1988) 85:2444-8. Within FASTA, ktup is a control option that sets the sensitivity and speed of the search.

The skilled person is aware that various amino acids have similar properties. One or more such amino acids of a substance can often be substituted by one or more other such amino acids without eliminating a desired activity of that substance. Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

Amino acid deletions or insertions may also be made relative to the amino acid sequence of a peptide sequence as described herein. Thus, for example, amino acids which do not have a substantial effect on the activity of such peptides, or at least which do not eliminate such activity, may be deleted. Amino acid insertions relative to the sequence of peptides as described herein can also be made. This may be done to alter the properties of a protein of the present invention (e.g. to assist in identification, purification or expression, where the protein is obtained from a recombinant source, including a fusion protein. Such amino acid changes relative to the sequence of a peptide from a recombinant source can be made using any suitable technique e.g. by using site-directed mutagenesis. The molecule may, of course, be prepared by standard chemical synthetic techniques, e.g. solid phase peptide synthesis, or by available biochemical techniques.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

According to the present invention, purified microsomes representing the endoplasmic reticulum, lysosomes or endosomes in antigen-presenting cells (APC) can be used to load antigenic peptides on its MHC class I or II molecules. Results from in vitro and in vivo immunisation described herein show that peptide-loaded microsome elucidates much stronger responses than peptide-loaded APC measured by T cell proliferation and production of IL-2. By quantitating the amount of peptide-receptive MHC class I molecules, the receptive class I molecules on APC surface are below the radio-chemical detection limit. However, a significant amount of peptide bound MHC class I is detected in the microsome. In addition, a similar amount of co-stimulatory molecules, B7.1 and B7.2 is detected in microsomes in comparison to cell surface. Thus, the microsomes loaded with antigenic peptides represent an effective vaccine composition.

The present invention has found that more than 50% of the MHC class I molecules in the ER of APC are peptide receptive. By the process of "inside-out", the microsomes loaded with Kb specific OVA-peptide can induce T cell responses in vitro and in vivo. In contrast, the APCs pulsed with same peptide have much less ability to stimulate T cell responses. Given that the microsomes contain co-stimulatory molecules, the microsomes isolated from APCs represent promising vehicles for peptide vaccines in the future for a wide variety of diseases.

In addition to transfecting selected MHC genes into the animal cell prior to microsome preparation, it may also be desirable to transfect or co-transfect the cells with genes encoding co-stimulatory molecules such as B7 and/or the genes encoding cytokines, for example an interleukin or an interferon, such as IL-2. In the case of cytokines, the transgene will be fused with trans-membrane domain of CD2 or CD4 for targeting the cytokines into the ER membrane. In addition, in order to enrich the level of MHC, co-stimulatory molecules and membrane-bound cytokines in the ER, KDEL or other ER retention signalling (Nilsson T, & Warren G., *Curr Opin Cell Biol.* 6 (4), 517-21 (1994)) will be tagged at the C-terminus of the transgenes for the retention of transgene products in the ER. The expression cassettes for these transgenes are similar to MHC class I transgenes.

According to the present invention, therefore, the vaccine compositions may be co-administered with one or more cytokines, such as an interferon or an interleukin, that can promote T cell immune response such as Il-2, IL-15, IL-6, GM-CSF, IFNγ, other cytokines promoting T cell responses, and/or conventional adjuvant. These can be suitably mixed with the microsomes loaded with antigen prior to administration, or may be suitably prepared as membrane-bound constituents of the microsomes. Such membrane-bound substituents may be introduced using recombinant DNA techniques, as discussed above, to engineer expression of the cytokine in the cell organelle that will ultimately be used to form the microsomes, or alternatively the cytokines may be loaded into the microsome membrane or bound to surface proteins.

A membrane bound cytokine expressed in a microsome preparation may be prepared by transfecting an antigen presenting cell with a construct comprising a cytokine molecule fused to a membrane anchor protein, optionally with an ER-retention signal. For example, a microsome including membrane bound IL-2 molecules can be prepared by constructing a vector comprising nucleic acid encoding a fusion protein comprising the CD2 membrane domain fused to the C-terminus of IL-2 and an ER-retention signal, such as the 16 amino-acid sequence from E15-9K adenovirus protein, where the ER-retention signal is fused to the C-terminus of the CD2 protein. Expression of the vector in the antigen presenting cell leads to accumulation of the cytokine in the organelles of the cell, i.e. the ER, which enables preparation of microsomes containing membrane-bound cytokine.

In addition, it may be convenient to include detection and monitoring of the specific immune responses towards the vaccine, for example by techniques such as ELISA for detection of serum cytokine, e.g. IL-2 and/or IFNγ, or an in vitro T cell response assay with peptide loaded microsomes, or a proliferative cell assay.

In its simplest form, the present invention provides a composition comprising an isolated microsome of the endoplasmic reticulum of an animal cell, or a membrane fragment thereof, in association with an externally disposed peptide antigen and a protein of the Major Histocompatibility Complex (MHC). Suitably formulated for administration as a vaccine.

According to a second aspect of the invention, there is provided a composition according to the first or second aspects of the invention for use in medicine. This aspect of the invention therefore extends to a method of treatment or prophylaxis of a subject suffering from a disease or condition, comprising the step of administering to the subject a vaccine as defined above.

According to a third aspect of the invention, there is provided the use of a composition as defined above in the preparation of a vaccine for the prophylaxis or treatment of a disease condition. The disease may be an infection caused by a micro-organism or virus, or it may be a cancer which is characterised by neoplastic cell growth and/or tumour formation. Alternatively, the disease may be an autoimmune condition, where a vaccine may have therapeutic use in inducing tolerance to self-antigens. Uses in accordance with this aspect of the invention also extend to methods of treatment of such disease conditions comprising administering said compositions to a subject in need thereof. Suitably, vaccine compositions of the present invention can be administered by any convenient route such as intramuscular, intravenous, intraperitoneal, oral or by injection in to the cerebrospinal fluid.

Diseases or conditions that can be treated using a vaccine of the present invention include, but are not limited to melanoma, lung adenocarcinoma, colon cancer, breast cancer or leukemia. Auto-immune disorders include, but are not limited to, Multiple Sclerosis (MS), Systemic Lupus Erythamatosus, Type-1 or Insulin-dependent Diabetes, Antiphospholipid Syndrome, Myasthenia Gravis, Myositis, Sjogren's Syndrome and Rheumatoid arthritis. In addition, viral infection, such as HIV infection, herpes virus infection, hepatitis C virus infection, or parasite infections, such as protozoan parasite infection of *Plasmodium*, the causative agent responsible for malaria, for example *Plasmodium falciparum, Plasmodium vivax, Plasmodium berghei, Plasmodium yoelii* or *Plasmodium knowlesi*, or another parasite such as *Toxoplasma gondii*, or *Trypanosoma brucei*, or *Entamoeba histolytica*, or *Giardia lambia*, or bacterial infection, such as *E. coli* 0157, *Vibrio cholerae*, etc.

It is also envisaged that the microsomes of the present invention when loaded with peptide antigen may be fused with antigen presenting cells (APC) prior to administration of the combined preparation to the patient. Suitably, the APC are taken from the patient prior to treatment, but may also be taken from an allogenic source. In such cases, where an allogenic source of cells is used, immunosuppresive drugs may also form part of the treatment protocol.

According to a fourth aspect of the invention, there is provided a process for the preparation of a vaccine composition as defined above, the process comprising incubating a population of microsomes and an antigenic peptide in the presence of a nucleoside triphosphate (NTP), followed by further processing to prepare inverted microsomes and formulating the resulting preparation in an physiological diluent and optionally an adjuvant. Reagents such as glucose have ability to preserve the conformation of prepared microsome vaccine and may be included. Suitably, the incubated microsomes will be washed and resuspended in a vaccine solution of an physiological diluent containing an amount of antigenic peptides for preventing the dissociation of the MHC-peptide complex present in the microsome membrane.

The process of loading the microsomes with antigen is carried out in the presence of a nucleoside triphosphate (NTP), such as ATP, GTP, CTP, TTP, or UTP. The antigen loading process may also be carried out in the presence of more than one type of antigenic peptide. In this way a plurality of antigens can be loaded into the microsome.

Inverted microsomes may be prepared by further processing of the microsomes that disrupts the membranes of the microsomes under conditions which allow the membrane to reform and which encourage the formation of "inside-out" microsomes. The use of repeated freeze-thaw steps are therefore suitable in this regard. For example, the microsomes can be suspended in a suitable medium, or buffer, e.g. Phosphate buffered saline (PBS), and then briefly immersed into liquid nitrogen for a suitable period of time, suitably from one to five minutes, preferably for two minutes, and then moved to 37° C., such as in a water-bath, for a suitable period of time, suitably for two to six minutes, preferably for four minutes. The number of repeated steps of freeze-thaw may be from three to five, suitably four repeat steps.

In an alternative embodiment of this aspect of the invention, the process may comprise the loading of inverted microsomes, prepared as described above, with antigen. For loading antigenic peptides into inverted microsomes, the presence of an NTP may not be necessary (although it may be desirable).

According to a fifth aspect of the invention, there is provided a kit of parts comprising a composition as defined above and one or more cytokine and/or adjuvant in sealed containers. Suitably, the kit will comprise instructions for use in a method or use of the invention as defined above.

According to a sixth aspect of the invention, there is provided a kit of parts comprising a composition as defined above and one or more cytokine and/or adjuvant molecules for separate, subsequent or simultaneous administration to a subject.

Preferred features for the second and subsequent aspects of the invention are as for the first aspect mutatis mutandis.

In a particularly preferred embodiment of the invention there is provided a vaccine composition for the prophylaxis or treatment of a disease that can be characterised by the expression of a defined antigen or a peptide sequence which is potentially immunogenic by an infectious agent or which is characterised by the expression of an antigen of a native cell, in which the composition is prepared by:
(1) obtaining a sample of antigen presenting cells which express MHC proteins;
(2) homogenising the cells under conditions such that a preparation of microsomes is isolated;
(3) preparation of antigenic peptides, for example by means of recombinant DNA technology, or from isolation from a natural tissue source, or source of infectious agent, or in most cases synthesised antigenic peptides.
(4) incubation of antigenic peptides and microsomes in the presence of an NIP to load the microsomes with antigenic peptides;
(5) further processing of microsomes loaded in step (4) to prepare a population of inverted microsomes
(6) formulation of loaded inverted microsomes a vaccine in a physiological diluent and/or adjuvant as appropriate As described above, the microsomes may also be prepared from an isolated population of cells or a cell line. The cells or cell line may be have been transfected with a nucleic acid construct to express a protein of choice prior to microsome preparation.

According to the above protocol, the microsomes are loaded with antigenic peptide and then subsequently processed to prepare inverted microsomes. However, in an alternative embodiment, the inverted microsomes may be prepared first and then loaded with antigen, in which case the presence on an NTP in step (4) may not be required.

As discussed above, the vaccine compositions of the invention preferably comprise inverted microsomes, more preferably a homogenous population of inverted microsomes. However, non-inverted microsomes may also be present in the population of inverted microsomes.

The cells may be MHC negative so as to permit transfection of the cell line with appropriate nucleic acid encoding the MHC class molecule of choice for the vaccine. Preparation of antigen may also include synthesis of antigenic peptides by means of chemical means.

The loading of non-inverted microsomes with antigenic peptide takes place in the presence of an NTP. The loading of inverted microsomes does not appear to require the presence of an NTP, although it may be preferred.

The invention will now be further described by way of reference to the following Examples and Figures which are provided for the purposes of illustration only and are not to be construed as being limiting on the invention. Reference is made to a number of Figures in which:

FIG. 1 shows crosslinking of H2-Kb molecules by crosslinker-modified OVA peptide in the microsomes of RAW309Cr.1 cells. The $^{125}$I-labeled ANB-NOS-OVA peptide was mixed with the microsomes of RAW309Cr.1 cells in the presence or absence of ATP-regenerating system or of native OVA-peptide at a ten-fold molar excess. The crosslinked H-2Kb was indicated.

FIG. 2 shows concentration of OVA-peptide receptive H-2Kb in the microsomes of RAW309Cr.1 cells. For semiquantitation of OVA-peptide receptive H-2Kb, 10 nMs of labelled peptide was incubated with the microsomes or RAW309Cr.1 cells, respectively, under the UV irradiation. The H-2 molecules were precipitated by R218 antiserum and crosslinked Kb molecules were quantitated by phospho-imaging.

FIG. 3 shows detection of H-2 molecules in the microsomes or on the surface of RAW309Cr.1 cells. 30 μg proteins from NP40 lysates of RAW309Cr.1 microsomes or RAW309Cr.1 cells were separated on 10% SDS-PAGE. The lysates were diluted at the titration indicated and separated on the SDS-PAGE. Immunoblotting of H-2 molecules was detected by R218 anti-H-2 antiserum.

FIG. 4 shows detection of B7.1, B7.2 and ICAM-1 in the microsomes of RAW309Cr.1 cells. 30 μg proteins from NP40 lysates of RAW309Cr.1 microsomes or RAW309Cr.1 cells were separated on 10% SDS-PAGE. Immunoblotting of B7.1, B7.2 and ICAM-1 was detected by specific antibodies.

FIG. 5 shows stimulation of B3Z T cells by OVA-peptide edited microsomes. Microsomes from $2 \times 10^5$ RAW309Cr.1 cells were used to load OVA or Ld-specific peptide as described in Material and Methods. $2 \times 10^5$ RAW309Cr.1 cells were pulsed with OVA peptide (see Material and Methods). After washing, peptide-pulsed $2 \times 10^5$ RAW309Cr.1 cells, OVA-loaded microsomes, Ld-peptide loaded microsomes, and the microsomes without peptide were co-cultured with $10^5$ B3Z cells for over night. A) After washing with PBS, LacZ activity in B3Z cells was assayed by total cellular lysates with the LacZ substrate ONPG. The absorbance (415 nM) was read after incubation for four hours at 37° C. B3Z cells cultured with 100 nM OVA peptide and normal medium were used as positive and negative control for the B3Z stimulation. B) The supernatants of these cultures were submitted for measuring IL-2 production by ELISA. The experiment was repeated four times with similar results. Error bars indicate the SEM of triplicate cultures.

FIG. 6 shows stimulation of B3Z T cells by the microsomes of $2 \times 10^5$ RAW309Cr.1 cells pre-loaded with different concentrations of OVA-peptides. Microsomes loaded with OVA-peptide at different concentration indicated were co-cultured with B3Z cells overnight before the assay of LacZ activity.

FIG. 7 shows OVA-peptide edited microsomes stimulates specific T cell responses in vivo. C57BL/6 (H-2b) mice were primed i.s. by OVA-edited microsomes or Ld-peptide loaded microsomes or OVA peptide or OVA-pulsed RAW309Cr.1 cells and challenged by same stimulus after seven days. Six days after the challenge, enriched T cells were isolated from spleens and cultured at $10^5$ cells/well with stimulus indicated. The RAW309Cr.1 cells were irradiated before co-culture with T cells. After three days, supernatants were harvested for cytokine ELISA (b) and cultures pulsed with [$^3$H]thymidine (a). The results are representative of groups of at least three mice per treatment group and the experiment was repeated four times with similar results. Error bars indicate the SEM of triplicate cultures. Similar set of experiments performed in Balb/c (H-2d) mice served as negative control.

FIG. 8 shows activation of TCR induced MAK kinases. $10^7$ T cells from OVA-microsomes immunised C57BL/6 were stimulated with OVA-pulsed RAW309Cr.1, OVA-microsomes and anti-CD3/CD28, respectively. Activation of ERK and JNK was detected by anti-p-ERK and anti-p-JNK antibodies. Similar levels of ERK and JNK detected by anti-ERK and anti-JNK severed as loading control.

FIG. 9 shows OVA-receptive H-2Kb detected in microsomes, but not on the surface of RAW309Cr.1 cells. The $^{125}$I-labeled ANB-NOS-OVA peptide 10 nM was mixed without or with native OVA peptide at concentrations indicated. The mixed peptides were incubated with microsomes equivalent to $10^7$ RAW309Cr.1 cells or with $10^7$ RAW309Cr.1 cells. The crosslinked H2-Kb molecules were indicated.

FIG. 13 shows the amino acid sequences for the MHC class I antigens A2 alpha chain precursor and B7 alpha chain precursor (Accession nos. P01892 and P01889, respectively).

FIG. 14 shows the amino acid sequences for the MHC class II antigens DRB3-1 beta-chain precursor and HLA-DQ alpha 1 (DQw4 specificity) precursor—human (Accession nos. P79483 and A37044, respectively).

Material and Methods

Cell Lines and Animals

Figure 1:
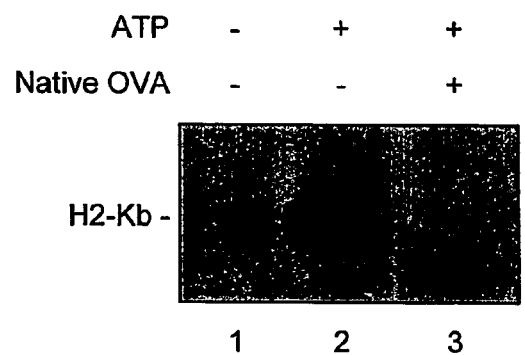

B3Z is a CD8 T cell hybridoma that expresses LacZ in response to activation of T cell receptors specific for the SIINFEKL peptide presented by H-2 Kb MHC class I molecules. RAW309Cr.1, a Kd/Kb murine macrophage cell line, used as APCs, was obtained from ATCC (ATCC TIB-69). All cells were cultured in Dulbecco's modified Eagle's medium with 10% fetal calf serum. Female C57BL/6 mice H-2b and Balb/c mice H-2d were obtained at 6 weeks of age. All procedures with animals were carried out in accordance with approved protocols.

Antibodies, Peptides, and Peptide Modification

All peptides were synthesised in a peptide synthesiser (model 431A, Applied Biosystems, Foster City, Calif.), using conventional F-moc chemistry, and were subsequently purified by HPLC. The purified peptides were dissolved in PBS.

Peptide OVA 257-264 (SIINFEKL) was modified by substitution of third residue isoleucine to tyrosine in order for iodination and by covalently coupling a phenylazide with a nitro group on the ϵ-amino group of lysine at position seven. This nitro group can be photoactivated. The crosslinker modification was performed by mixing 0.5 mg of ANB-NOS (N-5-azido-2-nitrobenzoyloxysuccinimide) in 200 μl DMSO with 100 μg peptide in 100 μl PBS and 50 μl CPAS (3-[cyclohexylamino]-1-propanesulfonic acid) (0.5 M, pH 10). The reaction was allowed to proceed for 30 min on ice. To remove the excess ANB-NOS and ions, the mixture was purified by gel filtration on Sephadex G-10 and subsequently by HPLC. An aliquot (1 μg) of the peptide was labelled by chloramines-T-catalyzed iodination ($^{125}$I). The modification and labelling experiments were performed in the dark.

Antisera, Immunoprecipitation, and SDS-PAGE

Rabbit antiserum to H2 (R218) was kindly provided by Dr. Sune Kvist, Karolinska Institute. Monoclonal antibody specific to confirmed H2 (Y3) was kindly provided by Tim Elliot, Cambridge University. Antisera to JNK, ERK, p-ERK and p-JNK were obtained from (Santa Cruz Biotechnology). Immunoprecipitation, immunoblotting and SDS-PAGE were performed as described in Li et al (*J Biol Chem.* 274 (13), 8649-54 (1999)). Protein-A-Sepharose was obtained from Pharmacia (Uppsala, Sweden).

EXAMPLE 1

Preparation of Microsomes and Peptide Binding Assay

Microsomes from RAW309Cr.1, a Kd/Kb murine macrophage cell line were prepared and purified according to the procedure of Saraste et al (*Proc. Natl. Acad. Sci. U.S.A.* 83, 6425-6429 (1986)). The immunogenetics of class I is Kb in RAW cells and Balb/c mice.

Preparation of microsomes from B cells based on a modification of Saraste et al (*Proc. Natl. Acad. Sci. U.S.A.* 83, 6425-6429 (1986)) and Knipe et al (*J. Virol.* 21, 1128-1139 (1977)) for fractionation of microsomal membranes was used. All steps were performed at 0-4° C.).

3×10$^9$ cells are collected and washed once with cold PBS.

Resuspend the cells in 20 ml STKMM-buffer with 10 μl of PMSF (100 mM).

Spin at 1500 rpm for 5 min at 4° C.

Resuspend in 10 ml H$_2$O (with 5 μl PMSF).

Homogenise in 40 ml Dounce, 20 strokes.

Add 30 ml STKMM and mixing well.

Pour over in JA-18 tubes.

Centrifuge at 7500 rpm for 10 min at 4° C.

Carefully collect supernatant to the new tubes.

Centrifuge at 15500 rpm for 54 min at 4° C.

Carefully wash the pellet with 10 ml STKMM buffer, then resuspend the pellet in 1 ml RM buffer with a pipette and homogenise in 15 ml douncer. The rough microsomes will be diluted at a concentration of $A_{OD280}$=60.

Total microsomes (described above) were layered on top of 5 ml of 0.33 M sucrose containing 5 mM benzamidine, layered in turn on top of a sucrose cushion consisting of 1 ml of 2 M sucrose/5 mM benzamidine.

Centrifugation in an SW41 rotor for 60 min at 110,000×g yielded a total microsome band on top of the cushion. The total microsome band was carefully collected. Then, 2 M sucrose/5 mM benzamidine was slowly added to the microsomes to give a final concentration of 45% (w/v) sucrose.

Microsomes were subfractionated by flotation using a modification of the method described in Paulsson et al (*J Biol Chem* 277 (21), 18266-71 (2002)). 100 μl of the total microsomes in 3 ml of 45% (w/v) sucrose was placed at the bottom of an SW41 ultracentrifuge tube and overlaid with the following sucrose solutions: 1 ml of 30% and 1.9 ml each of 27.5%, 25%, 22.5%, and 20.0% (all solutions contained 5 mM benzamidine).

After centrifugation at 4° C. for 10 h at 37,000 rpm (to reach isopyknic conditions), 25 fractions of 300 μl each were collected by upward displacement.

The ER fractions will be determined by western blotting with anti-p58 antibody. (p58 is a ER protein).

The poured ER fractions will be used in peptide-loading and immunisation experiments.

The cross-link mixture contained 50 or 100 nM ($^{125}$I) ANB-NOS-peptide and 10 μl of microsomes (60 $A_{280}$/ml) in a total volume of 100 μl RM buffer (250 mM sucrose, 50 mM TEA-HCl, 50 mM KOAc, 2 mM MgOAc$_2$, and 1 mM DTT). After mixing, the samples were immediately irradiated at 366 nm for 5 min at room temperature. The membranes were then recovered by centrifugation through a 0.5-M sucrose cushion in RM buffer. The membranes were washed once with cold RM buffer. The washing membranes were lysed for immunoprecipitation or for immune blotting. The crosslinking reaction with ATP contained an ATP regeneration system, described in Li et al (*J Biol Chem.* 274 (13), 8649-54 (1999)).

The crosslinking of surface Kb molecules on RAW309Cr.1 cells was performed as mixing 100 nM ($^{125}$I)ANB-NOS-peptide with 10$^7$ cells, equivalent to amount of cells used for making 10 μl of microsomes in a total volume of 100 μl RM buffer. After mixing, the samples were immediately irradiated for 5 min at room temperature. The excess peptides were removed by washing with RM buffer. The cells were lysed for immunoprecipitation with Y3 antibody.

The detection of surface MHC class I was performed by incubating RAW309Cr.1 cells with Y3 antibody at 4° C. for 15 min. After washing, the cells were lysed in 1% NP40 lysis buffer and the cleared lysates were precipitated with protein-A beads. The precipitated MHC class I were detected by immunoblotting with R218 antiserum.

The peptide-editing for stimulation of T cells was performed by mixing microsomes with native peptides with ATP regeneration system for 10 min at room temperature.

The excess of peptides was removed after centrifugation through sucrose cushion in RM buffer. The loaded microsomes were repeatedly freeze/thaw alternately in liquid nitrogen and then in a water bath at 37° C., for 10 times. The processed microsomes were resuspended in PBS at concentration of (6 $A_{280}$/ml) and kept at −80° C. until use. The peptide-pulsed RAW309Cr.1 cells was prepared as mixing peptides 100 nM with 10$^7$ cells in 1 ml medium over night or in 1 ml PBS for four hours at 37° C. The pulsed cells were either washed with PBS before mixing with B3Z T cells or add the mixture directly to the B3Z.

EXAMPLE 2

Activation of B3Z T Cell Hybridoma

The prepared stimuli including peptide-edited microsomes, peptide-pulsed RAW309Cr.1 cells, OVA peptide, were added to culture of $10^5$ B3Z cells in a total of 200 μl. Addition of PBS and anti-CD3/CD28 coated beads served as negative or positive control, respectively. After over night incubation, the activation of B3Z was represented by LacZ activity using o-nitrophenyl b-D-galactopyranoside (Sigma) substrate. The linear range of OVA-response was determined by the addition of serial dilutions of SIINFEKL to the medium due to that the B3Z cells themselves express Kb and present SIINFEKL.

EXAMPLE 3

Detection of Peptide-Receptive MHC class I Molecules in the Microsome, but not on the Surface of APCs An in vitro peptide transport and loading assay by using crosslinker modified peptides and isolated microsomes of the ER from RAW309Cr.1 has been reported (Li et al *J Biol Chem.* 274 (13), 8649-54 (1999)). The assay allows the examination of both the peptide translocation across the membrane of the ER in the presence of ATP and subsequently the peptide loading on MHC class I molecules (Wang et al *J Immunol.* 157 (1), 213-20 (1996)).

To detect the peptide-receptive MHC class I molecules in the microsomal membranes, a crosslinker (ANB-NOS) was conjugated to the ε-amino group of the lysine residue of an H2-Kb-binding ovalbumin (OVA) peptide (residues 257-264, SIINFEKL) and substituted the isoleucine at position 3 with tyrosine to allow for iodination. These modifications allowed photo-cross-linking of the OVA peptide to H2-Kb molecules during the assembly. For a quantitative comparison of peptide-receptive H2-Kb in microsomes and on cell surface of living RAW309Cr.1, the modified OVA peptide was labelled by $^{125}$I and incubated with microsomes of RAW309Cr.1 and living RAW309Cr.1 cells under UV irradiation. Peptide-bound H2-Kb molecules were subsequently analysed by immunoprecipitation with an anti-H2 antibody Y3. In the absence of ATP, only a few Kb molecules were assembled with OVA peptides, while a significant amount of Kb molecules were cross-linked with OVA peptide in the presence of ATP (FIG. 1). This result confirms that a substantial amount of peptide receptive class I molecules exist in the ER.

Figure 2:
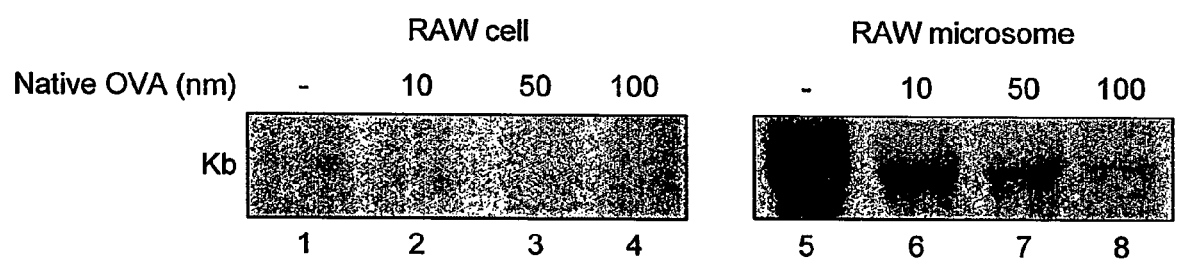
Figure 3:
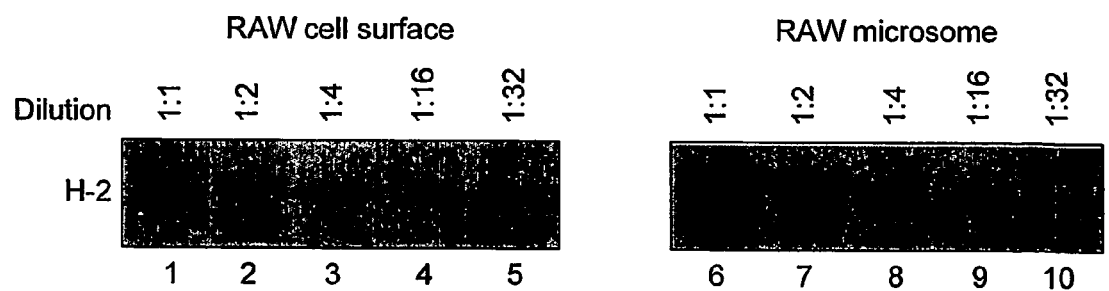

A semi-quantitative analysis of OVA-crosslinked Kb in microsomes and on the surface of RAW309Cr.1 showed that in contrast to the high levels of peptide receptive Kb molecules in the microsomes, the OVA-bound Kb molecules on the surface of APCs was under the radio-chemical detective level (FIG. 2), suggesting again that peptide-receptive MHC class I molecules are mainly in the ER, but not on the surface of APCs. In a competing experiment, it has been shown that the binding of this modified OVA peptide to Kb is specific. In order to examine the affinity of the modified OVA-peptide, the labelled OVA peptide was competed by its native form at different concentrations. The native OVA peptide competed 50% of the report peptide at the concentration of report peptides and completely abolished binding at concentration of ten times of the report peptides (FIG. 2). Moreover, a Ld specific peptide could not compete the OVA binding. This shows that the binding affinity of modified OVA-peptide is Kb specific and similar to its native form. To quantitate the amount of peptides bound to Kb molecules in microsomes derived from $10^6$ RAW309Cr.1, the labelled peptides were incubated with microsomes in the presence of ATP. After crosslinking, MHC class I were precipitated and dpm of peptide-bound Kb was measured and converted to the concentration of peptides. Results showed that about 500 to 1000 peptides were bound to Kb molecules in the microsomes of one cells. In addition, the amount of total MHC class I molecules in the ER are more than that on the surface of RAW309Cr.1 cells (FIG. 3). Thus, microsomes from APCs could be able to deliver sufficient peptide-MHC class I complexes to T cells.

EXAMPLE 4

B7 and ICAM1 are Presented in the Microsomes of APCs

Figure 4:
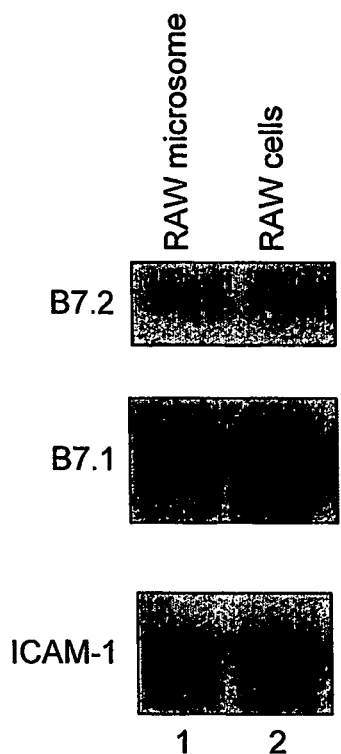

A full T cell response requires signals from both antigen-MHC complex and co-stimulatory molecules such as B7 (Acuto et al, *Immunol Rev.* 192, 21-31 (2003)). Like all the membrane proteins, co-stimulatory molecules are synthesised in the ER and subsequently expressed on the surface of APCs. To quantitate the amount of co-stimulatory molecules of B7 and ICAM-1 in the isolated microsomes, the microsomes equivalent to $5 \times 10^6$ RAW309Cr.1 were lysed and the clear lysates were analysed by western blotting with anti-sera specific to these molecules, respectively. In comparison, a total cell lysates of $5 \times 10^6$ RAW309Cr.1 were also blotted with same antibody. The intensity of B7.1, B7.2 and ICAM-1 bands was quantitated by density analysis. Both B7 and ICAM-1 were readily detected in the microsomal samples (FIG. 4). The amount detected in microsomes was about half of the total cellular lysates. The presence of sufficient amount of co-stimulatory molecules in peptide-edited microsomes could mimic the functional surface of APCs for providing both antigen-MHC and co-stimulatory signals to T cells.

EXAMPLE 5

Microsomes Loaded with Kb-specific OVA Peptides Stimulate T Cells In Vitro

Figure 5A:
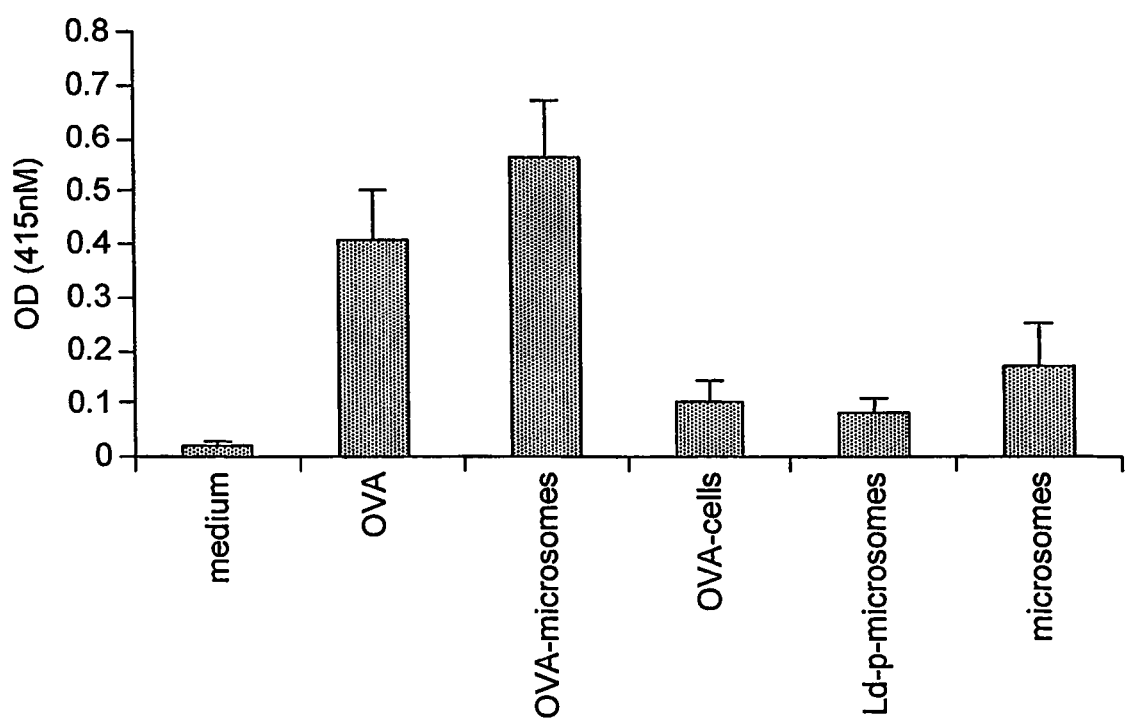
Figure 5B:
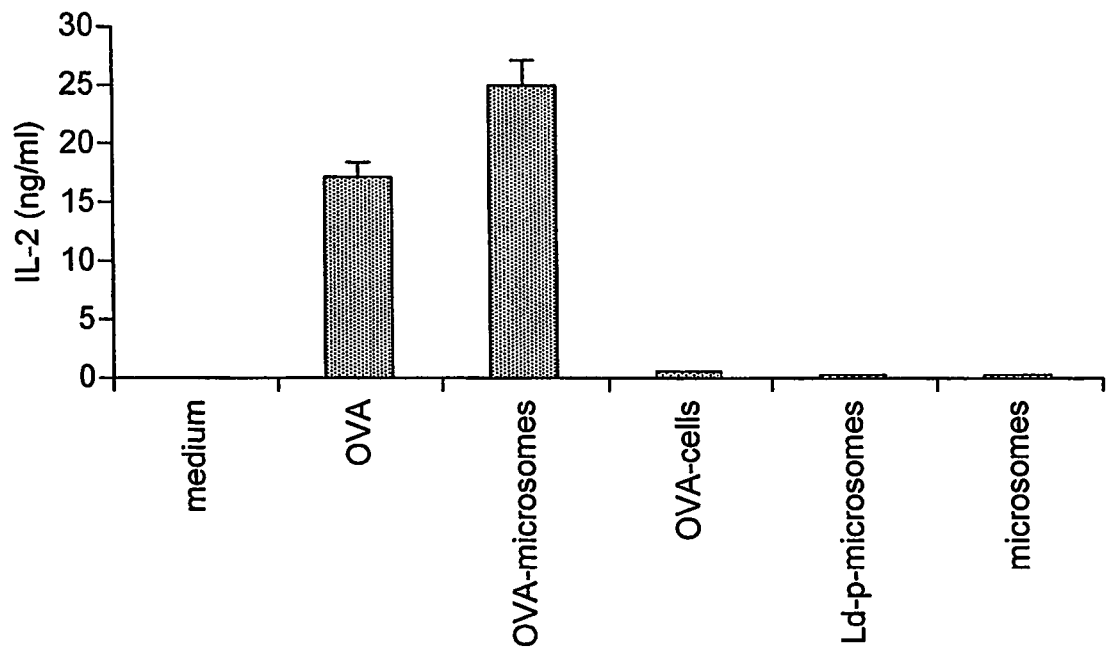
Figure 6:
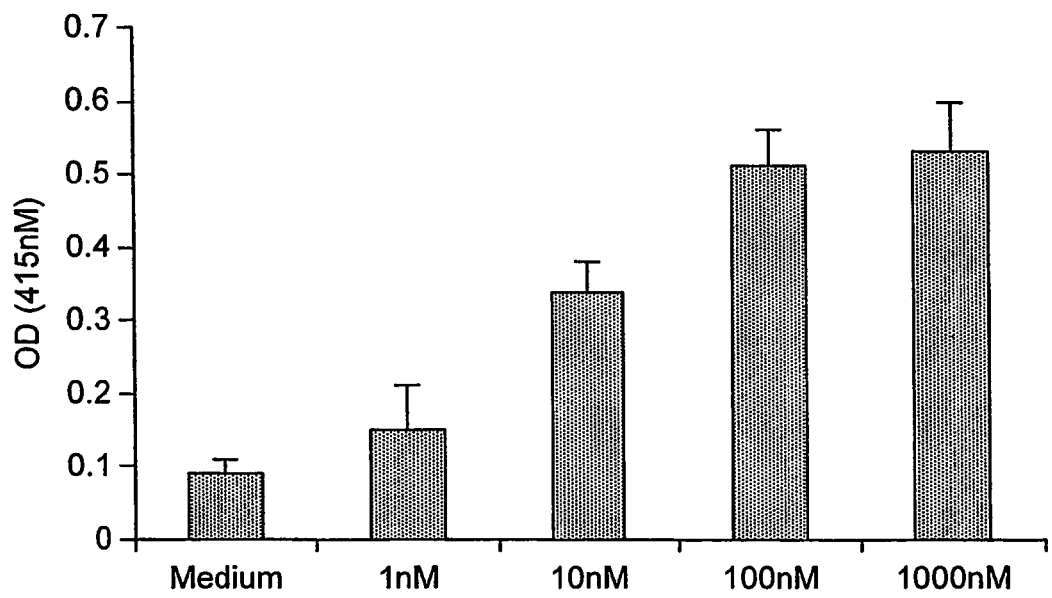

To investigate the ability for peptide-loaded microsomes to induce specific T cell response, the native OVA peptide-edited microsomes were processed for inside-out by repeated freeze-thaw method (materials and methods). The processed microsomes and OVA-peptide pulsed RAW309Cr.1 were used to stimulate B3Z T cell hybridoma which recognises Kb-SIINFEKL complex (Fremont et al *Proc Natl Acad Sci USA.* 92 (7), 2479-83 (1995); Shastri N, & Gonzalez F., *J Immunol.* 150 (7), 2724-36 (1993)). After washing off the excessive peptide, OVA edited Microsome stimulated B3Z T cells by inducing IL-2 production and the expression of IL-2-promoter driven LacZ (FIG. 5). The specificity of OVA-Kb induced B3Z responses was supported by the unresponsiveness of B3Z cells to the microsomes without the peptide or loaded with Ld specific peptide (FIG. 5). Moreover, the levels of responses of B3Z to OVA-edited microsomes was correlated with the amount of OVA-peptides (FIG. 6). OVA-pulsed RAW309Cr.1 could induce the B3Z response in the presence of excessive peptides (Schott et al *Proc Natl Acad Sci USA.* 99 (21), 13735-40 (2002)).

However, if excess peptides were removed by washing, the OVA-pulsed-RAW309Cr.1 could no longer induce B3Z response. Given that OVA itself could induce IL-2 production by B3Z cells (FIG. 5), suggests that not RAW309Cr.1, but OVA itself is the stimuli for B3Z. The ability of SIINFEKL to induce Kb restricted T cell responses in vitro has been reported recently, suggesting that CTL could present peptides to each other (Schott et al *Proc Natl Acad Sci USA*. 99 (21), 13735-40 (2002)). However, the induction CTL response in vitro by peptide-edited microsomes, but not by peptide-pulsed RAW309Cr.1 is consistent with the peptide-binding results (FIG. 2) and indicate that peptide-edited microsomes could mimic APCs to efficiently present antigenic peptides to TCR and stimulate full responses of CTLs.

EXAMPLE 6

Figure 7A:
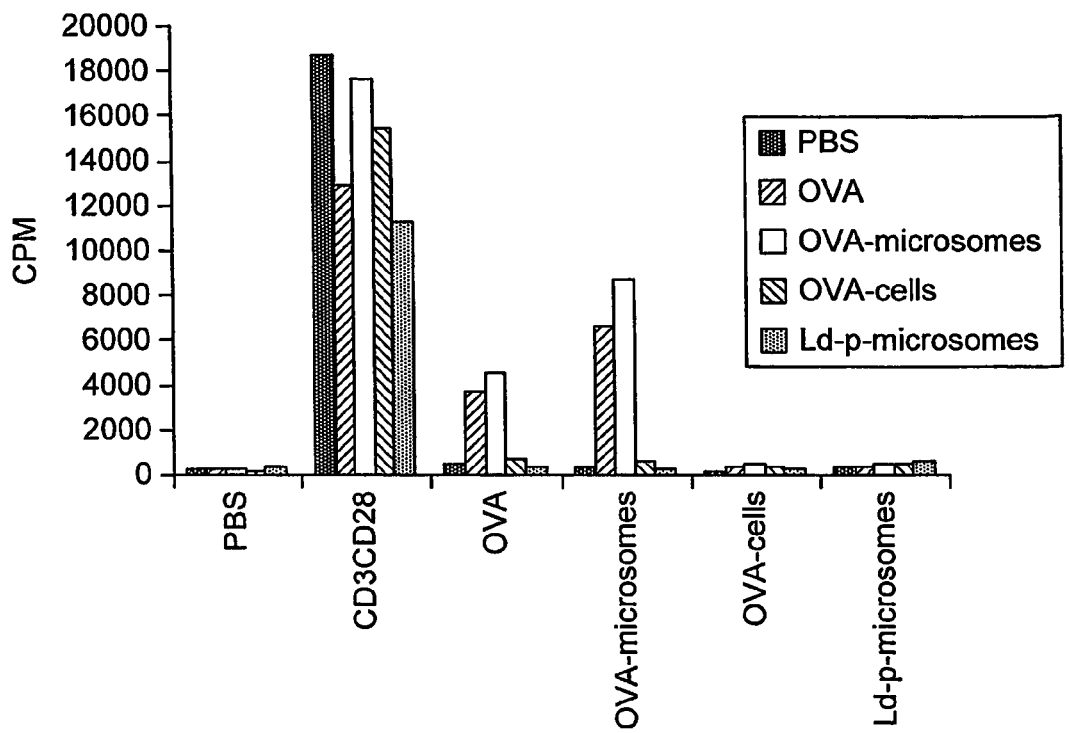
Figure 7B:
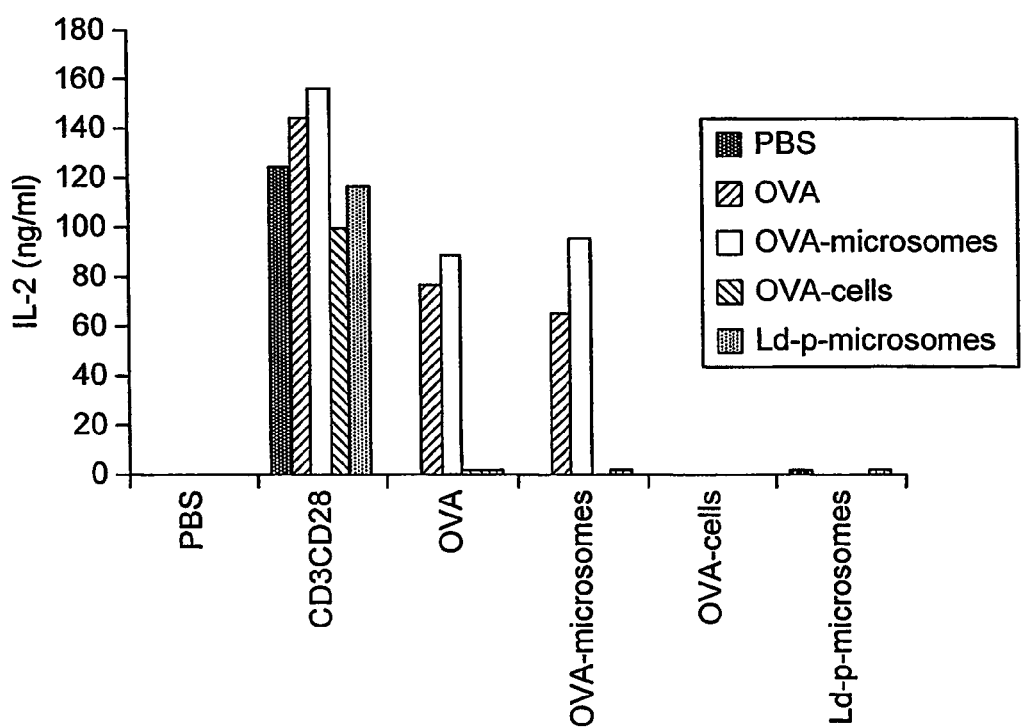

Microsomes Loaded with Kb-specific OVA Peptides Induces OVA-peptide Responses In Vivo To further examine the ability of OVA-edited microsomes to induce immune responses in vivo, OVA-edited microsomes from RAW309Cr.1 cells, microsomes loaded with Ld-specific peptide, soluble OVA peptides, RAW309Cr.1 pulsed with OVA peptides and PBS were used to induce immune response in vivo. Five groups of C57BL/6 or Balb/c mice, each group consisting of five mice, were injected twice subcutaneously with above stimuli, respectively. The interval between injections was one week. Six days after second injection, T cells were isolated from spleens and cross-stimulated in vitro with the five original stimuli, respectively. In addition, anti-CD3/CD28 coated beads were used as positive control. PBS stimulated T cells did not respond to any stimulation, while anti-CD3/CD28 induced proliferative responses in all the groups. OVA-peptide pulsed RAW309Cr.1 and microsomes loaded with Ld-specific peptide did not induce T cells responses (FIG. 7). In contrast, T cells from C57BL/6 groups of OVA-edited microsomes and OVA peptide responded to OVA-edited microsomes in vitro, but not to the OVA-pulsed RAW309Cr.1 or the microsomes loaded with Ld-peptides (FIG. 7). Compelling results from IL-2 production (FIG. 7) again support that OVA-edited microsomes could induce specific T cells responses in vivo (FIG. 7). Balb/c has H-2d, therefore, there was not OVA response induced.

EXAMPLE 7

TCR Signalling Pathways are Activated by OV-microsomes

Figure 8:
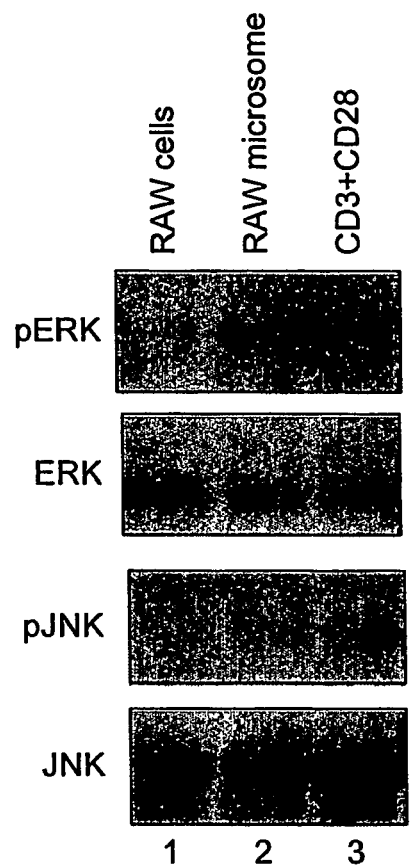
Figure 9:
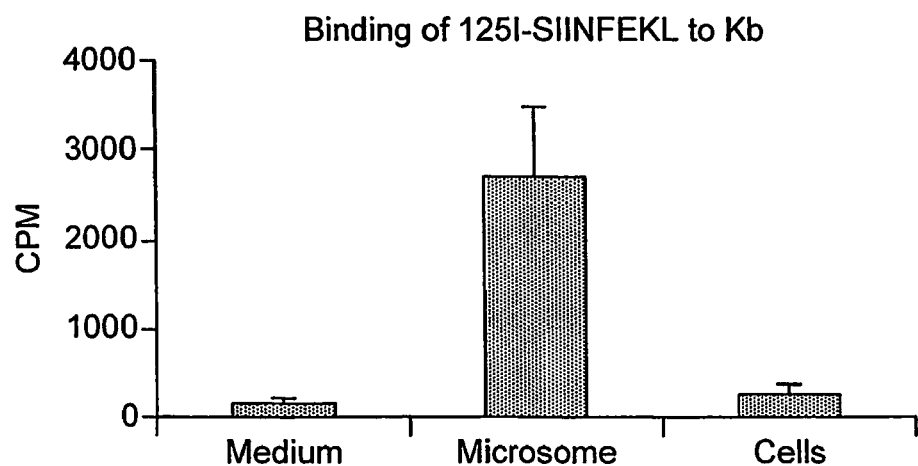

In order to analyse the TCR signalling in response to OVA-microsome stimulation, T cells isolated from C57BL/6 mice immunised by OVA-microsomes were used to induce TCR signalling in vitro. The activation of ERK and JNK was detected in the T cells stimulated with either anti-CD3/CD28 or with OVA-edited microsomes, but not with OVA-pulsed RAW309Cr.1 (FIG. 8). Thus, the biochemical evidence indicates a specific TCR signalling in response to OVA-Kb on microsomes and further supports that microsomes edited with antigenic peptides could induce specific immune responses in vivo.

EXAMPLE 8

Influenza Viral Peptide Loaded Microsomes

Figure 10:
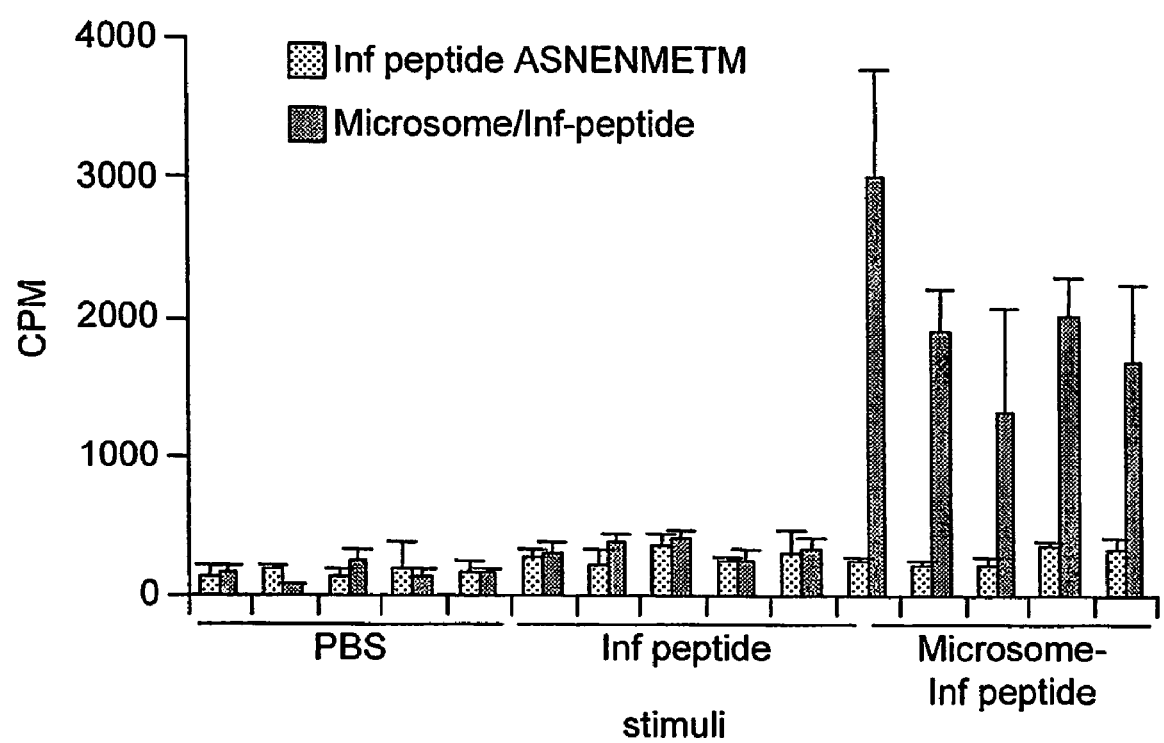
FIG. 10 shows the results of a study in which influenza viral peptide edited Kb-microsomes induced T-cell responses in vivo (five mice in each group).
Figure 11:
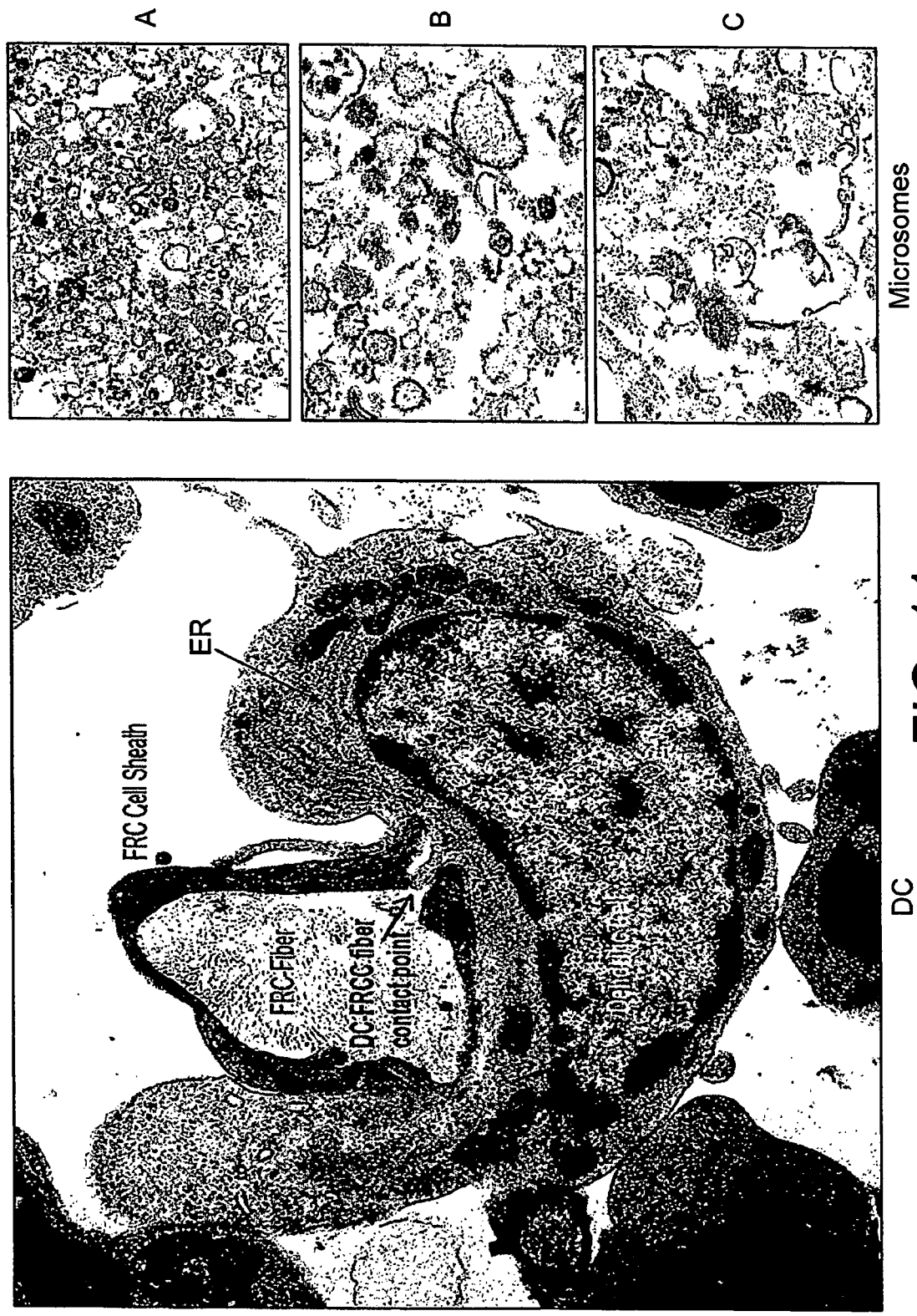
FIG. 11 shows electronmicrograph pictures of DC and prepared microsomes: (A) magnification ×12000 and (B) magnification ×40000 are prepared microsomes from RAW cells; (C) magnification ×40000 are microsomes inverted by repeated freeze-thaw and loaded with peptides, showing open or inverted microsomes. The loaded peptides can not be seen in the picture.

The Kb specific peptide (ASNENMETM) form mouse influenza virus was loaded into microsomes from Kb specific RAW cells. The loaded microsomes were used to immunize C57BL/6 mice. In separate groups, the PBS or peptide were used as controls. After two antigen administrations over a seven day period, T-cells were isolated from spleens and cross-cultured with PBS or peptide, peptide, or peptide-loaded microsomes for three days. T-cell proliferation was measured on day 4 after immunization. Results are shown in FIG. 10.

EXAMPLE 9

Effect on Melanoma Cells

Figure 12:
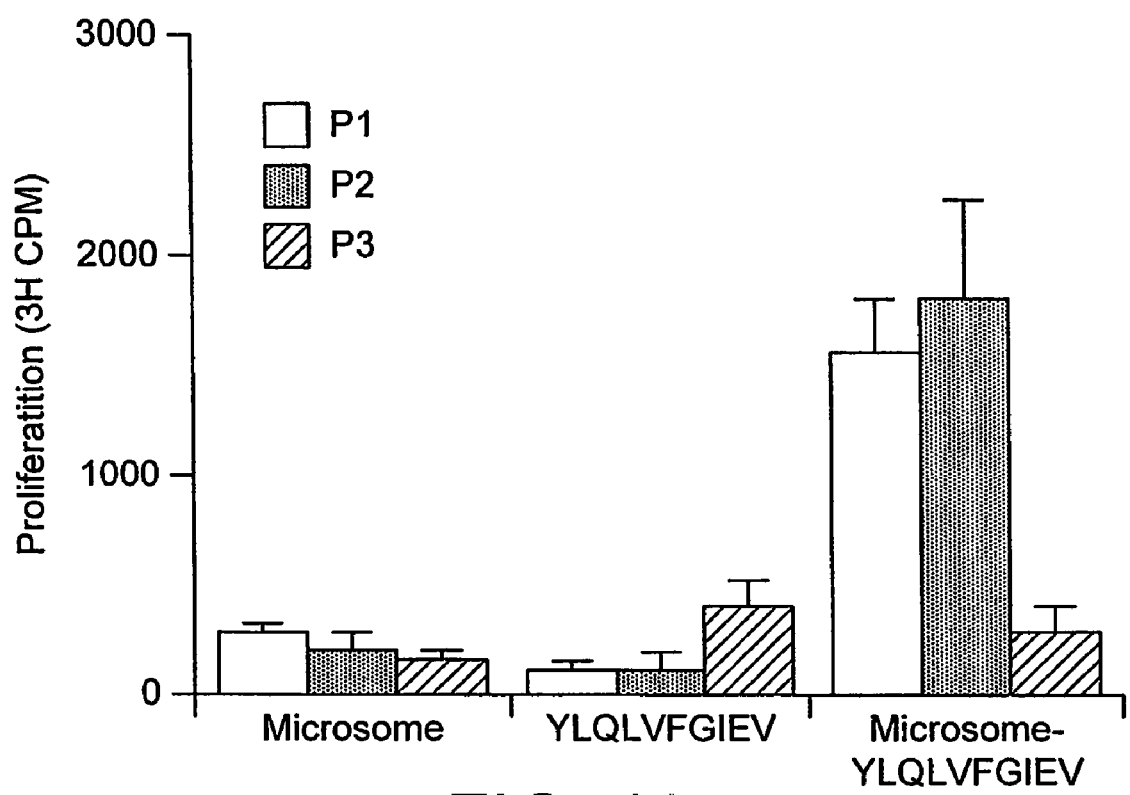
FIG. 12 shows the results of a study carried out on MAGE-A2 specific T-cells from A2 melanoma patients.

T-cells isolated from three A2 melanoma patients (P1, P2, P3), respectively, were stimulated with autologous tumor cells purified from surgical biopsies at one to one and with r-human IL-2 (10 U/mL) for four times with a 5 day interval between each administration. The specific anti-tumor responses were tested in comparison to the tumor cell line K259 by cytotoxic assay. The MAGE peptide was loaded to microsomes isolated from 221-A2 human B-cell line, in which the MHC locus is deleted, and subsequently transfected with HLA-A2. The T-cell lines from melanoma patients were cultured with peptide, microsomes, or peptide-loaded microsomes in normal medium for three days. The proliferation was measured at day 3. The results are shown in FIG. 12.

Discussion

These results demonstrate that the microsomes derived from the ER can be used to process edited antigenic peptides on MHC class I molecules and that the processed microsomes can reconstitute the functional surface of APCs to induce CTL responses. Thus, the antigenic peptide delivered by microsomal MHC class I in association with co-stimulatory molecules is a novel form of peptide vaccine.

REFERENCES TO TABLES 1 TO 7

1. Aarnoudse et al, *Int J Cancer* 82: 442 (1999)
2. Anichini et al, *J Exp Med* 177: 989 (1993)
3. Bakker et al, *Int J Cancer* 62: 97 (1995)
4. Baurain et al, *J Immunol* 164: 6057 (2000)
5. Bocchia et al, *Blood* 87: 3587 (1996)
6. Boel et al, *Immunity* 2: 167 (1995)
7. Bohm et al, *Int J Cancer* 75: 688 (1998)
8. Boon et al, *J Exp Med* 183: 725 (1996)
9. Brandle et al, *J Exp Med* 183: 2501 (1996)
10. Brichard et al, *Eur J Immunol* 26: 224 (1996)
11. Brossart et al, *Blood* 93: 4309 (1999)
12. Butterfield et al, *Cancer Res* 59: 3134 (1999)
13. Buzyn et al, *Eur J Immunol* 27: 2066 (1997)
14. Castelli et al, *J Exp Med* 181: 363 (1995)
15. Castelli et al, *J Immunol* 162: 1739 (1999)
16. Chaux et al, *J Immunol* 163: 2928 (1999a)
17. Chaux et al, *J Exp Med* 189: 767 (1999b)
18. Chen et al, *Proc Natl Acad Sci USA* 94: 1914 (1997)
19. Chiari et al, *Cancer Res* 59: 5785 (1999)
20. Connan et al, *Clin Exp Immunol* 114:166 (1998)
21. Correale et al, *J Natl Cancer Inst* 89: 293 (1997)
22. Coulie et al, *J Exp Med* 180: 35 (1994)

23. Coulie et al, *Proc Natl Acad Sci USA* 92: 7976 (1995)
24. Cox et al, *Science* 264: 716 (1994)
25. Dabovic et al, *Mamm Genome* 6: 571 (1995)
26. De Backer et al, *Cancer Res* 59: 3157 (1999)
27. De Plaen et al, *Immunogenetics* 40: 360 (1994)
28. Dermime et al, *Clin Cancer Res* 2: 593 (1996)
29. De Smet et al, *Immunogenetics* 19: 121 (1994)
30. De Smet et al, *Mol Cell Biol* 19: 7327 (1994)
31. Domenech et al, *J Immunol* 155: 4766 (1995)
32. Dudley et al, *J Exp Med* 184: 441 (1996)
33. Duffour et al, *Eur J Immunol* 29: 3329 (1999)
34. Fisk et al, *J Exp Med* 181: 2109 (1995)
35. Fleischhauer et al, *Int J Cancer* 68: 622 (1996)
36. Fleischhauer et al, *Cancer Res* 58: 2969 (1998)
37. Fujie et al, *Int J Cancer* 80: 169 (1999)
38. Gambacorti-Passerini et al, *Blood* 81:1369 (1993)
39. Gaudin et al, *J Immunol* 162: 1730 (1999)
40. Gaugler et al, *J Exp Med* 179: 921 (1994)
41. Gaugler et al, *Immunogenetics* 44: 323 (1996)
42. Gomi et al, *J Immunol* 163: 4994 (1999)
43. Greco et al, *Leukemia* 10: 693 (1996)
44. Gueguen et al, *J Immunol* 160: 6188 (1998)
45. Guilloux et al, *J Exp Med* 183: 1173 (1996)
46. Gure et al, *Int J Cancer* 85: 726 (2000)
47. Heidecker et al, *J Immunol* 164: 6041 (2000)
48. Herman et al, *Immunogenetics* 43: 377 (1996)
49. Hiltbold et al, *Cancer Res* 58: 5066 (1998)
50. Hogan et al, *Cancer Res* 58: 5144 (1998)
51. Hohn et al, *J Immunol* 163: 5715 (1999)
52. Huang et al, *J Immunol* 162: 6849 (1999)
53. Ikeda et al, *Immunity* 6: 199 (1997)
54. Jager et al, *J Exp Med* 187: 265 (1998)
55. Jager et al, *J Exp Med* 191: 625 (2000)
56. Jassim et al, *Eur J Immunol* 19: 1215 (1989)
57. Kang et al, *J Immunol* 155: 1343 (1995)
58. Kawakami et al, *Proc Natl Acad Sci USA* 91: 3515 (1994a)
59. Kawakami et al, *Proc Natl Acad Sci USA* 91: 6458 (1994b)
60. Kawakami et al, *J Exp Med* 180: 347 (1994c)
61. Kawakami et al, *J Immunol* 154: 3961 (1995)
62. Kawakami et al, *J Immunol* 161: 6985 (1998)
63. Kawakami et al, *Immunol Res* 16: 313 (1997)
64. Kawano et al, *Cancer Res* 60: 3550 (2000)
65. Kawashima et al, *Int J Cancer* 78: 518 (1998)
66. Kawashima et al, *Cancer Res* 59: 431 (1999)
67. Kikuchi et al, *Int J Cancer* 81: 459 (1999)
68. Kittlesen et al, *J Immunol* 160: 2099 (1998)
69. Kobayashi et al, *Cancer Res* 58: 296 (1998a)
70. Kobayashi et al, *Immunogenetics* 47: 398 (1998b)
71. Kono et al, *Int J Cancer* 78: 202 (1998)
72. Lethe et al, *Int J Cancer* 76: 903 (1998)
73. Li et al, *Cancer Immunol Immunother* 47: 32 (1998)
74. Lucas et al, *Cancer Res* 59: 4100 (1999)
75. Lucas et al, *Int J Cancer* 87: 55 (2000)
76. Lupetti et al, *J Exp Med* 188: 1005 (1998)
77. Lurquin et al, *Genomics* 46: 397 (1997)
78. Mandruzzato et al, *J Exp Med* 186: 785 (1997)
79. Manici et al, *J Exp Med* 189: 871 (1999)
80. Martelange et al, *Cancer Res* 60: 3848 (2000)
81. Minev et al, *Proc Natl Acad Sci USA* 97: 4796 (2000)
82. Moreau-Aubry et al, *J Exp Med* 191: 1617 (2000)
83. Morel et al, *Immunity* 12: 107 (2000)
84. Morioka et al, *Mol Immunol* 32: 573 (1995)
85. Nakao et al, *J Immunol* 164: 2565 (2000)
86. Noppen et al, *Int J Cancer* 87: 241 (2000)
87. Norbury et al, *Br J Haematol* 109: 616 (2000)
88. Ohminami et al, *Blood* 93: 925 (1999)
89. Oiso et al, *Int J Cancer* 81: 387 (1999)
90. Oka et al, *Immunogenetics* 51: 99 (2000)
91. Panelli et al, *J Immunol* 164: 4382 (2000)
92. Parkhurst et al, *Cancer Res* 58: 4895 (1998)
93. Pawelec et al, *Blood* 88: 2118 (1996)
94. Peiper et al, *Eur J Immunol* 27: 1115 (1997)
95. Peoples et al, *Proc Natl Acad Sci USA* 92: 432 (1995)
96. Pieper et al, *J Exp Med* 189: 757 (1999)
97. Robbins et al, *J Immunol* 154: 5944 (1995)
98. Robbins et al, *J Exp Med* 183: 1185 (1996)
99. Robbins et al, *J Immunol* 159: 303 (1997)
100. Robbins et al, *Harwood Acad Publ, London*, in press (2000)
101. Rongcun et al, *J Immunol* 163: 1037 (1999)
102. Ronsin et al, *J Immunol* 163: 483 (1999)
103. Russo et al, *Proc Natl Acad Sci USA* 97: 2185 (2000)
104. Salazar-Onfray et al, *Cancer Res* 57: 4348 (1997)
105. Scanlan et al, *Cancer Lett* 150: 155 (2000)
106. Schneider et al, *Int J Cancer* 75: 451 (1998)
107. Shichijo et al, *J Exp Med* 187: 277 (1998)
108. Skipper et al, *J Immunol* 157: 5027 (1996)
109. Suzuki et al, *J Immunol* 163: 2783 (1999)
110. Tahara et al, *Clin Cancer Res* 5: 2236 (1999)
111. Tanaka et al, *Cancer Res* 57: 4465 (1997)
112. Tanaka et al, *Br J Haematol* 109: 435 (2000)
113. Tanzarella et al, *Cancer Res* 59: 2668 (1999)
114. ten Bosch et al, *Leukemia* 9: 1344 (1995)
115. ten Bosch et al, *Blood* 88: 3522 (1996)
116. ten Bosch et al, *Blood* 94: 1038 (1999)
117. Topalian et al, *Proc Natl Acad Sci USA* 91: 9461 (1994)
118. Topalian et al, *J Exp Med* 183: 1965 (1996)
119. Traversari et al, *J Exp Med* 176: 1453 (1992)
120. Tsai et al, *J Immunol* 158: 1796 (1997)
121. Tsang et al, *J Natl Cancer Inst* 87: 982 (1995)
122. van Baren et al, *Br J Haematol* 102: 1376 (1998)
123. Van den Eynde et al, *J Exp Med* 182: 689 (1995)
124. Van den Eynde et al, *J Exp Med* 190: 1793 (1999)
125. van der Bruggen et al, *Science* 254: 1643 (1991)
126. van der Bruggen et al, *Eur J Immunol* 24: 3038 (1994a)
127. van der Bruggen et al, *Eur J Immunol* 24: 2134 (1994b)
128. Visseren et al, *Int J Cancer* 73: 125 (1997)
129. Vissers et al, *Cancer Res* 59: 5554 (1999)
130. Vonderheide et al, *Immunity* 10: 673 (1999)
131. Wang et al, *J Exp Med* 184: 2207 (1996a)
132. Wang et al, *J Exp Med* 183: 1131 (1996b)
133. Wang et al, *J Immunol* 160: 890 (1998a)
134. Wang et al, *J Immunol* 161: 3598 (1998b)
135. Wang et al, *Science* 284: 1351 (1999a)
136. Wang et al, *J Exp Med* 189: 1659 (1999b)
137. Wolfel et al, *Eur J Immunol* 24: 759 (1994)
138. Wolfel et al, *Science* 269: 1281 (1995)
139. Yang et al, *Cancer Res* 59: 4056 (1999)
140. Yasukawa et al, *Blood* 92: 3355 (1998)
141. Yotnda et al, *J Clin Invest* 101: 2290 (1998a)
142. Yotnda et al, *J Clin Invest* 102: 455 (1998b)
143. Yun et al, *Tissue Antigens* 54: 153 (1999)
144. Zarour et al, *Proc Natl Acad Sci USA* 97: 400 (2000)
145. Zeng et al, *J Immunol* 165: 1153 (2000)
146. Zorn et al, *Eur J Immunol* 29: 592 (1999a)
147. Zorn et al, *Eur J Immunol* 29: 602 (1999b)

TABLE 1

Class I HLA-restricted cancer/testis antigens. All these antigens were found to be expressed by normal spermatocytes and/or spermatogonia of testis. Occasionally MAGE-3, MAGE-4 and the GAGE genes were found to be expressed also in placenta [26, 24]. The NY-ESO-1 antigen was found to be expressed in normal ovary cells [18].

| Gene | HLA allele | Peptide epitope | Author [Ref] | Tissue distribution among tumors[a] |
|---|---|---|---|---|
| MAGE-A1 | A1 | EADPTGHSY | Traversari et al., 1992 [119] | Melanoma, breast carcinoma, SCLC [27, 29, 125] - |
| MAGE-A1 | A3 | SLFRAVITK | Chaux et al., 1999a [16] | sarcoma, NSCLC [27, 29] - thyroid medullary carcinoma |
| MAGE-A1 | A24 | NYKHCFPEI | Fujie et al., 1999 [37] | [125] - colon carcinoma[27] - laryngeal tumors [29] |
| MAGE-A1 | A28 | EVYDGREHSA | Chaux et al., 1999a [16] | |
| MAGE-A1, -A2 -A3, -A6 | B37 | REPVTKAEML | Tanzarella et al., 1999 [113] | Melanoma, colon and breast carcinomas, SCLC [27, 29, 125] - sarcoma, NSCLC [27, 29] - thyroid medullary carcinoma, H/N tumors, bronchial SCC [125] - laryngeal tumors [29] - leukemias [27] |
| MAGE-A1 | B53 | DPARYEFLW | Chaux et al., 1999a [16] | Melanoma, breast carcinoma, SCLC [27, 29, 125] - |
| MAGE-A1 | Cw2 | SAFPTTINF | Chaux et al., 1999a [16] | sarcoma, colon carcinoma, NSCLC [27, 29] - thyroid |
| MAGE-A1 | Cw3 | SAYGEPRKL | Chaux et al., 1999a [16] | medullary carcinoma [125] |
| MAGE-A1 | Cw16 | SAYGEPRKL | van der Bruggen et al., 1994b [127] | |
| MAGE-A2 | A2 | KMVELVHFL | Visseren et al., 1997 [128] | Melanoma, colon and breast carcinomaa, SCLC [27, 29, |
| MAGE-A2 | A2 | YLQLVFGIEV | Visseren et al., 1997 [128] | 124] - sarcoma, NSCLC [27, 29] - thyroid medullary |
| MAGE-A2 | A24 | EYLQLVFGI | Tahara et al., 1999 [110] | carcinoma [125] - laryngeal tumors [77] - leukemias [27] |
| MAGE-A3 | A1 | EVDPIGHLY | Gaugler et al., 1994 [40] | Melanoma, colon and breast carcinomas [27, 125] - H/N |
| MAGE-A3 | A2 | FLWGPRALV | van der Bruggen et al., 1994a [126] | tumors [18] - bronchial SCC, thyroid medullary and |
| MAGE-A3 | A24 | TFPDLESEF | Oiso et al., 1999 [89] | bladder carcinoma, sarcomas, SCLC, NSCLC [125] - |
| MAGE-A3 | A24 | IMPKAGLLI | Tanaka et al., 1997 [111] | leukemias [29] |
| MAGE-A3 | B44 | MEVDPIGHLY | Herman et al., 1996 [48], Fleischhauer et al., 1996 [35] | |
| MAGE-A3 | B52 | WQYFFPVIF | Russo et al. 2000 [103] | |
| MAGE-A4 | A2 | GVYDGREHTV | Duffour et al., 1999 [33] | Melanoma, NSCLC, sarcomas, esophageal, colon and breast carcinomas [27] |
| MAGE-A6 | A34 | MVKISGGPR | Zorn and Hercend, 1999b [147] | Melanoma, NSCLC, colon carcinoma, leukemias [27] |
| MAGE-A10 | A2 | GLYDGMEHL | Huang et al., 1999 [52] | Not defined |
| MAGE-A12 | Cw7 | VRIGHLYIL | Panelli et al., 2000 [91], Heidecker et al., 2000 [47] | Melanoma, myeloma, brain tumors, sarcoma, leukemias, SCLC, NSCLC, H/N tumors, bladder, lung, esophageal, breast, prostate and colorectal carcinoma [27] |
| BAGE | Cw16 | AARAVFLAL | Boël et al., 1995 [6] | Melanoma, bladder and mammary carcinomas, H/N SCC, NSCLC, sarcoma |
| DAM-6, -10 | A2 | FLWGPRAYA | Fleischhauer et al., 1998 [36] | Melanoma, skin tumors, mammary and ovarian carcinomas [77] - lung carcinoma [25, 77] - seminomas [25] |
| GAGE-1, -2, -8 | Cw6 | YRPRPRRY | Van den Eynde et al., 1995 [123] De Backer et al. 1999 [26] | Melanoma, sarcoma, NSCLC, SCLC, mesothelioma, sarcoma, seminoma, leukemias, lymphomas, H/N tumors, bladder, esophageal, mammary, colon, prostate carcinomas |
| GAGE-3, -4, -5, -6, -7B | A29 | YYWPRPRRY | De Backer et al. 1999 [26] | Melanomas, H/N tumors, leukemias, esophageal, lung and bladder carcinomas |
| NA88-A | B13 | MTQGQHFLQKV | Moreau-Aubry et al., 2000 [82] | Melanoma |
| NY-ESO-1 | A2 | SLLMWITQCFL | Jäger et al., 1998 [54] | Melanoma, sarcoma, B-lymphomas, hepatoma, H/N |
| | A2 | SLLMWITQC | Jäger et al., 1998 [54] | tumors, bladder, lung, prostate, ovarian, thyroid and |
| | A2 | QLSLLMWIT | Jäger et al., 1998 [54] | breast carcinomas [18] |
| NY-ESO-1a (CAG-3) | A31 | ASGPGGGAPR | Wang et al., 1998b [134] | |

[a]Tissue distribution among tumors as described in the given references when different from the paper first reporting the sequence of the epitope.

TABLE 2

Class I HLA-restricted melanocyte differentiation antigens. These antigens can only be expressed in normal and neoplastic cells of the same lineage (namley melanocytes, skin, retina, peripheral ganglia) or in normal cells of the prostate gland

| Gene | HLA allele | Peptide epitope | Authors [ref.] |
|---|---|---|---|
| MART-1/Melan-A[a] | A2 | AAGIGILTV | Coulie et al. 1994 [22] |
| | | | Kawakami et al., 1994a [58] |
| | A2 | EAAGIGILTV | Schneider et al., 1998 [106] |
| | A2 | ILTVILGVL | Castelli et al., 1995 [14] |
| | B45 | AEEAAGIGIL | Schneider et al., 1998 [106] |
| | B45 | AEEAAGIGILT | Schneider et al., 1998 [106] |
| MC1R | A2 | TILLGIFFL | Salazar-Onfray et al., 1997 [104] |
| | A2 | FLALIICNA | Salazar-Onfray et al., 1997 [104] |
| Gp100 | A2 | KTWGQYWQV | Bakker et al., 1995 [3] |
| | A2 | AMLGTHTMEV | Tsai et al., 1997 [120] |
| | A2 | MLGTHTMEV | Tsai et al., 1997 [120] |
| | A2 | SLADTNSLAV | Tsai et al., 1997 [120] |
| | A2 | ITDQVPFSV | Kawakami et al., 1995 [61] |
| | A2 | LLDGTATLRL | Kawakami et al., 1994b [59] |

TABLE 2-continued

Class I HLA-restricted melanocyte differentiation antigens. These antigens can only be expressed in normal and neoplastic cells of the same lineage (namley melanocytes, skin, retina, peripheral ganglia) or in normal cells of the prostate gland

| Gene | HLA allele | Peptide epitope | Authors [ref.] |
|---|---|---|---|
| | A2 | YLEPGPVTA | Cox et al., 1994 [24] |
| | A2 | VLYRYGSFSV | Kawakami et al., 1995 [61] |
| | A2 | RLMKQDFSV | Kawakami et al., 1998 [62] |
| | A2 | RLPRIFCSC | Kawakami et al., 1998 [62] |
| | A3 | LIYRRRLMK | Kawakami et al., 1998 [62] |
| | A3 | ALNFPGSQK | Kawashima et al., 1998 [65] |
| | A3 | SLIYRRRLMK | Kawashima et al., 1998 [65] |
| | A3 | ALLAVGATK | Skipper et al., 1996 [108] |
| | A24 | VYFFLPDHL | Robbins et al., 1997 [99] |
| | Cw8 | SNDGPTLI | Castelli et al., 1999 [15] |
| PSA | A1 | VSHSFPHPLY | Corman et al., 1998 [20] |
| | A2 | FLTPKKLQCV | Correale et al., 1997 [21] |
| | A2 | VISNDVCAQV | Correale et al., 1997 [21] |
| PSM | A1 | HSTNGVTRIY | Corman et al., 1998 [20] |
| Tyrosinase | A1 | KCDICTDEY | Kittlesen et al., 1998 [68] |
| | A1 | SSDYVIPIGTY | Kawakami et al., 1998 [62] |
| | A2 | YMDGTMSQV | Wölfel et al., 1994 [137] |
| | A2 | MLLAVLYCL | Wölfel et al., 1994 [137] |
| | A24 | AFLPWHRLF | Kang et al., 1995 [57] |
| | B44 | SEIWRDIDF | Brichard et al., 1996 [10] |
| TRP-1 (or gp75) | A31 | MSLQRQFLR | Wang et al., 1996b [132] |
| TRP-2 | A2 | SVYDFFVWL | Parkhurst et al., 1998 [92] |
| | A2 | TLDSQVMSL | Noppen et al., 2000 [86] |
| | A31 | LLGPGRPYR | Wang et al., 1996a [131] |
| | A33 | LLGPGRPYR | Wang et al, 1998a [133] |
| | Cw8 | ANDPIFVVL | Castelli et al., 1999 [15] |

[a]Two different groups simultaneously discovered this gene and gave it two different names, MART-1 and Melan-A respectively.

TABLE 3

Class I HLA-restricted widely expressed antigens

| | HLA | | Tissue distribution | | |
|---|---|---|---|---|---|
| Gene | allele | Peptide epitope | Tumors | Normal tissues | Reference |
| ART-4 | A24 | AFLRHAAL DYPSLSATDI | SCC, SCLC, H/N tumors, leukemia, lung, esophageal, gastric, cervical, endometrial, ovarian and breast carcinomas | Testis, placenta, fetal liver | Kawano et al., 2000 [64] |
| CAMEL | A2 | MLMAQEALAFL | Melanoma | Testis, placenta, heart, skeletal muscle, pancreas | Aarnoudse et al., 1999 [1] |
| CEA | A2 | YLSGANLNL (CAP-1)[a] | Melanoma | Testis, placenta, heart, skeletal muscle, pancreas | Tsang et al., 1995 [121] |
| CEA | A3 | HLFGYSWYK | Colon, rectum, pancreas, gastric, breast and lung carcinomas | Gastrointestinal embryonic tissue | Kawashima et al., 1999 [66] |
| Cyp-B | A24 | KFHRVIKDF DFMIQGGDF | Lung adenocarcinoma, T cell leukemia, lymphosarcoma - bladder, ovarian, uterine and esophageal SCC | Ubiquitously expressed in normal tissues. | Gomi et al., 1999 [42] |
| HER2/neu | A2 | KIFGSLAFL | Melanoma - ovarian and breast carcinomas | Epithelial cells | Fisk et al., 1995 [34] |
| HER2/neu | A2 | IISAVVGIL | Melanoma, ovarian, pancreatic [96][b] and breast carcinomas | Epithelial cells | Peoples et al., 1995 [95] |
| HER2/neu | A2 | RLLQETELV | Melanoma, ovarian, gastric, pancreatic [96] and breast carcinomas | Epithelial cells | Kono et al., 1998 [71] |
| HER2/neu | A2 | VVLGVVFGI ILHNGAYSL YMIMVKCWMI | Melanoma, ovarian, gastric, pancreatic [96] and breast carcinomas | Epithelial cells | Rongcun et al., 1999 [101] |
| HER2/neu | A3 | VLRENTSPK | Melanoma, ovarian, gastric, pancreatic [96] and breast carcinomas | Epithelial cells | Kawashima et al., 1999 [66] |
| hTERT[c] | A2 | ILAKFLHWL | Lung and ovarian carcinomas - multiple myeloma, melanoma, sarcoma, acute leukemias, non-Hodgkin's lymphomas | Hematopoietic stem cells and progenitors; germinal center cells; basal keratinocytes; gonadal cells; certain proliferating epithelial cells | Vonderheide et al., 1999 [131] |
| hTRT[c] | A2 | ILAKFLHWL RLVDDFLLV | Lung, prostate and ovarian carcinomas, multiple myeloma, melanoma, sarcoma, acute leukemias, non-Hodgkin's lymphomas | Circulating B cells; germinal center B cells; thymocytes; CD34+ progenitor hemopoietic cells | Minev et al., 2000 [81] |

TABLE 3-continued

Class I HLA-restricted widely expressed antigens

| Gene | HLA allele | Peptide epitope | Tumors | Normal tissues | Reference |
|---|---|---|---|---|---|
| iCE | B7 | SPRWWPTCL | RCC | Kidney, colon, small intestine, liver, heart, pituitary gland, adrenal gland, prostate, stomach | Ronsin et al., 1999 [102] |
| MUC1 | A11 | STAPPAHGV | Breast and ovarian carcinomas, multiple myeloma, B-cell lymphoma | None[d] | Domenech et al. 1995 [31] |
| MUC1 | A2 | STAPPVHNV | Breast and ovarian carcinoma, multiple myeloma, B-cell lymphoma | None[d] | Brossart et al., 1999 [11] |
| MUC2 | A2 | LLNQLQVNL MLWGWREHV | Ovary, pancreas and breast mucinous tumors, colon carcinoma of non-mucinous type | Colon, small intestine, bronchus, cervix and gall bladder | Böhm et al., 1998 [7] |
| PRAME | A24 | LYVDSLFFL | Melanoma, H/N and lung SCC, NSCLC [122], RCC, adenocarcinoma, sarcoma, leukemias [122] | Testis, endometrium, ovary, adrenals, kidney, brain, skin | Ikeda et al., 1997 [53] |
| P15 | A24 | AYGLDFYIL | Melanoma | Testis, spleen, thymus, liver, kidney, adrenal tissue, lung tissue, retinal tissue | Robbins et al., 1995 [97] |
| RU1 | B51 | VPYGSFKHV | Melanoma, renal and bladder carcinomas | Testis, kidney, heart, skin, brain, ovary, liver, lung, lymphocytes, thymus, fibroblasts | Morel et al., 2000 [83] |
| RU2 | B7 | LPRWPPPQL | Melanoma, sarcomas, leukemia - brain, esophageal and H/N tumors - renal, colon, thyroid, mammary, bladder, prostatic and lung carcinomas | Testis, kidney, liver, urinary bladder | Van den Eynde et al. 1999 [124] |
| SART-1 | A24 | EYRGFTQDF | Esophageal, H/N and lung SCC - adenocarcinoma, uterine cancer | Testis, fetal liver | Kikuchi et al., 1999 [67] |
| SART-1 | A*2601 | KGSGKMKTE | Esophageal, H/N and lung SCC, adenocarcinoma, uterine cancer | Testis, fetal liver | Shichijo et al., 1998 [107] |
| SART-3 | A24 | VYDYNCHVDL AYIDFEMKI | H/N, esophageal and lung SCC, adenocarcinoma, leukemia, melanoma | Lymphoid cells, fibroblasts, testis, fetal liver | Yang et al., 1999 [139] |
| WT1 | A2 | RMFPNAPYL | Gastric, colon, lung, breast, ovary, uterine, thyroid and hepatocellular carcinomas - leukemia (including AML, ALL and CML) | Kidney, ovary, testis, spleen | Oka et al., 2000 [90] |

[a]CAP-1 is an alternative name of this peptide.
[b]Tissue distribution among tumors as described in the given references when different from the paper first reporting the sequence of the epitope.
[c]Telomerase is expressed in most human tumors: those listed were shown to be susceptible to lysis by cytotoxic T lymphocytes.
[d]All epithelial tissues express mucin like hyperglycosylated molecules.

TABLE 4

Class I HLA-restricted tumor specific antigens, including both unique (CDK-4, MUM-1, MUM-2, β-catenin, HLA-A2-R170I, ELF2m, myosin-m, caspase-8, KIAA0205, HSP70-2m) and shared (CAMEL, TRP-2/INT2, GnT-V, G 250) antigens

| Gene | HLA allele | Peptide epitope | Tumors | Normal tissues | Reference |
|---|---|---|---|---|---|
| AFP | A2 | GVALQTMKQ | Hepatocellular carcinoma | Fetal liver | Butterfield et al., 1999 [12] |
| β-catenin/m | A24 | SYLDSGIHF | Melanoma | None | Robbins et al. 1996 [98] |
| Caspase-8/m | B35 | FPSDSWCYF | H/N tumors | None | Mandruzzato et al., 1997 [78] |
| CDK-4/m | A2 | ACDPHSGHFV | Melanoma | None | Wölfel et al., 1995 [138] |
| ELF2M | A68 | ETVSEQSNV | Lung SCC | None | Hogan et al., 1998 [50] |
| GnT-V | A2 | VLPDVFIRC(V)[a] | Melanoma, brain tumors, sarcoma | Breast and brain (low expression) | Guilloux et al., 1996 [45] |
| G250 | A2 | HLSTAFARV | RCC, colon, ovarian and cervical carcinomas | None | Vissers et al., 1999 [129] |
| HA-A*0201-R170I | A2 | CVEWLRIYLENGK | RCC | None | Brändle et al., 1996 [9] |
| HSP70-2M | A2 | SLFEGIDIY | RCC, melanoma, neuroblastoma | None | Gaudin et al., 1999 [39] |
| HST-2 | A31 | YSWMDISCWI | Gastric signet cell carcinoma | None | Suzuki et al., 1999 [109] |
| KIAA0205 | B44*03 | AEPINIQTV | Bladder cancer | None | Gueguen et al., 1998 [44] |
| MUM-1 | B44 | EEKLIVVLF | Melanoma | None | Coulie et al., 1995 [23] |
| MUM-2 | B44 | SELFRSGLDY | Melanoma | None | Chiari et al., 1999 [19] |
| MUM-2 | Cw6 | FRSGLDSYV | Melanoma | None | Chiari et al., 1999 [19] |
| MUM-3 | A28 | EAFIQPITR | Melanoma | None | Baurain et al., 2000 [4] |
| Myosin/m | A3 | KINKNPKYK | Melanoma | None | Zorn and Hercend, 1999a [146] |
| RAGE | B7 | SPSSNRIRNT | Melanoma, sarcomas, mesotheliomas, H/N tumors, bladder, renal, colon and mammary carcinomas | Retina only | Gaugler et al., 1996 [41] |

TABLE 4-continued

Class I HLA-restricted tumor specific antigens, including both unique (CDK-4, MUM-1, MUM-2, β-catenin, HLA-A2-R170I, ELF2m, myosin-m, caspase-8, KIAA0205, HSP70-2m) and shared (CAMEL, TRP-2/INT2, GnT-V, G 250) antigens

| Gene | HLA allele | Peptide epitope | Tumors | Normal tissues | Reference |
|---|---|---|---|---|---|
| SART-2 | A24 | DYSARWNEI AYDFLYNYL SYTRLFLIL | H/N and lung SCC, lung adenocarcinoma, RCC, melanoma, brain tumors, esophageal and uterine cancers | None | Nakao et al., 2000 [85] |
| TRP-2/INT2 | A68 | EVISCKLIKR | Melanoma | None | Lupetti et al., 1998 [76] |
| 707-AP | A2 | RVAALARDA | Melanoma | None[b] | Morioka et al., 1995 [84] |

[a]VLPDVFIRC(V) = nonamer and decamer peptides are both recognized by CTLs.
[b]This antigen is not expressed in normal cells but, as the tissue of the testis wase not tested, it will not become clear to which category the antigen may belong until more information is available.

TABLE 5

Class II HLA-restricted antigens

| Gene | HLA-allele | Peptide epitope | Tumors | Normal tissues | Reference |
|---|---|---|---|---|---|
| *Epitopes from normal protein antigens* | | | | | |
| Annexin II | DRB*0401 | DVPKWISIMTERSVPH | Melanoma | Not done | Li et al., 1998 [73] |
| Gp100 | DRB1*0401 | WNRQLYPEWTEAQRLD | Melanoma | Melanocytes | Li et al., 1998 [73] |
| MAGE-1, -2, -3, -6 | DRB*1301, DRB*1302 | LLKYRAREPVTKAE | Melanoma, lung and breast carcinomas, H/N SCC | Testis, placenta | Chaux et al., 1999a [16] |
| MAGE-3 | DR*1101 | TSYVKVLHHMVKISG | Melanoma, lung and breast carcinomas, H/N SCC | Testis, placenta | Manici et al., 1999 [79] |
| MAGE-3 | DRB*1301, DRB*1302 | AELVHFLLLKYRAR | Melanoma, lung and breast carcinomas, H/N SCC | Testis, placenta | Chaux et al., 1999b [17] |
| MART-1/Melan-A | DRB1*0401 | RNGYRALMDKSLHVGTQCALTRR | Melanoma | Melanocytes | Zarour et al., 2000 [144] |
| MUC1 | DR3 | PGSTAPPAHGVT | Breast and ovarian cancers, multiple myeloma, B-cell lymphoma | None[a] | Hiltbold et al., 1998 [49] |
| NY-ESO-1 | DRB4*0101 | VLLKEFTVSG | Melanoma, B-lymphoma, hepatoma [18][b], sarcoma, H/N tumors, - bladder, lung, prostate, ovarian, thyroid and breast carcinomas | Testis | Zeng et al., 2000 [145] |
| NY-ESO-1 | DRB4*0101-0103 | PLPVPGVLLKEFTVSGNI VLLKEFTVSGNILTIRLT AADHRQLQLSISSCLQQL | B-lymphoma, melanoma, sarcoma, H/N tumors, hepatoma [18] - bladder, lung, prostate, ovarian, thyroid and breast carcinomas | Testis | Jäger et al. 2000 [55] |
| PSA | DR4 | ILLGRMSLFMPEDTG SLFHPEDTGQVFQ QVFQVSHSFPHPLYD NDLMLLRLSEPAELT KKLQCVQLHVISM GVLQGITSMGSEPCA | Prostate carcinoma | Prostate gland | Corman et al., 1998 [20] |
| Tyrosinase | DRB1*0401 | QNILLSNAPLGPQFP DYSYLQDSDPDSFQD SYLQDSDPDSFQD | Melanoma | Melanocytes | Topalian et al., 1994 [117] Topalian et al., 1996 [118] |
| Tyrosinase | DRB1*1501 | RHRPLQEVYPEANAPIGHNRE | Melanoma | Melanocytes | Kobayashi et al., 1998a [69] |
| Tyrosinase | DRB1*0405 | EIWRDIDFAHE | Melanoma | Melanocytes | Kobayashi et al., 1998b [70] |
| *Epitopes from mutated protein antigens* | | | | | |
| HPV-E7 | DR*0401, DR*0407 | LFMDTLSFVCPLC LFMDSLNFVCPWC | Cervical carcinoma | None | Höhn et al., 1999 [51] |

TABLE 5-continued

Class II HLA-restricted antigens

| Gene | HLA-allele | Peptide epitope | Tumors | Normal tissues | Reference |
|---|---|---|---|---|---|
| CDC27/m | DRB1*0401 | FSWAMDLDPKGA | Melanoma | None | Wang et al., 1999a [135] |
| TPI/m | DRB1*0101 | GELIGILNAAKVPAD | Melanoma | None | Pieper et al., 1999 [96] |

[a] All epithelial tissues express highly glycosilated mucins whereas tumor cells often show hypoglycosilated mucins with a normal protein sequence.
[b] Tissue distribution among tumors as described in the given references when different from the paper first reporting the sequence of the epitope.

TABLE 6

Epitopes derived from fusion proteins (fusion proteins are never found in normal tissues)

| Gene | HLA allele | Peptide epitope | Tissue distribution among tumors | Reference |
|---|---|---|---|---|
| HLA class I restricted epitopes | | | | |
| bcr-abl[a] | A2 | FMVELVEGA | CML | Buzyn et al., 1997 [13] |
|  |  | KLSEQESLL |  |  |
|  |  | MLTNSCVKL |  |  |
| bcr-abl p210(b3a2) | A2 | SSKALQRPV | CML | Yotnda et al., 1998a [141] |
| bcr-abl (b3a2) | A3 | ATGFKQSSK | CML | Greco et al., 1996 [43] |
|  |  | KQSSKALQR |  |  |
| bcr-abl p210 (b3a2) | A3, A11 | HSATGFKQSSK | CML | Bocchia et al., 1996 [5] |
| bcr-abl p210(b3a2) | A3 | KQSSKALQR | CML | Norbury et al., 2000 [87] |
| bcr-abl p210(b3a2) | B8 | GFKQSSKAL | CML | Norbury et al., 2000 [87] |
| ETV6/AML | A2 | RIAECILGM | ALL | Yotnda et al., 1998b [142] |
| HLA class II restricted epitopes | | | | |
| bcr-abl p190 (ela2) | DRB1*1501 | EGAFHGDAEALQRPVAS | ALL | Tanaka et al., 2000 [112] |
| bcr-abl p210 (b2a2) | DRB5*0101 | IPLTINKEEALQRPVAS | CML | ten Bosch et al., 1999 [116] |
| bcr-abl p210 (b3a2) | DRB1*0401 | ATGFKQSSKALQRPVAS | CML | ten Bosch et al., 1996 [115] |
| bcr-abl p210 (b3a2) | DRB1*1501 | ATGFKQSSKALQRPVAS | CML | ten Bosch et al., 1995 [114] |
| bcr-abl (b3a2) | DRB1*0901 | ATGFKQSSKALQRPVAS | CML | Yasukawa et al., 1998 [140] |
| bcr-abl (b3a2) | DRB1*1101 | LIVVIVHSATGFKQSSKALQRPVA | CML | Pawelec et al., 1996 [93] |
| bcr-abl (b3a2) | DR11 | IVHSATGFKQSSKALQRPVASDFEP | CML | Bocchia et al., 1996 [5] |
| Dek-cain | DRB4*0103 | TMKQICKKEIRRLHQY | AML | Ohminami et al., 1999 [88] |
| LDLR/FUT | DRB1*0101 | GGAPPVTWRRAPAPG WRRAPAPGAKAMAPG | Melanoma | Wang et al., 1999b [132] |
| Pml/RARα | DR11 | NSNHVASGAGEAAIETQSSSSEEIV [28] | APL | Gambacorti-Passerini et al., 1993 [38] |
| p190 minor bcr-abl (e1a2) | DRB1*1501 | EGAFHGDAEALQRPVAS | AML | Tanaka et al., 2000 [112] |
| TEL/AML1 | DP5, DP17 | IGRIAECILGMNPSR | AML | Yun et al., 1999 [143] |

[a] These bcr-abl epitopes are not true fusion proteins generated-epitopes, because they derive from outside the bcr-abl junction.

TABLE 7

Frequency of epitopes recognized by a given HLA allele

| Antigen | No. of epitopes | HLA-A | HLA-B | HLA-C |
|---|---|---|---|---|
| MAGE-1, -2, -3, -4, -6, -10, -12 | 24 | 13 (54%) | 7 (29%) | 4 (17%) |
| GAGE-1, -2, -3, -4, -5, -6, -7B, -8 | 8 | 5 (62.5%) | 0 | 3 (37.5%) |
| MART-1 | 6 | 4 (67%) | 2 (33%) | 0 |
| Gp100 | 12 | 11 (92%) | 0 | 1 (8%) |
| Tyrosinase | 6 | 5 (83%) | 1 (17%) | 0 |

TABLE 8

HCV Peptides Previously Determined to Be Recognized in HCV-Exposed Patients

|  | HCV peptide | Sequence | HLA restriction |
|---|---|---|---|
| Core | 1-9 | MSTNPKPQK | A11 |
|  | 1-9[a] | MSTNPKPQR | A11 |
|  | 27-36 | CQIVGGVYLL | B60 |
|  | 35-44 | YLLPRRGPRL | A2 |
|  | 41-49 | GPRLGVRAT | B7 |
|  | 43-51 | RLGVRATRK | A3 |
|  | 51-59 | KTSERSQPR | A3 |
|  | 88-96 | NEGLGWGAW | B44 |
|  | 88-96[a] | NEGCGWGAW | B44 |
|  | 132-140 | DLMGYIPLV | A2 |
|  | 169-177 | LPGCSFSIF | B7 |
|  | 178-187 | LLALLSCLTV | A2 |
| E1 | 234-242 | NASRCWVAM | B35 |
|  | 257-266 | QLRRHIDLLV | A2 |

TABLE 8-continued

HCV Peptides Previously Determined to Be Recognized in HCV-Exposed Patients

| | HCV peptide | Sequence | HLA restriction |
|---|---|---|---|
| | 290-298 | QLFTFSPRR | A3 |
| E2 | 401-411 | SLLAPGAKQNV | A2 |
| | 453-465 | PERLSCRPLTDFD | A2 |
| | 453-465a | PERLASCRPLTDF | A2 |
| | 460-469 | RPLTDFDQGW | B53 |
| | 489-496 | YPPKPCGI | B51 |
| | 569-578 | CVIGGAGNNT | B50 |
| | 621-628 | TINYTIFK | A11 |
| | 632-641 | RMYVGGVEHR | A3 |
| | 721-729 | LLFLLLADA | A2 |
| | 723-731 | FLLLADARV | A2 |
| NS2 | 826-838 | LMALTLSPYYKRY | A29 |
| | 827-834 | MALTLSPY | A29 |
| | 838-846 | YISWCLWWL | A23 |
| NS3 | 1073-1081 | CINGVCWTV | A2 |
| | 1131-1139 | YLVTRHADV | A2 |
| | 1169-1177 | LLCPAGHAV | A2 |
| | 1261-1270 | TLGFGAYMSK | A11 |
| | 1262-1270 | LGFGAYMSK | A3 |
| | 1265-1274 | GAYMSKAHGV | A3 |
| | 1287-1296 | TGAPVTYSTY | A2 |
| | 1287-1296a | TGSPITYSTY | A2 |
| | 1391-1399 | LIFCHSKKK | A3 |
| | 1395-1403 | HSKKKCDEL | B8 |
| | 1406-1415 | KLVALGINAV | A2 |
| NS4 | 1585-1593 | YLVAYQATV | A2 |
| | 1611-1618 | LIRLKPTL | B8 |
| | 1636-1643 | TLTHPVTK | A11 |
| | 1661-1669 | VLVGGVLAA | A2 |
| | 1764-1772 | HMWNFISGI | A2 |
| | 1789-1797 | SLMAFTAAV | A2 |
| | 1807-1816 | LLFNILGGWV | A2 |
| | 1851-1859 | ILAGYGAGV | A2 |
| | 1858-1867 | GVAGALVAFK | A3 |
| | 1859-1867 | VAGALVAFK | A3 |
| | 1915-1923 | WMNRLIAFA | A2 |
| NS5 | 2218-2226 | NHDSPDAEL | B38 |
| | 2252-2260 | ILDSFDPLV | A2 |
| | 2267-2276 | REISVPAEIL | B60 |
| | 2510-2518 | SLTPPHSAK | A3 |
| | 2578-2587 | RLIVFPDLGV | A2 |
| | 2588-2596 | RVCEKMALY | A3 |
| | 2629-2637 | KSKKTPMGF | B57 |
| | 2727-2735 | GLQDCTMLV | A2 |
| | 2794-2802 | HDGAGKRVY | B38 |
| | 2794-2804 | HDGAGKRVYYL | B38 |
| | 3003-3011 | VGIYLLPNR | A31 | from Anthony et al Clinical Immunol., vol. 103, pages 264-276 (2002).

TABLE 9

HIV-CTL peptide epitopes

| Peptide sequence | Gene product | Position | Clade specificity | HLA restriction |
|---|---|---|---|---|
| GSEELRSLY | p17 | 71-79 | B | A1 |
| ISERILSTY | Rev | 55-63 | B | A1 |
| ILKD/EPVHGV | Pol | 476-484 | A/B | A2 |
| SLF/YNTVATL | p17 | 77-85 | A/B | A2 |
| TLNAWVKVI/V | p24 | 150-159 | A/B | A2 |
| ALKHRAYEL/ AFHHVAREL | Nef | 190-198 | A/B | A2 |
| KIRLRPGGK | p17 | 18-26 | A, B, D | A3 |
| RLRDLLLIVTR | gp41 | 775-785 | B | A3 |
| S/AIFQSSMTK | Pol | 325-333 | A/B | A3, A11, A33 |
| DLSHFLKEK | Nef | 86-94 | B | A3 |
| QVPLRPMTYK | Nef | 73-82 | B | A11 |
| AVDLSHFLK | Nef | 84-92 | B | A11 |
| IYQEPFKNLK | Pol | 508-516 | B | A11 |
| TLYCVHQRI | p17 | 84-92 | B | A11 |
| (R)YLR/KDQQLL | gp41 | 591-598 | A/B | A24 |
| LFCASDAKAY | gp120 | 53-62 | B | A24 |
| DSRLAFHHM | Nef | 186-194 | B | A24 |
| RDYVDRFFKTL | p24 | 296-306 | A | A24 |
| VSFEPIPIHY | gp120 | 263-272 | B | A29 |
| DTVLEDINL | Pol | 85-93 | A | A*6802 |
| ETAYFYILKL | Pol | 744-752 | A, B, D | A*6802 |
| ITLWQRPLV | Pol | 58-67 | A, B, D | A74 |
| IPRRIRQGL | gp41 | 848-856 | A, B, D | B7 |
| TPGPGV/IRYPL | Nef | 128-137 | B | B7 |
| FPVTPQVPLR | Nef | 68-77 | B | B7 |
| SPRTLNAWV | p24 | 148-156 | B | B7 |
| GPKVKQWPL | Pol | 171-180 | A, B, C, D | B8 |
| YLKDQQLL | gp41 | 586-593 | B | B8 |
| GGKKKYRL | p17 | 24-31 | A | B8 |
| DRFF/WKTLRA | p24 | 298-306 | A/B | B14 |
| DLNMMLNIV/ DLNTMLNVV | p24 | 183-191 | A/B | B14 |
| ERYLRDQQL | gp41 | 589-597 | A | B14 |
| RAEQASQEV | p24 | 305-313 | B | B14 |
| YPLTFGWCY/F | Nef | 135-143 | B/D | B18, B49 |
| FRDYVDRFY/FK | p24 | 293-302 | B, D/A, C | B18 |
| KRWIIL/MGLNK | p24 | 263-272 | B | B27 |
| TAVPWNASW | gp41 | 606-614 | B | B35 |
| VPLRPMTY | Nef | 75-82 | B | B35 |
| H/NPDIVIYQY | Pol | 342-350 | A/B | B35 |
| PPIPVGDIY | p24 | 260-268 | B | B35 |
| IPLTEEAEL | Pol | 447-455 | B | B51 |
| DPNPQEVVL | gp120 | 77-85 | B | B51 |
| LPCRIKQII | gp120 | 378-385 | B | B51 |
| AT/SQEVKNWM | p24 | 177-185 | A/B | B53 |
| DTINEEAAEW | p24 | 203-212 | A | B53 |
| QATQEVKNW | p24 | 308-316 | A | B53 |
| EVKNWMTETL | p24 | 313-322 | A | B53 |
| TSTLQEQIGW | p24 | 235-243 | A, B | B57/58 |
| L/ISPRTLNAW | p24 | 147-155 | A/B | B57/58 |
| KAFSPEVIPMF | p24 | 153-164 | B | B57/58 |
| QAISPRTL | p24 | 145-152 | B | Cw3 |
| SFNCGGEFF | gp120 | 376-383 | B | Cw4 |
| KYRLKHLVW | p17 | 728-736 | A | Cw4 |
| QASGEVKNW | p24 | 176-184 | B | Cw4 | from Kaul et al J. Clinical Invest., vol. 107, pages 1303-1310 (2001)

TABLE 10

HCV viral peptide antigens

| Peptide sequence | HLA restriction |
|---|---|
| CVIGGAGNNT | B50 |
| GPRLGVRAT | B7 |
| GPRLGVRA | B7 |
| WHYPPKPCGI | B51 |
| YPPKPCGIVPA | B51 |
| YPPKPCGI | B51 |
| STNPKPQK | A11 |
| MSTNPKPKKNK | A11 | from Koziel et al J. Virol., vol. 67, pages 7522-7532 (1993)

TABLE 11

HCV viral peptide antigens

| Peptide sequence | HLA restriction |
|---|---|
| CVNGVCWTV | A2 |
| KLVALGINAV | A2 | from He et al PNAS USA, vol. 96, pages 5692-5697 (1999)

The invention claimed is:

1. A composition for including an immune response comprising isolated inverted microsomes from an animal cell, or membrane fragments thereof, in association with a heterologous peptide antigen and a protein of the Major Histocompatibility Complex (MHC), wherein said peptide antigen and said protein of the MHC are externally disposed.

2. A composition as claimed in claim 1, in which the microsome is from the endoplasmic reticulum of the cell.

3. A composition as claimed in claim 1, in which the protein of the MHC is from a heterologous source with respect to the cell from which the microsomes are obtained.

4. A composition as claimed in claim 1, in which the composition additionally comprises one or more cytokines.

5. A composition as claimed in claim 4, in which the cytokine is IL-2.

6. A composition as claimed in claim 1, in which the antigen is from a viral, bacterial, yeast, fungal, or protozoan origin.

7. A kit of parts comprising a composition as claimed in claim 1 and one or more cytokines and/or adjuvants in sealed containers.

8. A kit of parts as claimed in claim 7, in which the cytokine is IL-2 or IFNγ.

9. A kit of parts comprising a composition as claimed in claim 1 and one or more cytokines and/or adjuvants for separate, subsequent or simultaneous administration to a subject.

10. A kit of parts as claimed in claim 9, in which the cytokine is IL-2 or IFNγ.

11. A composition comprising isolated inverted microsomes from an animal cell, or membrane fragments thereof, in association with a heterologous peptide antigen and a protein of the Major Histocompatibility Complex (MHC), wherein said peptide antigen and said protein of the MHC are externally disposed.

12. A composition as claimed in claim 11, in which the microsome is from the endoplasmic reticulum of the cell.

13. A composition as claimed in claim 11, in which the protein of the MHC is from a heterologous source with respect to the cell from which the microsomes are obtained.

14. A composition as claimed in claim 11, in which the composition additionally comprises one or more cytokines.

15. A composition as claimed in claim 14, in which the cytokine is IL-2.

16. A composition as claimed in claim 11, in which the antigen is from a viral, bacterial, yeast, fungal, or protozoan origin.

17. A kit of parts comprising a composition as claimed in claim 11 and one or more cytokines and/or adjuvants in sealed containers.

18. A kit of parts as claimed in claim 17, in which the cytokine is IL-2 or IFNγ.

19. A kit of parts comprising a composition as claimed in claim 11 and one or more cytokines and/or adjuvants for separate, subsequent or simultaneous administration to a subject.

20. A kit of parts as claimed in claim 19, in which the cytokine is IL-2or IFNγ.

* * * * *

UNITED STATES PATENT AND TRADEMARK OFFICE
CERTIFICATE OF CORRECTION

PATENT NO. : 7,498,046 B2
APPLICATION NO. : 10/566823
DATED : March 3, 2009
INVENTOR(S) : Wang et al.

Page 1 of 1

It is certified that error appears in the above-identified patent and that said Letters Patent is hereby corrected as shown below:

Column 133, Claim 1, Line 1, "including" should read -- inducing --.

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,498,046 B2
APPLICATION NO. : 10/566823
DATED : March 3, 2009
INVENTOR(S) : Wang et al.

It is certified that error appears in the above-identified patent and that said Letters Patent is hereby corrected as shown below:

Column 133, Claim 1, Line 34, "including" should read -- inducing --.

This certificate supersedes the Certificate of Correction issued January 12, 2010.

Signed and Sealed this

Second Day of February, 2010

David J. Kappos
*Director of the United States Patent and Trademark Office*